(12) United States Patent
Pilla et al.

(10) Patent No.: US 9,427,598 B2
(45) Date of Patent: Aug. 30, 2016

(54) METHOD AND APPARATUS FOR ELECTROMAGNETIC TREATMENT OF HEAD, CEREBRAL AND NEURAL INJURY IN ANIMALS AND HUMANS

(75) Inventors: Arthur A. Pilla, Oakland, NJ (US); Diana Casper, New York, NY (US); Berish Strauch, Rye, NY (US)

(73) Assignee: Rio Grande Neurosciences, Inc., Santa Fe, NM (US)

( * ) Notice: Subject to any disclaimer, the term of this patent is extended or adjusted under 35 U.S.C. 154(b) by 0 days.

(21) Appl. No.: 13/252,114

(22) Filed: Oct. 3, 2011

(65) Prior Publication Data

US 2012/0116149 A1    May 10, 2012

Related U.S. Application Data

(60) Provisional application No. 61/389,038, filed on Oct. 1, 2010, provisional application No. 61/456,310, filed on Nov. 4, 2010.

(51) Int. Cl.
*A61N 2/00* (2006.01)
*A61N 1/36* (2006.01)
*A61N 1/40* (2006.01)

(52) U.S. Cl.
CPC ............ *A61N 2/006* (2013.01); *A61N 1/36025* (2013.01); *A61N 1/40* (2013.01); *A61N 2/004* (2013.01)

(58) Field of Classification Search
CPC ............ A61N 2/02; A61N 2/06; A61N 2/12; A61N 2/00; A61N 2/004; A61N 2/006; A61N 2/008; A61N 1/36025; A61N 1/36082; A61N 1/36039; A61N 1/40; A61N 2005/0645

USPC ......... 600/9, 13, 14; 604/20; 607/3
See application file for complete search history.

(56) References Cited

U.S. PATENT DOCUMENTS 1,233,841 A    7/1917    Butcher
2,130,758 A    9/1938    Rose
(Continued)

FOREIGN PATENT DOCUMENTS

CA    0608693    11/1960
CN    1052053 A    6/1991
(Continued)

OTHER PUBLICATIONS

C. Rohde, A. Chiang, O. Adipoju, D. Casper, A.Pilla, "Effects of Pulsed Electromagnetic Fields on Interleukin-1β and Postoperative Pain: A Double-Blind, Placebo-Controlled, Pilot Study in Breast Reduction Patients," Plastic and Reconstructive Surgery (Jun. 2010), pp. 1-10.*
(Continued)

*Primary Examiner* — Navin Natnithithadha
*Assistant Examiner* — Kaylee Wilson
(74) *Attorney, Agent, or Firm* — Shay Glenn LLP

(57) ABSTRACT

Embodiments of the invention include methods of treating neurological injury and conditions, in particular, traumatic brain injury and physiological responses arising from injury or conditions. These treatment methods can include the steps of generating a pulsed electromagnetic field from a pulsed electromagnetic field source and applying the pulsed electromagnetic field 1 in proximity to a target region affected by the neurological injury or condition to reduce a physiological response to the neurological injury or condition.

34 Claims, 17 Drawing Sheets

(56) References Cited

U.S. PATENT DOCUMENTS

| | | |
|---|---|---|
| 2,276,996 A | 3/1942 | Milinowski |
| 2,648,727 A | 8/1953 | Rockwell |
| 3,043,310 A | 7/1962 | Milinowski |
| 3,181,535 A | 5/1965 | Milinowski |
| 3,270,746 A | 9/1966 | Kendall et al. |
| 3,329,148 A | 7/1967 | Kendall |
| 3,329,149 A | 7/1967 | Kendall et al. |
| 3,800,802 A | 4/1974 | Berry et al. |
| 3,890,953 A | 6/1975 | Kraus et al. |
| 3,915,151 A | 10/1975 | Kraus |
| 3,952,751 A | 4/1976 | Yarger |
| 3,978,864 A | 9/1976 | Smith |
| 4,028,518 A | 6/1977 | Boudouris et al. |
| 4,105,017 A | 8/1978 | Ryaby et al. |
| 4,197,851 A | 4/1980 | Fellus |
| 4,266,532 A | 5/1981 | Ryaby et al. |
| 4,305,115 A | 12/1981 | Armitage |
| 4,315,503 A | 2/1982 | Ryaby et al. |
| 4,338,945 A | 7/1982 | Kosugi et al. |
| 4,340,063 A | 7/1982 | Maurer |
| 4,374,482 A | 2/1983 | Moore et al. |
| 4,428,366 A | 1/1984 | Findl et al. |
| 4,454,882 A | 6/1984 | Takano |
| 4,548,208 A | 10/1985 | Niemi |
| 4,550,714 A | 11/1985 | Talish et al. |
| 4,556,051 A | 12/1985 | Maurer |
| 4,616,629 A | 10/1986 | Moore |
| 4,627,438 A | 12/1986 | Liss et al. |
| 4,654,574 A | 3/1987 | Thaler |
| 4,672,951 A | 6/1987 | Welch |
| 4,674,482 A | 6/1987 | Waltonen et al. |
| 4,765,310 A | 8/1988 | Deagle |
| 4,793,325 A | 12/1988 | Cadossi et al. |
| 4,829,984 A | 5/1989 | Gordon |
| 4,850,372 A | 7/1989 | Ko et al. |
| 4,889,526 A | 12/1989 | Rauscher et al. |
| 4,926,881 A | 5/1990 | Ichinomiya et al. |
| 4,940,453 A | 7/1990 | Cadwell |
| 4,993,413 A | 2/1991 | McLeod et al. |
| 4,998,532 A | 3/1991 | Griffith |
| 5,000,178 A | 3/1991 | Griffith |
| 5,014,699 A | 5/1991 | Pollack et al. |
| 5,116,304 A | 5/1992 | Cadwell |
| 5,123,898 A | 6/1992 | Liboff et al. |
| 5,147,284 A | 9/1992 | Fedorov et al. |
| 5,181,902 A | 1/1993 | Erickson et al. |
| 5,224,922 A | 7/1993 | Kurtz |
| 5,314,401 A | 5/1994 | Tepper |
| 5,338,286 A | 8/1994 | Abbott et al. |
| 5,370,680 A | 12/1994 | Proctor |
| 5,386,837 A | 2/1995 | Sterzer |
| 5,407,421 A | 4/1995 | Goldsmith |
| 5,441,495 A * | 8/1995 | Liboff ............... A61N 2/02 600/13 |
| 5,478,303 A | 12/1995 | Foley-Nolan et al. |
| 5,480,373 A | 1/1996 | Fischer et al. |
| 5,518,496 A | 5/1996 | McLeod et al. |
| 5,529,569 A | 6/1996 | Woo |
| 5,584,863 A | 12/1996 | Rauch et al. |
| 5,595,564 A | 1/1997 | Pinna |
| 5,707,334 A | 1/1998 | Young |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |
| 5,778,894 A | 7/1998 | Dorogi et al. |
| 5,792,209 A | 8/1998 | Varner et al. |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,968,527 A | 10/1999 | Litovitz |
| 5,990,177 A | 11/1999 | Brown |
| 5,997,464 A | 12/1999 | Blackwell |
| 6,004,257 A | 12/1999 | Jacobson |
| 6,083,149 A | 7/2000 | Wascher et al. |
| 6,086,525 A | 7/2000 | Davey et al. |
| 6,099,459 A | 8/2000 | Jacobson |
| 6,132,362 A | 10/2000 | Tepper et al. |
| 6,149,577 A | 11/2000 | Bouldin et al. |
| 6,155,966 A | 12/2000 | Parker |
| 6,190,893 B1 | 2/2001 | Shastri et al. |
| 6,200,259 B1 | 3/2001 | March |
| 6,213,934 B1 | 4/2001 | Bianco et al. |
| 6,231,187 B1 | 5/2001 | Munoz et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 * | 7/2001 | Tepper et al. ............... 600/14 |
| 6,261,831 B1 | 7/2001 | Agee |
| 6,301,506 B1 | 10/2001 | den Boer et al. |
| 6,321,120 B1 | 11/2001 | Surbeck et al. |
| 6,334,069 B1 | 12/2001 | George et al. |
| 6,348,070 B1 | 2/2002 | Teissl et al. |
| 6,418,345 B1 | 7/2002 | Tepper et al. |
| 6,421,562 B1 | 7/2002 | Ross |
| 6,424,863 B1 | 7/2002 | Flock et al. |
| 6,434,426 B1 | 8/2002 | Munneke et al. |
| 6,443,883 B1 | 9/2002 | Ostrow et al. |
| 6,450,941 B1 | 9/2002 | Larson |
| 6,458,151 B1 | 10/2002 | Saltiel |
| 6,458,157 B1 | 10/2002 | Suaning et al. |
| 6,463,336 B1 * | 10/2002 | Mawhinney ............... 607/156 |
| 6,556,872 B2 | 4/2003 | Hauck |
| 6,560,489 B2 | 5/2003 | Hauck |
| 6,561,968 B1 | 5/2003 | Dissing et al. |
| 6,569,654 B2 | 5/2003 | Shastri et al. |
| 6,589,159 B2 | 7/2003 | Paturu |
| 6,629,971 B2 | 10/2003 | McDaniel |
| 6,648,812 B2 | 11/2003 | Ardizzone |
| 6,675,047 B1 | 1/2004 | Konoplev et al. |
| 6,678,562 B1 | 1/2004 | Tepper et al. |
| 6,684,108 B2 | 1/2004 | Surbeck et al. |
| 6,701,185 B2 | 3/2004 | Burnett et al. |
| 6,839,589 B2 | 1/2005 | Petlan |
| 6,844,378 B1 | 1/2005 | Martin et al. |
| 6,919,205 B2 | 7/2005 | Brighton |
| 6,934,580 B1 | 8/2005 | Osorio et al. |
| 6,955,642 B1 * | 10/2005 | Simon ............... 600/14 |
| 7,010,353 B2 | 3/2006 | Gan et al. |
| 7,022,506 B2 | 4/2006 | Brighton et al. |
| 7,089,060 B1 | 8/2006 | Fitzsimmons |
| 7,130,692 B2 | 10/2006 | Brighton et al. |
| 7,160,241 B1 | 1/2007 | Herbst |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,288,062 B2 | 10/2007 | Spiegel |
| 7,333,858 B2 | 2/2008 | Killian et al. |
| 7,419,474 B2 | 9/2008 | Lee |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,520,849 B1 | 4/2009 | Simon |
| 7,551,957 B2 * | 6/2009 | Whelan et al. ............... 607/2 |
| 7,566,295 B2 | 7/2009 | Giardino et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,896,797 B2 | 3/2011 | Pilla et al. |
| 8,167,784 B1 * | 5/2012 | Honeycutt et al. ............... 600/14 |
| 2001/0007937 A1 | 7/2001 | MacKin |
| 2001/0031906 A1 | 10/2001 | Ishikawa et al. |
| 2001/0041820 A1 | 11/2001 | Woo |
| 2001/0044643 A1 | 11/2001 | Litovitz |
| 2002/0035358 A1 | 3/2002 | Wang |
| 2003/0023283 A1 | 1/2003 | McDaniel |
| 2003/0028072 A1 | 2/2003 | Fischell et al. |
| 2003/0093028 A1 | 5/2003 | Spiegel |
| 2003/0099979 A1 | 5/2003 | Ohtani et al. |
| 2003/0125769 A1 | 7/2003 | Brighton |
| 2003/0171640 A1 | 9/2003 | Canedo |

(56) References Cited

U.S. PATENT DOCUMENTS

| | | |
|---|---|---|
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0267333 A1 | 12/2004 | Kronberg |
| 2005/0049640 A1 | 3/2005 | Gurtner et al. |
| 2005/0059153 A1 | 3/2005 | George et al. |
| 2005/0182287 A1 | 8/2005 | Becker |
| 2005/0215842 A1 | 9/2005 | Pilla et al. |
| 2005/0222625 A1 | 10/2005 | Laniado et al. |
| 2005/0251229 A1* | 11/2005 | Pilla et al. ................ 607/86 |
| 2006/0009825 A1 | 1/2006 | Chiriaev et al. |
| 2006/0161226 A1 | 7/2006 | McMickle |
| 2006/0206174 A1 | 9/2006 | Honeycutt et al. |
| 2006/0212077 A1 | 9/2006 | Pilla et al. |
| 2006/0293724 A1 | 12/2006 | Kronberg et al. |
| 2007/0026514 A1 | 2/2007 | Pilla et al. |
| 2007/0043254 A1 | 2/2007 | DeMarco |
| 2007/0060954 A1* | 3/2007 | Cameron ............ A61N 1/0553 607/2 |
| 2007/0149901 A1 | 6/2007 | Gordon et al. |
| 2007/0173904 A1* | 7/2007 | Pilla ................ 607/50 |
| 2007/0203390 A1 | 8/2007 | Rohan et al. |
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0039901 A1 | 2/2008 | Kronberg et al. |
| 2008/0058793 A1 | 3/2008 | Pilla et al. |
| 2008/0132971 A1 | 6/2008 | Pilla et al. |
| 2008/0140155 A1 | 6/2008 | Pilla et al. |
| 2008/0200749 A1 | 8/2008 | Zheng et al. |
| 2008/0208287 A1* | 8/2008 | Palermo et al. ........... 607/48 |
| 2008/0217263 A1 | 9/2008 | Higgins et al. |
| 2008/0288035 A1 | 11/2008 | Gill et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0099623 A1 | 4/2009 | Bentwich |
| 2009/0105781 A1 | 4/2009 | Brighton |
| 2009/0216068 A1 | 8/2009 | Thomas et al. |
| 2009/0326315 A1 | 12/2009 | Nishi et al. |
| 2010/0004500 A1 | 1/2010 | Gliner et al. |
| 2010/0005571 A1 | 1/2010 | Moss et al. |
| 2010/0121407 A1* | 5/2010 | Pfaff et al. .............. 607/45 |
| 2010/0179373 A1 | 7/2010 | Pilla et al. |
| 2010/0210893 A1 | 8/2010 | Pilla |
| 2010/0222631 A1 | 9/2010 | Pilla |
| 2011/0112352 A1 | 5/2011 | Pilla et al. |
| 2011/0152598 A1 | 6/2011 | Pilla et al. |
| 2011/0184223 A1 | 7/2011 | Peterchev et al. |
| 2011/0190849 A1 | 8/2011 | Faltys et al. |
| 2011/0207989 A1 | 8/2011 | Pilla et al. |
| 2011/0213195 A1 | 9/2011 | Kraus et al. |
| 2013/0035539 A1 | 2/2013 | Kornstein |
| 2013/0274540 A1 | 10/2013 | Pilla et al. |
| 2014/0213843 A1 | 7/2014 | Pilla et al. |
| 2014/0213844 A1 | 7/2014 | Pilla et al. |
| 2015/0196771 A1 | 7/2015 | Pilla et al. |
| 2015/0217126 A1 | 8/2015 | Pilla |

FOREIGN PATENT DOCUMENTS

| | | |
|---|---|---|
| CN | 1408448 A | 4/2003 |
| CN | 102006793 A | 4/2011 |
| CN | 102151362 A | 8/2011 |
| DE | 970276 | 9/1958 |
| EP | 543152 A2 | 10/1992 |
| EP | 0500983 | 7/1995 |
| EP | 1167070 A1 | 1/2002 |
| FR | 748828 | 4/1933 |
| GB | 0604107 | 6/1948 |
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |
| WO | WO 2005/051306 A2 | 6/2005 |
| WO | WO 2008/070001 A2 | 6/2008 |
| WO | WO 2009/155516 | 12/2009 |
| WO | WO 2010/067336 A2 | 6/2010 |
| WO | WO 2011/053607 A1 | 5/2011 |

OTHER PUBLICATIONS

M. Czosnyka, J.D. Pickard, "Monitoring and interpretation of intracranial pressure," J. Neurol. Neurosurg. Psychiatry (2004) 75:813-821.*

G.W. Arendash, J. Sanchez-Ramos, T. Mori, M. Mamcarz, X. Lin, M. Runfeldt, L. Wang, G. Zhang, V. Sava, J. Tan, C. Cao, "Electromagnetic Field Treatment Protects Against and Reverses Cognitive Impairment in Alzheimer's Disease Mice." Journal of Alzheimer's Disease, 19 (2010) pp. 191-210.*

S.W. Barger, A.D. Harmon, "Microglial activation by Alzheimer amyloid precursor protein and modulation by apolipoprotein E." Nautre, vol. 388 (Aug. 1997), pp. 878-881.*

F. Clausen, A. Hanell, M. Bjork, L. Hillered, A.K. mir, H. Gram, N. Marklund, "Neutralization of interleukin-1β modifies the inflammatory response and improves histological and cognitive outcome following traumatic brain injury in mice," European Journal of Neuroscience, vol. 30, pp. 385-396 (2009).*

Heff "Using Pulsed Energy Therapy for Brain Injury and Concussion" The Headliner, vol. X, Issue 4, p. 14, Fall 2008.*

Strauch et al. "Evidence-Based Use of Paulsed Electromagentic Field Therapy in Clinical Plastic Surgery" Aesthetic Surg J 2009; 29:135-143.*

World Health Organization "Neurlogical Disorders: public health chanllenges" 2006.*

Pilla, Arthur A.; U.S. Appl. No. 13/285,761 entitled "Method and apparatus for electromagnetic enhancement of biochemical signaling pathways for therapeutics and prophylaxis in plants, animals and humans," filed Oct. 31, 2011.

DiMino et al.; U.S. Appl. No. 13/361,797 entitled "Method and devices for providing electromagnetic treatment in the presence of a metal-containing implant," filed Jan. 30, 2012.

Aaron et al.; Power frequency fields promote cell differentiation coincident with an increase in transforming growth factor-?1 expression; bioelectromagnetics; vol. 20; pp. 453-458; 1999.

Aaron et al.; The conservative treatment of osteonecrosis of the femoral head. A comparison of core decompression and pulsing electromagnetic fields; Clin. Orthopaed. Rel. Res.; vol. 249; pp. 209-218; 1989.

Adair; A physical analysis of the ion parametric resonance model; Bioelectromagnetics; vol. 19; pp. 181-191; 1998.

Adair; Comment: Analyses of Models of Ion Actions Under the Combined Action of AC and DC Magnetic Fields; Bioelectromagnetics; vol. 27; No. 4; pp. 332-334; 2006.

Adair; Criticism of Lednev's mechanism for the influence of weak magnetic fields on biological systems; Bioelectromagnetics; vol. 13; pp. 231-235; 1992.

Adair; Static and low-frequency magnetic field effects: Health risks and therapies; Rep Prog Phys; vol. 63; pp. 415-454; 2000.

Akai et al.; Effect of electrical stimulation on musculoskeletal systems: a meta-analysis of controlled clinical trials; Bioelectromagnetics; vol. 23; pp. 132-143; 2002.

Ayrapetyan et al.; Magnetic fields alter electrical properties of solutions and their physiological effects; Bioelectromagnetics; vol. 15; pp. 133-142; 1994.

Bassett et al.; A non-operative salvage of surgically-resistant pseudoarthroses and non-unions by pulsing electromagnetic fields; Clin Orthop; vol. 124; pp. 117-131; 1977.

Bawin et al.; Effects of modulated VHF fields on the central nervous system; Ann NYAcad Sci; vol. 247; pp. 74-81; 1975.

Bawin et al.; Sensitivity of calcium binding in cerebral tissue to weak environmental electric fields oscillating at low frequency; Proc Nat'l Acad Sci, USA; pp. 1999-2003; 1976.

(56) References Cited

OTHER PUBLICATIONS

Bearden Jr.; Quantitation of submicrogram quantities of protein by an improved protein-dye binding assay; Biochim Biophys Acta; vol. 533; pp. 525-529; 1978.

Belyaev et al.; Frequency-dependent Effects ofELF Magnetic Field on Cromatin Conformation in *Escherichia Coli* Cells and Human Lymphocytes; Biochimica et Biophysica Acta; vol. 1526; pp. 269-276; 2001.

Binder et al.; Pulsed electromagnetic field therapy of persistent rotator cuff tendinitis: a double blind controlled assessment; Lancet; vol. 1 (8379); pp. 695-697; 1984.

Blackman et al.; A role for the magnetic field in the radiation induced efflux of calcium ions from brain tissue in vitro; Bioelectromagnetics; vol. 6; pp. 327-337; 1985.

Blackman et al.; Empirical test of an ion parametric resonance model for magnetic field interactions with PC-12 cells; Bioelectromagnetics; vol. 15: pp. 239-260; 1994.

Blackman et al.; Influence of electromagnetic fields on the efflux of calcium ions from brain tissue in vitro: A three-model analysis consistent with the frequency response up to 510 Hz; Bioelectromagnetics; vol. 9; pp. 215-227; 1988.

Blackman et al.; Multiple power-density windows and their possible origin; Bioelectromagnetics; vol. 10; pp. 115-128; 1989.

Blanchard et al.; Clarification and application of an ion parametric resonance model for magnetic field interactions with biological systems; Bioelectromagnetics; vol. 15; pp. 217-238; 1994.

Blank et al.; Do electromagnetic fields interact directly with DNA?; Bioelectromagnetics; vol. 18; pp. 111-115; 1997.

Blumenthal et al.; Effects of low-intensity AC and/or DC electromagnetic fields on cell attachment and induction of apoptosis; Bioelectromagnetics; vol. 18; pp. 264-272; 1997.

Cain; Stimulating Treatment; Orthopedic Technology Review; vol. 4; No. 4; pp. 31-34; 2002.

Chiabrera et al.; Effect of Lifetimes on Ligand Binding Modelled by the Density Operator; Bioelectrochemistry and Bioenergetics; vol. 30; pp. 35-42; 1993.

Clapham, D.; Calcium signaling; Cell; vol. 80; pp. 259-268; 1995.

Colbert et al.; Magnetic mattress pad use in patients with fibromyalgia: A randomized double-blind pilot study; J Back Musculoskeletal Rehab; vol. 13; 19-31; 1999.

Collacott et al.; Bipolar permanent magnets for the treatment of low back pain: A pilot study; JAMA; vol. 283; No. 10; pp. 1322-1325; Mar. 8, 2000.

Cox, J.; Interactive Properties of Calmodulin; Biochem J.; vol. 249; pp. 621-629; 1988.

Edmonds, D.; Larmor precession as a mechanism for the detection of static and alternating magnetic fields; Bioelectrochemistry and Bioenergetics; vol. 30; pp. 3-12; 1993.

Engström, S.; Dynamic properties of Lednev's parametric resonance mechanism; Bioelectromagnetics; vol. 17; pp. 58-70; 1996.

Fitzsimmons et al.; Combined magnetic fields increase net calcium flux in bone cells. Calcif. Tiss. Intl.; vol. 55; pp. 376-380; 1994.

Halle, B.; On the cyclotron resonance mechanism for magnetic field effects on transmembrane ion conductivity; Bioelectromagnetics; vol. 9; pp. 381-385; 1988.

Johansson, et al.; Brij 58, a polyoxyethylene acyl ether, creates membrane vesicles of uniform sidedness: A new tool to obtain inside-out (cytoplasmic side-out) plasma membrane vesicle; Plant J.; vol. 7; pp. 165-173; 1995.

Kloth et al.; Effect of Pulsed Radio Frequency Stimulation on Wound Healing: A Double-Blind Pilot Clinical Study; in "Electricity and Magnetism in Biology and Medicine"; Bersani F, ed,, Plenum, New York; pp. 875-878; 1999.

Koch, et al.; Interaction between weak low-frequency magnetic fields and cell membranes; Bioelectromagnetics; vol. 24; pp. 39-402; 2003.

Körner et al.; Surface properties of right side-out plasma membrane vesicles isolated from barley roots and leaves; Plant Physiol.; vol. 79; pp. 72-79; 1985.

Lansdown et al.; Sequential changes in trace metal, metallothionein and calmodulin concentrations in healing skin wounds; J. Anat.; vol. 195; pp. 375-386; 1999.

Larsson et al.; Isolation of highly purified plant plasma membranes and separation of inside-out and rightside-out vesicles; Methods Enzymol; vol. 228; pp. 451-469; 1994.

Liboff, et al.; Geomagnetic cyclotron resonance in living cells; J Biol Phys; vol. 9; pp. 99-102; 1985.

Liboff, et al.; Kinetics of channelized membrane ions in magnetic fields; Bioelectromagnetics; vol. 9; pp. 39-51; 1988.

Likic et al.; Dynamics of Ca2+-saturated Calmodulin D129N Mutant Studied by Multiple Molecular Dynamics Simulations; Protein Sci; vol. 12; pp. 2215-2229; 2003.

Lukas, T.; A Signal Transduction Pathway Model Prototype II: Application to Ca21-Calmodulin Signaling and Myosin Light Chain Phosphorylatiori; Biophysical Journal; vol. 87; pp. 1417-1425; 2004.

Man, et al.; The influence of permanent magnetic field therapy on wound healing in suction lipectomy patients: A double-blind study; Plastic and Reconstructive Surgery; vol. 104; pp. 2261-2296; 1999 (printed Jul. 17, 2010).

Markov, et al.; Weak static magnetic field modulation of myosin phosphorylation in a cell-free preparation: Calcium dependence; Bioelectrochemistry and Bioenergetics; vol. 43; pp. 233,238; 1997.

McDonald, F.; Effect of static magnetic fields on osteoblasts and fibroblasts in-vitro; Bioelectomagnetics; vol. 14; pp. 187-196; 1993.

McLean, et al.; Blockade of sensory neuron action potentials by a static magnetic field in the 10 mT range; Bioelectromagnetics; vol. 16; pp. 20-32; 1995.

McLeod, et al.; Dynamic characteristics of membrane ions in multifield configurations of low-frequency electromagnetic radiation; Bioelectromagnetics; vol. 7; pp. 177-189; 1986.

Mehler, et al.; Structural Dynamics of Calmodulin and Troponin C; Protein Engineering; vol. 4; No. 6; pp. 625-627; 1991.

Mooney; A randomized double blind prospective study of the efficacy of pulsed electromagnetic fields for interbody lumbar fusions; Spine; vol. 15; pp. 708-715; 1990.

Muehsam et al.; Lorentz Approach to Static Magnetic Field Effects on Bound Ion Dynamics and Binding Kinetics: Thermal Noise Considerations; Bioelectromagnetics; vol. 17; pp. 89-99; 1996.

Muehsam et al.; Weak Magnetic Field Modulation of Ion Dynamics in a Potential Well: Mechanistic and Thermal Noise Considerations; Bioelectrochem Bioenergetics; vol. 28; pp. 355-365; 1994.

Muehsam, et al.; The sensitivity of cells and tissues to exogenous fields: effects of target system initial state; Bioelectrochemistry and Bioenergetics; vol. 48; pp. 35-42; 1999.

Pilla et al.; EMF signals and ion/ligand binding kinetics:prediction of bioeffective waveform parameters; Bioelectrochemistry and Bioenergetics; vol. 48; pp. 27-34; 1999.

Pilla; Electrochemical information transfer at living cell membrane; Ann. N.Y.Acad. Sci.; vol. 238; p. 149-170; 1974.

Pilla; Low-intensity electromagnetic and mechanical modulation of bone growth and repair: are they equivalent?; Journal of Orthopedic Science; vol. 7; pp. 420-428; 2002.

Pilla; State of the art in electromagnetic therapeutics: soft tissue applications; Electricity and Magnetism in Biology and Medicine; Bersani (ed.); Kluwer Academic/Plenum Publishers; pp. 871-874; 1999.

Pilla; Weak time-varying and static magnetic fields: from Mechanisms to therapeutic applications; Biological Effects of Electro Magnetic Fields; P. Stavroulakis, ed. Springer Veriag; pp. 34-75; 2003.

Ryaby et al.; The role of insulin-like growth factor in magnetic field regulation of bone formation. Bioelectrochem. Bioenergetics; vol. 35; pp. 87-91; 1994.

Sisken, et al.; Static magnetic fields and nerve regeneration (presentation abstract); Bioelectromagnetics Society; 21st Ann Meeting, Long Beach, Jun. 20-24, 1999.

Valbona, et al.; Response of pain to static magnetic fields in post-polio patients: A doubleblind pilot study; Arch. Phys. Med. Rehabil.; vol. 78; pp. 1200-1203; 1997.

(56) References Cited

OTHER PUBLICATIONS

Weaver, et al.; The response of living cells to very weak electric fields: The thermal noise limit; Science; vol. 247; pp. 459-462; 1990.
Zhadin, M.; Combined action of static and alternating magnetic fields on ion motion in a macromolecule; Theoretical aspects; Bioelectromagnetics; vol. 19; pp. 279-292; 1998.
Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; 1997.
Zdeblick; A prospective, randomized study of lumbar fusion: preliminary results; Spine; vol. 18; pp. 983-991; 1993.
Albensi et al.; Diffusion and high resolution MRI of traumatic brain injury in rats: time course and correlation with histology. Exp Neurol 162, 61-72 (Mar. 2000).
Anderson et al.; Fluoro-jade B stains quiescent and reactive astrocytes in the rodent spinal cord. J Neurotrauma 20, 1223-31 (Nov. 2003).
Armonda et al.; Wartime traumatic cerebral vasospasm: recent review of combat casualties. Neurosurgery 59, 1215-25; discussion 1225 (Dec. 2006).
Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).
Auffray et al.; Blood monocytes: development, heterogeneity, and relationship with dendritic cells. Annu Rev Immunol 27, 669-92 (Jan. 2009).
Bassett et al.; Generation of electric potentials by bone in response to mechanical stress. Science 137, 1063-4 (Sep. 28, 1962).
Bassett, C. A.; Biological significance of piezoelectricity. Calc. Tiss. Res. 1, 252 (Dec. 1968).
Beaumont et al.; The effects of human corticotrophin releasing factor on motor and cognitive deficits after impact acceleration injury. Neurol Res 22, 665-73 (Oct. 2000).
Beaumont et al.; The impact-acceleration model of head injury: injury severity predicts motor and cognitive performance after trauma. Neurol Res, 21, 742-54 (Dec. 1999).
Beck et al.; The Bioelectromagnetics Society (History of the first 25 years); eds. Shappard, A. and Blackman, C.; 46 pgs.; (mo. unavailable) 2004.
Becker, T. O.; The bioelectric factors in amphibian limb regeneration. J. Bone Joint Surg. 43A, 643 (Jul. 1961).
Bederson et al.; Nuclear magnetic resonance imaging and spectroscopy in experimental brain edema in a rat model. J Neurosurg 64, 795-802 (May 1986).
Belanger et al.; Cognitive sequelae of blast-related versus other mechanisms of brain trauma. J Int Neuropsychol Soc 15(1), 1-8 (Jan. 2009).
Blackman et al.; Action of 50 Hz magnetic fields on neurite outgrowth in pheochromocytoma cells. Bioelectromagnetics 14, 273-86 (mo. unavailable) (1993).
Blackman et al.; Effects of ELF fields on calcium-ion efflux from brain tissue in vitro; Radiat Res; vol. 92(3); pp. 510-520; Dec. 1982.
Borbely et al.; Pulsed high-frequency electromagnetic field affects human sleep and sleep electroencephalogram. Neurosci Lett 275, 207-10 (Nov. 19, 1999).
Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).
Bredt, D. S.; Nitric oxide signaling specificity-the heart of the problem. J Cell Sci 116, 9-15 (Jan. 2003).
Brighton et al.; Signal transduction in electrically stimulated bone cells. J Bone Joint Surg Am 83-A, 1514-23 (Oct. 2001).
Brighton, C. T.; The treatment of non-unions with electricity. J Bone Joint Surg Am 63, 847-51 (Jun. 1981).
Brooks et al.; Magnetic resonance spectroscopy in traumatic brain injury. J Head Trauma Rehabil 16, 149-64 (Apr. 2001).

Burton, T.; New Test for Brain Injury on Horizon, The Wall Street Journal, New York, (Jul. 20, 2010).
Cammermeyer, J.; I. An evaluation of the significance of the "dark" neuron. Ergeb Anat Entwicklungsgesch 36, 1-61 (mo. unavailable) (1962).
Canals et al.; Neurotrophic and neurotoxic effects of nitric oxide on fetal midbrain cultures. J Neurochem 76, 56-68 (Jan. 2001).
Canseven et al.; Effects of ambient ELF magnetic fields: variations in electrolyte levels in the brain and blood plasma; Gazi Tip Dergisi / Gazi Medical Journal; 16(3); pp. 121-127; Sep. 2005.
Casper et al.; Dopaminergic neurons associate with blood vessels in neural transplants. Exp Neurol 184, 785-93 (Dec. 2003).
Casper et al.; Enhanced vascularization and survival of neural transplants with ex vivo angiogenic gene transfer. Cell Transpl. 11, 331-349 (mo. unavailable) (2002).
Cederberg et al.; What has inflammation to do with traumatic brain injury? Childs Nery Syst 26, 221-6 (Feb. 2010).
Cernak et al.; Cognitive deficits following blast injury-induced neurotrauma: possible involvement of nitric oxide. Brain Inj 15, 593-612 (Jul. 2001).
Cernak et al.; Traumatic brain injury: an overview of pathobiology with emphasis on military populations. J Cereb Blood Flow Metab 30, 255-66 (Feb. 2010).
Cernak et al.; Ultrastructural and functional characteristics of blast injury-induced neurotrauma. J Trauma 50, 695-706 (Apr. 2001).
Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.
Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.
Chiabrera et al.; The role of the magnetic field in the EM interaction with ligand binding; In: "Mechanistic Approaches to Interaction of Electric and Electromagnetic Fields With Living Systems;" Blank, Findl (eds); New York; Plenum Press; pp. 79-95; Oct. 31, 1987.
Ciani et al.; Akt pathway mediates a cGMP-dependent survival role of nitric oxide in cerebellar granule neurones. J Neurochem 81, 218-28 (Apr. 2002).
Colomer et al.; Physiological roles of the Ca2+/CaM-dependent protein kinase cascade in health and disease. Subcell Biochem 45, 169-214 (mo. unavailable) (2007).
Cook et al.; Resting EEG is affected by exposure to a pulsed ELF magnetic field. Bioelectromagnetics 25, 196-203 (Apr. 2004).
Cook et al.; The effects of pulsed, high-frequency radio waves on the rate of osteogenesis in the healing of extraction wounds in dogs; Oral Sug.; 32(6); (Dec. 1971).
Cork et al.; Computer-aided analysis of polarized neurite growth. Effects of applied electrical fields on neuronal development. J Neurosci Methods 32, 45-54 (Apr. 1990).
Courtney et al.; A thoracic mechanism of mild traumatic brain injury due to blast pressure waves. Med Hypotheses 72, 76-83 (Jan. 2009).
Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).
De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).
Dixon et al.; A controlled cortical impact model of traumatic brain injury in the rat. J Neurosci Methods 39, 253-62 (Oct. 1991).
Dixon et al.; A fluid percussion model of experimental brain injury in the rat. J Neurosurg 67, 110-9 (Jul. 1987).
Edwards et al.; Final results of MRC CRASH, a randomised placebo controlled trial of intravenous corticosteroid in adults with head injury-outcomes at 6 months. Lancet 365, 1957-9 (Jun. 2005).
Elder et al.; Blast-related mild traumatic brain injury: mechanisms of injury and impact on clinical care. Mt Sinai J Med 76, 111-8 (Apr. 2009).

(56) References Cited

OTHER PUBLICATIONS

Elder et al.; Increased locomotor activity in mice lacking the low-density lipoprotein receptor. Behav Brain Res 191, 256-65 (Aug. 2008).
Fabre et al.; Antidepressant efficacy and cognitive effects of repetitive transcranial magnetic stimulation in vascular depression: an open trial. Int J Geriatr Psychiatry 19, 833-42 (Sep. 2004).
Farndale et al.; The action of pulsed magnetic fields on cyclic AMP levels in cultured fibroblasts. Biochim Biophys Acta 881, 46-53 (Mar. 19, 1986).
Farrarelli et al.; Breakdown in cortical effective connectivity during midazolam-induced loss of consciousness. Proc Natl Acad Sci U S A 107, 2681-6 (Feb. 9, 2010).
Fassbender et al.; Temporal profile of release of interleukin-1beta in neurotrauma. Neurosci Lett 284, 135-8 (Apr. 2000).
Faul et al.; Traumatic brain injury in the United States (Emergency department visits, hospitalization and deaths 2002-2006); U.S. Dept. of Health and Human Services, 74 pgs.; Mar. 2010.
Fetler et al.; Brain under surveillance: the microglia patrol. Science 309, 392-3 (Jul. 15, 2005).
Fitzsimmons et al.; A pulsing electric field (PEF) increases human chondrocyte proliferation through a transduction pathway involving nitric oxide signaling. J Orthop Res 26, 854-9 (Jun. 2008).
Foda et al.; A new model of diffuse brain injury in rats. Part II: Morphological characterization. J Neurosurg 80, 301-13 (Feb. 1994).
Foley-Nolan et al.; Pulsed high frequency (27MHz) electromagnetic therapy for persistent neck pain. A double blind, placebo-controlled study of 20 patients. Orthopedics 13, 445-51 (Apr. 1990).
Friedman et al.; Quantitative proton MRS predicts outcome after traumatic brain injury. Neurology 52, 1384-91 (Apr. 1999).
Fukada et al.; On the piezoelectric effect of bone. J Phys Soc Japan 12 (10), 1158-1162 (Oct. 1957).
Gaetz, M.; The neurophysiology of brain injury. Clin Neurophysiol 115, 4-18 (Jan. 2004).
Garthwaite et al.; Cyclic GMP and cell death in rat cerebellar slices. Neuroscience 26, 321-6 (Jul. 1988).
Gasparovic et al.; Decrease and recovery of N-acetylaspartate/creatine in rat brain remote from focal injury. J Neurotrauma 18, 241-6 (Mar. 2001).
Ghirnikar et al.; Inflammation in traumatic brain injury: role of cytokines and chemokines. Neurochem Res 23, 329-40 (Mar. 1998).
Glass et al.; Mechanisms underlying inflammation in neurodegeneration. Cell 140, 918-34 (Mar. 19, 2010).
Gona et al.; Effects of 60 Hz electric and magnetic fields on the development of the rat cerebellum. Bioelectromagnetics 14, 433-47 (mo. unavailable) (1993).
Goodwin et al.; A double-blind study of capacitively coupled electrical stimulation as an adjunct to lumbar spinal fusions(printed from online source). Spine 24(13), 1349-1357 (Jul. 1999).
Graeber et al.; New expression of myelomonocytic antigens by microglia and perivascular cells following lethal motor neuron injury. J Neuroimmunol 27, 121-32 (May 1990).
Greenebaum et al.; Effects of pulsed magnetic fields on neurite outgrowth from chick embryo dorsal root ganglia. Bioelectromagnetics 17, 293-302 (mo. unavailable) (1996).
Hart, F.; A quantum mechanical model for bioelectromagnetic resonance phenomena; J Bioelectr; vol. 9; pp. 1-7; Jan. 1990.
Hellmich et al.; Dose-dependent neuronal injury after traumatic brain injury; Brain Research; 1044; pp. 144-154 (May 2005).
Hutchinson et al.; Inflammation in human brain injury: intracerebral concentrations of IL-1alpha, IL-1beta, and their endogenous inhibitor IL-1ra. J Neurotrauma 24, 1545-57 (Oct. 2007).
Ignarro et al.; Heme-dependent activation of guanylate cyclase by nitric oxide: a novel signal transduction mechanism. Blood Vessels 28, 67-73 (Nov.-Dec. 1991).
Ito et al.; Characterization of edema by diffusion-weighted imaging in experimental traumatic brain injury. J Neurosurg 84, 97-103 (Jan. 1996).

Jackson et al.; The demonstration of new human brain-specific proteins by high-resolution two-dimensional polyacrylamide gel electrophoresis. J Neurol Sci 49, 429-38; (Mar. 1981).
Jenrow et al.; Weak ELF magnetic field effects on hippocampal rhythmic slow activity. Exp Neurol 153, 328-34 (Oct. 1998).
Jokela et al.; Assessment of the magnetic field exposure due to the battery current of digital mobile phones. Health Phys 86, 56-66 (Jan. 2004).
Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-97; Oct. 31, 1987.
Jortner, B. S.; The return of the dark neuron. A histological artifact complicating contemporary neurotoxicologic evaluation. Neurotoxivology 27, 628-34 (Jul. 2006).
Kamm et al.; The effect of traumatic brain injury upon the concentration and expression of interleukin-1beta and interleukin-10 in the rat. J Trauma 60, 152-7 (Jan. 2006).
Kanje et al.; Pretreatment of rats with pulsed electromagnetic fields enhances regeneration of the sciatic nerve. Bioelectromagnetics 14, 353-9 (mo. unavailable) (1993).
Kingham et al.; Microglial secreted cathepsin B induces neuronal apoptosis. J Neurochem 76, 1475-84 (Mar. 2001).
Kjellbom et al.; Preparation and polypeptide composition of chlorophyll-free plasma membranes from leaves of light-grown spinach and barley; Physiol Plant; vol. 62; pp. 501-509; Dec. 1984.
Knowles et al.; Nitric oxide synthases in mammals. Biochem J 298, 249-58 (Mar. 1994).
Kossmann et al.; Intrathecal and serum interleukin-6 and the acute-phase response in patients with severe traumatic brain injuries. Shock 4, 311-7 (Nov. 1995).
Kramarenko et al.; Effects of high-frequency electromagnetic fields on human EEG: a brain mapping study. Int J Neurosci 113, 1007-19 (Jul. 2003).
Lai et al.; Magnetic-field-induced DNA strand breaks in brain cells of the rat. Environ Health Perspect 112, 687-94 (May 2004).
Langlois et al.; The epidemiology and impact of traumatic brain injury: a brief overview. J Head Trauma Rehabil 21, 375-8 (Aug. 2006).
Lednev, V.; Possible mechanism for the effect of weak magnetic fields on biological systems: Correction of the basic expression and its consequences; in: Electricity and magnetism in biology and medicine Blank (eds.); San Francisco, CA; San Francisco Press, Inc.; pp. 550-552; Oct. 1993.
Lednev, V.; Possible mechanism for the influence of weak magnetic fields on biological systems; Bioelectromagnetics; vol. 12; pp. 71-75; (mo. unavailable) 1991.
LeDoux, J.; Emotion: clues from the brain. Annu Rev Psychol 46, 209-35 (Jan. 1995).
Lee et al.; Nitric oxide in the healing wound: a time-course study. J Surg Res 101, 104-8 (Nov. 2001).
Lee et al.; Pulsed magnetic and electromagnetic fields in experimental achilles tendonitis in the rat: a prospective randomized study. Arch Phys Med Rehabil 78, 399-404 (Apr. 1997).
Lescot et al.; Temporal and regional changes after focal traumatic brain injury. J Neurotrauma 27, 85-94 (Jan. 2010).
Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296; Oct. 31, 1987.
Lighthall, J. W.; Controlled cortical impact: a new experimental brain injury model. J Neurotrauma 5, 1-15 (mo. unavailable) (1988).
Lincoln et al.; Low frequency of pathogenic mutations in the ubiquitin carboxy-terminal hydrolase gene in familial Parkinson's disease. Neuroreport 10, 427-9 (Feb. 1999).
Ling et al.; Explosive blast neurotrauma. J Neurotrauma 26, 815-25 (Jun. 2009).
Linovitz et al.; Combined magnetic fields accelerate and increase spine fusion: a double-blind, randomized, placebo controlled study(printed from online source). Spine 27, 1383-1389 (Jul. 2002).

(56) References Cited

OTHER PUBLICATIONS

Liu et al.; Ubiquitin C-terminal hydrolase-L1 as a biomarker for ischemic and traumatic brain injury in rats (Author Manuscript). Eur J Neurosci 31(4), 722-32 (Feb. 2010).
Louin et al.; Selective inhibition of inducible nitric oxide synthase reduces neurological deficit but not cerebral edema following traumatic brain injury. Neuropharmacology 50, 182-90 (Feb. 2006).
Maas et al.; Moderate and severe traumatic brain injury in adults. Lancet Neurol 7, 728-41 (Aug. 2008).
Maas et al.; Prognosis and clinical trial design in traumatic brain injury: the IMPACT study. J Neurotrauma 24, 232-8 (Feb. 2007).
Maas et al.; Why have recent trials of neuroprotective agents in head injury failed to how convincing efficacy? A pragmatic analysis and theoretical considerations. (printed from online source) Neurosurgery 44, 1286-98 (Jun. 1999).
Madhusoodanan et al.; NO-cGMP signaling and regenerative medicine involving stem cells. Neurochem Res 32, 681-94 (Apr.-May 2007).
Maeda et al.; Effect of water on piezoelectric, dielectric, and elastic properties of bone; Biopolymers 21(10); 2055-2068 (Oct. 1982).
Marmarou et al.; A new model of diffuse brain injury in rats. Part I: Pathophysiology and biomechanics. J Neurosurg 80, 291-300 (Feb. 1994).
Martin et al.; Parkinson's disease alpha-synuclein transgenic mice develop neuronal mitochondrial degeneration and cell death. J Neurosci 26, 41-50 (Jan. 2006).
McFarlane et al.; Changes in neurite outgrowth but not in cell division induced by low EMF exposure: influence of field strength and culture conditions on responses in rat PC12 pheochromocytoma cells. Bioelectrochemistry 52, 23-8 (Sep. 2000).
McIntosh et al.; Traumatic brain injury in the rat: characterization of a lateral fluid-percussion model. Neuroscience 28(1), 233-44 (mo. unavailable) (1989).
McIntosh et al.; Traumatic brain injury in the rat: characterization of a midline fluid-percussion model. Cent Nery Syst Trauma 4, 119-34 (mo. unavailable) (1987).
Mellor, S.; The pathogenesis of blast injury and its management. Br J Hosp Med 39, 536-9 (Jun. 1988).
Mont et al.; Pulsed electrcial stimulation to defer TKA in patients with knee osteoarthritis; The Cutting Edge; 29(10); pp. 887-892 (Oct. 2006).
Morganti-Kossmann et al.; Production of cytokines following brain injury: beneficial and deleterious for the damaged tissue. Mol Psychiatry 2, 133-6 (Mar. 1997).
Morris et al.; Place navigation impaired in rats with hippocampal lesions. Nature 297, 681-3 (Jun. 1982).
Naldini et al.; Role of inflammatory mediators in angiogenesis. Curr Drug Targets Inflamm Allergy 4, 3-8 (Feb. 2005).
Nara, et al.; Fourier Transform Infrared Spectroscopic Study on the Ca2+-bound Coordination Structures of Synthetic Peptide Analogues of the Calcium-binding Site III of Troponin C; Biopolymers; vol. 82; issue 4; pp. 339-343; Jul. 2006.
Narayan et al.; Clinical trials in head injury (Author Manuscript). J Neurotrauma 19, 503-57 (May 2002).
Nauta et al.; Silver impregnation of degenerating axons in the central nervous system: a modified technic. Stain Technol 29, 91-3 (Mar. 1954).
Northington et al.; Early Neurodegeneration after Hypoxia-Ischemia in Neonatal Rat Is Necrosis while Delayed Neuronal Death Is Apoptosis. Neurobiol Dis 8, 207-19 (Apr. 2001).
Oda et al.; Magnetic field exposure saves rat cerebellar granule neurons from apoptosis in vitro. Neurosci Lett 365, 83-6 (Jul. 22, 2004).
Ohkubo et al.; Acute effects of static magnetic fields on cutaneous microcirculation in rabbits; In Vivo; vol. 11; pp. 221-226; May-Jun. 1997.
Okano et al.; Biphasic effects of static magnetic fields on cutaneous microcirculation in rabbits; Bioelectromagnetics; vol. 20(3); pp. 161-171; (mo. unavailable) 1999.

Okie, S.; Traumatic brain injury in the war zone. N Engl J Med 352, 2043-7 (May 19, 2005).
Olbe et al.; The spinach plasma membrane Ca2b pump is a 120-kDa polypeptide regulated by calmodulinbinding to a terminal region; Physiol Plantarum; vol. 103; pp. 35-44; May 1998.
Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).
Papa et al.; Ubiquitin C-terminal hydrolase is a novel biomarker in humans for severe traumatic brain injury. Crit Care Med 38, 138-44 (Jan. 2010).
Pascual et al.; Time course of early metabolic changes following diffuse traumatic brain injury in rats as detected by (1)H NMR spectroscopy. J Neurotrauma 24, 944-59 (Jun. 2007).
Patino et al.; Pulsed electromagnetic fields in experimental cutaneous wound healing in rats. J Burn Care Rehabil 17, 528-31 (Nov./Dec. 1996).
Paylor et al.; Inbred strain differences in prepulse inhibition of the mouse startle response. Psychopharmacology (Berl) 132, 169-80 (Jul. 1997).
Pennington et al.; Pulsed, non-thermal, high-frequency electromagnetic energy (DIAPULSE) in the treatment of grade I and grade II ankle sprains. Mil Med 158, 101-4 (Feb. 1993).
Pfeffer et al.; Disturbed sleep/wake rhythms and neuronal cell loss in lateral hypothalamus and retina of mice with a spontaneous deletion in the ubiquitin carboxyl-terminal hydrolase L1 gene. Neurobiol Aging 33, 393-403, in press, Epub ahead of print (Apr. 2010).
Pilla et al.; Gap junction impedance tissue dielectrics and thermal noise limits for electromagnetic field bioeffects; Bioelectrochemistry and Bioenergetics; vol. 35; pp. 63-69; Nov. 1994.
Pilla, A.; Mechanisms and therapeutic applications of time-varying and static magnetic fields; In: Biological and Medical Aspects of Electromagnetic Fields (eds. Barnes et al.) CRC Press, Boca Raton FL, 351-411 (Oct. 2006).
Pilla; Electrochemical information and energy transfer in vivo; Proc. 7th IECEC; Washington, D.C.; American Chemical Society; pp. 761-764; (mo. unavailable) 1972.
Pineros et al.; Calcium channels in higher plant cells: Selectivity, regulation, and pharmacology; J Exp Bot; vol. 48; special issue; pp. 551-577; Mar. 1997.
Pirozzoli et al.; Effects of 50 Hz electromagnetic field exposure on apoptosis and differentiation in a neuroblastoma cell line. Bioelectromagnetics 24, 510-6 (Oct. 2003).
Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.
Reale et al.; Modulation of MCP-1 and iNOS by 50-Hz sinusoidal electromagnetic field. Nitric Oxide 15, 50-7 (Aug. 2006).
Ren et al.; Role of interleukin-1β during pain and inflammation (Author Manuscript). Brain Res Rev 60, 57-64 (Apr. 2009).
Rich et al.; Chronic caloric restriction reduces tissue damage and improves spatial memory in a rat model of traumatic brain injury. J Neurosci Res 88, 2933-9 (Oct. 2010).
Rogers et al.; Behavioral and functional analysis of mouse phenotype: SHIRPA, a proposed protocol for comprehensive phenotype assessment. Mamm Genome 8, 711-3 (Oct. 1997).
Rohde et al.; Effects of pulsed electromagnetic fields on interleukin-1 beta and postoperative pain: a double-blind, placebo-controlled, pilot study in breast reduction patients. Plast Reconstr Surg 125, 1620-9 (Jun. 2010).
Sagan, L.; Epidemiological and laboratory studies of power frequency electric and magnetic fields; JAMA; vol. 268(5); pp. 625-629; Aug. 5, 1992.
Saljo et al.; Exposure to short-lasting impulse noise causes microglial and astroglial cell activation in the adult rat brain. Pathophysiology 8, 105-111 (Dec. 2001).
Saljo et al.; Low-level blast raises intracranial pressure and impairs cognitive function in rats: prophylaxis with processed cereal feed. J Neurotrauma 27, 383-9 (Feb. 2010).

(56) References Cited

OTHER PUBLICATIONS

Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).
Sandyk, R.; Treatment with AC pulsed electromagnetic fields improves olfactory function in Parkinson's disease. Int J Neurosci 97, 225-33 (Apr. 1999).
Sapolsky; Glucocorticoid toxicity in the hippocampus: temporal aspects of neuronal vulnerability. Brain Res 359, 300-5 (Dec. 16, 1985).
Sarimov, et al.; Exposure to ELF Magnetic Field Tuned to Zn Inhibits Growth of Cancer Cells. Bioelectromagnetics; vol. 26; No. 8; pp. 631-638; Dec. 2005.
Sauerland et al.; Risks and benefits of preoperative high dose methylprednisolone in surgical patients: a systematic review. Drug Saf 23, 449-61 (Nov. 2000).
Schmued et al.; Fluoro-Jade: a novel fluorochrome for the sensitive and reliable histochemical localization of neuronal degeneration. Brain Res 751, 37-46 (Mar. 1997).
Seegers et al.; Activation of signal-transduction mechanisms may underlie the therapeutic effects of an applied electric field. Med Hypotheses 57, 224-30 (Aug. 2001).
Shupak et al.; Human exposure to a specific pulsed magnetic field: effects on thermal sensory and pain thresholds. Neurosci Lett 363, 157-62 (Jun. 10, 2004).
Slepko et al.; Progressive activation of adult microglial cells in vitro. Glia 16, 241-46 (Mar. 1996).
Smith, S.; Calcium cyclotron resonance and diatom mobility; Bioelectromagnetics; vol. 8; pp. 215-227; (mo. unavailable) 1987.
Stahel et al.; The role of the complement system in traumatic brain injury. Brain Res Brain Res Rev 27, 243-56 (Jul. 1998).
Steinberg et al.; Results of core decompression and grafting with and without electrical stimulation. Clin Orthop, 199-208 (Dec. 1989).
Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).
Terpolilli et al.; The novel nitric oxide synthase inhibitor 4-amino-tetrahydro-L-biopterine prevents brain edema formation and intracranial hypertension following traumatic brain injury in mice. J Neurotrauma 26, 1963-75 (Nov. 2009).
Thurman et al.; The epidemiology of sports-related traumatic brain injuries in the United States: recent developments. J Head Trauma Rehabil 13, 1-8 (Apr. 1998).
Trillo et al.; Magnetic fields at resonant conditions for the hydrogen ion affect neurite outgrowth in PC-12 cells: a test of the ion parametric resonance model. Bioelectromagnetics 17, 10-20 (mo. unavailable) (1996).
Unterberg et al.; Edema and brain trauma. Neuroscience 129(4), 1021-9 (mo. unavailable) (2004).
Vianale et al.; Extremely low frequency electromagnetic field enhances human keratinocyte cell growth and decreases proinflammatory chemokine production. Br J Dermatol 158(6), 1189-96 (Jun. 2008).
Weinstein, et al.; Ca2+-Binding and Structural Dynamics in the functions of Calmodulin; Ann. Rev. Physiol; vol. 56; pp. 213-236; Mar. 1994.
Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.
Weissman et al.; Activation and inactivation of neuronal nitric oxide synthase: characterization of Ca(2+)-dependent [125I]Calmodulin binding. Eur J Pharmacol 435, 9-18 (Jan. 2002).
Wenk, G.; The nucleus basalis magnocellularis cholinergic system: one hundred years of progress; Neurobiology of Learning and Memory; 67(2); 85-95 (Mar. 1997).
Williams et al.; Characterization of a new rat model of penetrating ballistic brain injury. J Neurotrauma 22, 313-31 (Feb. 2005).
Yasuda, I.; Part III. Clinical Studies: Mechanical and electrical callus; Annals of the New York Academy of Sciences; vol. 238; pp. 457-465 (Oct. 1974).
Yu et al.; Effects of 60 Hz electric and magnetic fields on maturation of the rat neopallium. Bioelectromagnetics 14, 449-58 (mo. unavailable) (1993).
Yumoto, et al.; Coordination Structures of Ca2+ and Mg2+ in Akazara Scallop Troponin C in Solution; Eur. J. Biochem; vol. 268(23); pp. 6284-6290; Dec. 2001.
Zaloshnja et al.; Prevalence of long-term disability from traumatic brain injury in the civilian population of the United States, 2005. J Head Trauma Rehabil 23, 394-400 (Nov./Dec. 2008).
Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.
Ziebell et al.; Involvement of pro- and anti-inflammatory cytokines and chemokines in the pathophysiology of traumatic brain injury. Neurotherapeutics 7, 22-30 (Jan. 2010).
Zizic et al.; The treatment of osteoarthritis of the knee with pulsed electrical stimulation. J Rheumatol 22, 1757-61 (Sep. 1995).
Ginsberg, A. J.; Ultrashort radio waves as a therapeutic agent. Med Record 140, 651-653 (Dec. 19, 1934).
Goligorsky et al.; Relationships between caveolae and eNOS: everything in proximity and the proximity of everything; Am J Physiol Renal Physiol; 283; pp. F1-F10; Jul. 2002.
Itoh et al.; Accelerated wound healing of pressure ulcers by pulsed high peak power electromagnetic energy (Diapulse). Decubitus 4(1), pp. 24-5, 29-30, 32 & 34 (Feb. 1991).
Kimura et al.; Recipricol regulation between nitric oxide and vascular endothelial growth factor in angiogenesis; Acta Biochimica Polonica; vol. 50, No. 1; pp. 49-59; (year of publication is sufficiently earlier than the effective U.S. filed and any foreign priority date) 2003.
Sisken et al.; Prospects on clinical applications of electrical stimulation for nerve regeneration. J Cell Biochem 52, 404-409 (Apr. 1993).
Teleman et al.; Kinetics of Ca2+ binding to calmodulin and its tryptic fragments studied by 43Ca-NMR. Biochim Biophys Acta 873, 204-13 (Sep. 1986).
Zhadin, et al.; Ion Cyclotron Resonance in Biomolecules; Biomed Sci; vol. 1; pp. 245-250; (year of publication is sufficiently earler than the effective U.S. filing date and any foreign priority date) 1990.
Pilla, A.; U.S. Appl. No. 14/058,764 entitled "Apparatus and Method for Electromagnetic Treatment of Plant, Animal, and Human Tissue, Organs, Cells, and Molecules," filed Oct. 21, 2013.
Pilla, A.; U.S. Appl. No. 14/058,973 entitled "Apparatus and Method for Electromagnetic Treatment of Plant, Animal, and Human Tissue, Organs, Cells, and Molecules," filed Oct. 21, 2013.
Pilla et al.; U.S. Appl. No. 14/171,613 entitled "Apparatus and method for electromagnetic treatment of neurodegenerative conditions," filed Feb. 3, 2014.
Pilla et al.; U.S. Appl. No. 14/354,587 entitled "Method and apparatus for electromagnetic treatment of cognition and neurological injury," filed Apr. 27, 2014.
DiMino et al.; U.S. Appl. No. 14/688,602 entitled "Two-part pulsed electromagnetic field applicator for application of therapeutic energy," filed Apr. 16, 2015.
Batchelor et al.; Exquisite sensitivity to subsecond, picomolar nitric oxide transients conferred on cells by guanylyl cyclase-coupled receptors; Proc. Natl. Acad. Sci. U.S.A.; 107(51); pp. 22060-22065; Dec. 21, 2010.
Binshtok et al.; Nociceptors are interleukin-1 beta sensors; J. Neurosci.; 28 (52); pp. 14062-14073; Dec. 24, 2008.
Bodian et al.; The visual analog scale for pain: clinical significance in postoperative patients; Anesthesiology; 95(6); pp. 1356-1361; Dec. 2001.
Callaghan et al.; Pulsed electromagnetic fields accelerate normal and diabetic wound healing by increasing endogenous FGF-2 release; Plast. Reconstr. Surg.; 121(1); pp. 130-141; Jan. 2008.

(56) References Cited

OTHER PUBLICATIONS

Coll et al.; Postoperative pain assessment tools in day surgery: literature review; J. Adv. Nurs.; 46(2); pp. 124-133; Apr. 2004.

Delle Monache et al.; Extremely low frequency electromagnetic fields (ELF-EMFs) induce in vitro angiogenesis process in human endothelial cells; Bioelectromagnetics; 29; pp. 640-648; Mar. 5, 2008.

Ha et al.; Nitric oxide prevents 6-hydroxydopamine induced apoptosis in PC12 cells through cGMP-dependent PI3 kinase/Akt activation; FASEB J.; 17(9); pp. 1036-1047; Jun. 2003.

Heden et al.; Effects of pulsed electromagnetic fields on postoperative pain: a double-blind randomized pilot study in breast augmentation patients; Aesthet. Plast. Surg.; 32; pp. 660-666; Jul. 2008.

Kehlet et al.; Evidence-based surgical care and the evolution of fast-track surgery; Ann. Surg.; 248(2); pp. 189-198; Aug. 2008.

Liu et al.; Efficacy of continuous wound catheters delivering local anesthetic for postoperative analgesia: a quantitative and qualitative systematic review of randomized controlled trials; J. Am. Coll. Surg.; 203(6); pp. 914-932; Dec. 31, 2006.

Miller et al.; Role of Ca2+/calmodulinstimulated cyclic nucleotide phosphodiesterase 1 in mediating cardiomyocyte hypertrophy; Circ. Res.; 105(10); pp. 956-964; Nov. 6, 2009.

Mo et al.; Kinetics of a cellular nitric oxide/cGMP/phosphodiesterase-5 pathway; J. Biol. Chem.; 279(25); pp. 26149-26158; Jun. 18, 2004.

Roland et al.; Effects of pulsed magnetic energy on a microsurgically transferred vessel; Plast. Reconstr. Surg.; 105(4); pp. 1371-1374; Apr. 2000.

Tepper et al.; Electromagnetic fields increase in vitro and in vivo angiogenesis through endothelial release of FGF-2; FASEB J.; 18(11); pp. 1231-1233; Aug. 2004.

Weber et al.; Pulsed magnetic fields applied to a transferred arterial loop support the rat groin composite flap; Plast. Reconstr. Surg.; 114(5); pp. 1185-1189; Oct. 2004.

Werner et al.; Regulation of wound healing by growth factors and cytokines; Physiol. Rev.; 83(3); pp. 835-870; Jul. 2003.

Yen-Patton et al.; Endothelial cell response to pulsed electromagnetic fields: stimulation of growth rate and angiogenesis in vitro; J. Cell Physiol.; 134(1); pp. 37-46; Jan. 1988.

Pilla; U.S. Appl. No. 14/932,928 entitled "Method and apparatus for electromagnetic treatment of living systems," filed Nov. 4, 2015.

Wikipedia; ISM band; 6 pages; retrieved Nov. 30, 2015 from the internet; ( https://en.wikipedia.org/w/index.php?title=ISM_band&oldid=690024749).

Klit et al.; Central post-stroke pain: clinical characteristics, pathophysiology, and management; Lancet Neurol.; 8(9); pp. 857-868; Sep. 2009.

\* cited by examiner

METHOD AND APPARATUS FOR ELECTROMAGNETIC TREATMENT OF HEAD, CEREBRAL AND NEURAL INJURY IN ANIMALS AND HUMANS

CROSS REFERENCE TO RELATED APPLICATIONS

This application claims the benefit of U.S. Provisional Application No. 61/389,038 filed Oct. 1, 2010 and U.S. Provisional Application No. 61/456,310 filed Nov. 4, 2010, the disclosure of which is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD

Described herein are electromagnetic treatment devices, systems and methods. Some embodiments pertain generally to a method and apparatus for therapeutic and prophylactic treatment of animal and human nervous system. In particular, some embodiments pertain to use of non-thermal time-varying electromagnetic fields configured to accelerate the asymmetrical kinetics of the binding of intracellular ions to their respective binding proteins which regulate the biochemical signaling pathways living systems employ to contain and reduce the inflammatory response to injury. Other embodiments pertain to the non-thermal application of repetitive pulse bursts of sinusoidal, rectangular, chaotic or arbitrary waveform electromagnetic fields to instantaneously accelerate ion-buffer binding in signaling pathways in animal and human nervous system using ultra lightweight portable coupling devices such as inductors and electrodes, driven by miniature signal generator circuitry that can be incorporated into an anatomical positioning device such as a dressing, bandage, compression bandage, compression dressing; lumbar or cervical back, shoulder, head, neck and other body portion wraps and supports; garments, hats, caps, helmets, mattress pads, seat cushions, beds, stretchers, and other body supports in cars, motorcycles, buses, trains, airplanes, boats, ships and the like.

Yet another embodiment pertains to application of sinusoidal, rectangular, chaotic or arbitrary waveform electromagnetic signals, having frequency components below about 100 GHz, configured to accelerate the binding of intracellular $Ca^{2+}$ to a buffer, such as CaM, to enhance biochemical signaling pathways in animal and human nervous system. Signals configured according to additional embodiments produce a net increase in a bound ion, such as $Ca^{2+}$, at CaM binding sites because the asymmetrical kinetics of Ca/CaM binding allows such signals to accumulate voltage induced at the ion binding site, thereby accelerating voltage-dependent ion binding. Examples of therapeutic and prophylactic applications of the present invention are modulation of biochemical signaling in anti-inflammatory pathways, modulation of biochemical signaling in cytokine release pathways, modulation of biochemical signaling in growth factor release pathways; edema and lymph reduction, anti-inflammatory, post surgical and post operative pain and edema relief, nerve, bone and organ pain relief, increased local blood flow, microvascular blood perfusion, treatment of tissue and organ ischemia, brain tissue ischemia from stroke or traumatic brain injury, treatment of neurological injury and neurodegenerative diseases such as Alzheimer's and Parkinson's; angiogenesis, neovascularization; enhanced immune response; enhanced effectiveness of pharmacological agents; nerve regeneration; prevention of apoptosis; modulation of heat shock proteins for prophylaxis and response to injury or pathology.

Some embodiments can also be used in conjunction with other therapeutic and prophylactic procedures and modalities such as heat, cold, light, ultrasound, mechanical manipulation, massage, physical therapy, wound dressings, orthopedic and other surgical fixation devices, and surgical interventions. In addition, any of the variations described herein can also be used in conjunction with one or more pharmacological agents. Any of the variations described herein can also be used with imaging or non-imaging diagnostic procedures.

In some variations the systems, devices and/or methods generally relate to application of electromagnetic fields (EMF), and in particular, pulsed electromagnetic fields (PEMF), including a subset of PEMF in a radio frequency domain (e.g., pulsed radio frequency or PRF), for the treatment of head, cerebral and neural injury, including neurodegenerative conditions in animals and humans.

BACKGROUND

Traumatic brain injury (hereinafter known as TBI) remains as one of the leading causes of morbidity and mortality for civilians and for soldiers on the battlefield and is a major health and socio-economic problem throughout the world. In currently deployed war-fighters, head injuries, the majority of which include the brain, account for 22% of all injuries and 56% of those are classified as moderate to severe. In January 2008, the Department of Defense reported that over 5,500 soldiers had suffered traumatic brain injury caused by explosive weaponry, including suicide bombings, mines that explode on impact, and missiles. In addition to the immediate needs of the wounded, traumatic brain injury may create long-term or even permanent cognitive, motor, and sensory disabilities that require ongoing support, rehabilitation, and treatment.

Additionally, traumatic brain injury is also a significant cause of death in civilians. Epidemiological data indicate that in the US, at least 1.4 to 2 million people are treated for traumatic brain injury every year, resulting in 56,000 deaths and 18,000 survivors suffering from neurological impairment. Annual costs in the US are estimated at $60 billion. The World Health Organization projected that by 2020, road traffic accidents, a major cause of traumatic brain injury, will rank third as a cause of the global burden of disease and disablement, behind only ischemic heart disease and unipolar depression. Recently, the demographics of traumatic brain injury have shifted to include more cases due to falls in middle-aged and older subjects. It is predicted that there will be 5 million head injuries over the next decade and 30 million worldwide.

Tissue damage from head injuries such as traumatic brain injury generally arises from the mechanical damage of the trauma event and subsequent secondary physiological responses to the trauma event. For example, moderate to severe traumatic brain injury can produce mechanical damage by direct trauma to brain tissue that can cause the disruption of cell membranes and blood vessels, resulting in direct and ischemic neuronal death. Then, secondary physiological responses such as inflammation and swelling can result in further damage and even death of healthy brain tissue. Importantly, even in the absence of direct mechanical injury (i.e. diffuse brain trauma), such secondary physiological responses can still occur and result in injury to healthy brain tissue. For example, astrocytes and microglia often react to head injury conditions and by secreting destructive cytokines (e.g. IL-1β, TNF-α, IFN-γ, and IL-6) as well as other inflammatory molecules, such as glutamate, reactive oxygen and nitrogen species, which, alone, or in combination, can be neurotoxic.

While the primary and immediate consequences of mechanical trauma to neurons cannot be undone, secondary pathological sequelae, specifically brain swelling and inflammation, are situational candidates for intervention. The toll of neurological deficits and mortality from TBI continue in the military and private sectors and, to date, there are no widely successful medical or surgical interventions to prevent neuronal death.

Current medical practice has attempted to use pharmaceuticals to mitigate and prevent tissue damage and injury resulting from secondary physiological responses of traumatic brain injury with little success. For example, intravenous, high-dose corticosteroids have been administered to reduce cerebral inflammation after traumatic brain injury, but several studies have demonstrated that steroids can be neurotoxic. In fact, results from a clinical randomized trial in 2005 tested whether a high dose regimen of the steroid methylprednisolone sodium succinate (MPSS), administered within 8 hours after injury, would improve survival after head injury. This trial was planned to randomize 20,000 patients and was powered to detect a drop in mortality from 15% to 13%, a small, but important improvement in outcome. However, the data and safety monitoring board halted the trial after half of the patients were enrolled as it became apparent that MPSS significantly increased mortality of severe injuries from 17.9% to 21.1% (p=0.0001).

The search for alternatives to improve morbidity and mortality from traumatic brain injury has not been fruitful. At least 21 multi-center clinical trials, aimed to determine the clinical value of a range of approaches, from steroids to calcium and glutamate antagonists to antioxidants and antifibrinolytic agents and hypothermia were conducted from 1985 to 2006, but unfortunately none have demonstrated a convincing benefit in the overall traumatic brain injury population. In spite of extremely promising pre-clinical data and early phase trials, no agent has yet been shown convincingly in a phase III trial to have clear benefit in terms of improving functional outcome after traumatic brain injury. Importantly, a common problem in these pharmacological approaches is that all of the candidate drugs had potential deleterious side effects on non-target tissue. In fact, the development of pharmaceutical agents for traumatic brain injury has all but ceased with increasing reluctance of the pharmaceutical industry to sponsor the testing of new candidate therapies as uncertainty remains regarding benefit.

Given the absence of treatment options for head trauma, there is a need for a therapy that can target and reduce secondary physiological responses such as inflammation, swelling, and intracranial pressure while also promoting repair and regrowth in and around the injured area. While EMF treatments have been explored for a variety of uses, the possible benefits of PEMF in treating or preventing neurological injury and degenerative conditions such as TBI, subarachnoid hemorrhage, brain ischemia, stroke, and Alzheimer's or Parkinson's Disease are relatively unknown. This is in part due to the fact that the secondary physiological responses (e.g. inflammatory) in the central nervous system (CNS) differ from that of the periphery systems for which PEMF is currently used. Moreover, attention has been focused on pharmaceutical treatments until recently. Accordingly, embodiments of the present invention address this need and provide methods and devices using PEMF to treat patients suffering from neurological injury (such as traumatic brain injury) and secondary physiological responses arising from that injury.

Transient elevations in cytosolic $Ca^{2+}$, from external stimuli as simple as changes in temperature and receptor activation, or as complex as mechanical disruption of tissue, will activate CaM. Once $Ca^{2+}$ ions are bound, a conformational change will allow CaM bind to and activate a number of key enzymes involved in cell viability and function, such as the endothelial and neuronal constitutive nitric oxide synthases (cNOS); eNOS and nNOS, respectively. As a consequence, NO is rapidly produced, albeit in lower concentrations than the explosive increases in NO produced by inducible NOS (iNOS), during the inflammatory response. In contrast, these smaller, transient increases in NO produced by Ca/CaM-binding will activate soluble guanylyl cyclase (sGC), which will catalyze the formation of cyclic guanosine monophosphate (cGMP). The CaM/NO/cGMP signaling pathway can rapidly modulate blood flow in response to normal physiologic demands, as well as to inflammation. Importantly, this same pathway will also rapidly attenuate expression of cytokines such as interleukin-1beta (IL-1β), and iNOS and stimulate anti-apoptotic pathways in neurons. All of these effects are mediated by calcium and cyclic nucleotides, which in turn regulate growth factors such as basic fibroblast growth factor (FGF-2) and vascular endothelial growth factor (VEGF), resulting in pleiotrophic effects on cells involved in tissue repair and maintenance.

In general, inflammatory response in the brain differs from that in other organs. It is exemplified by a more modest and delayed recruitment of leukocytes into the brain than into peripheral organs. Brain microglia, in contrast, are activated and release inflammatory mediators beginning within minutes to hours after TBI. The mediators often express neurotoxic and neuroprotective properties. For example, cytokines may either promote damage or support recovery processes; in some cases, cytokines, such as interleukin-6, may perform both functions.

This invention teaches that rapid intervention after traumatic head, cerebral and neural injury with electromagnetic fields configured to rapidly modulate the biochemical signaling cascades animals and humans employ in response to physical and chemical perturbations will significantly reduce the pathological consequences of such injuries, thereby reducing morbidity and the cost of health care.

Bone growth stimulator (hereinafter known as BGS) electromagnetic fields are now part of the standard armamentarium of orthopedic practice worldwide for the treatment of recalcitrant bone fractures. Radio frequency signals, originally developed for deep tissue heating (diathermy), were shown to produce biological effects when applied at non-thermal levels using pulse-modulation techniques to produce pulsed radio frequency (hereinafter known as PRF) signals, which is a subset frequency band within PEMF. At the cellular level, numerous studies demonstrate that BGS, PRF and other electromagnetic field (hereinafter known as EMF) signals modulate the release of growth factors and cytokines.

Stimulation of transforming growth factor beta ("TGF-b") messenger RNA ("mRNA") with EMF in a bone induction model in a rat has been shown. Studies have also demonstrated upregulation of TGF-b mRNA by PEMF in human osteoblast-like cell line designated MG-63, wherein there were increases in TGF-b1, collagen, and osteocalcin synthesis. EMF stimulated an increase in TGF-b1 in both hypertrophic and atrophic cells from human non-union tissue. Further studies demonstrated an increase in both TGF-b1 mRNA and protein in osteoblast cultures resulting from a direct effect of EMF on a calcium/calmodulin-dependent pathway. Cartilage cell studies have shown similar increases in TGF-b1 mRNA and protein synthesis from EMF, demonstrating a therapeutic application to joint repair.

However, prior art in this field has not produced electromagnetic signals configured specifically to instantaneously accelerate the asymmetrical kinetics of the binding of intracellular ions to their associated buffers which regulate the biochemical signaling pathways living systems employ in response to brain tissue ischemia from stroke, traumatic brain injury, head injury, cerebral injury, neurological injury and neurodegenerative diseases. The result is that there are no devices currently in use for clinical applications of electromagnetic fields for the treatment of brain tissue ischemia from stroke, traumatic brain injury, head injury, cerebral injury, neurological injury and neurodegenerative diseases.

Therefore, a need exists for an apparatus and a method that modulates the biochemical pathways that regulate animal and human tissue response to brain tissue ischemia from stroke, traumatic brain injury, head injury, cerebral injury, neurological injury and neurodegenerative diseases by configuring EMF signals specifically to accelerate the asymmetrical kinetics of ion binding to intracellular buffers which regulate the relevant biochemical signaling pathways. Some embodiments provide for a method that employs electromagnetic fields for rapid treatment of brain tissue ischemia from stroke, traumatic brain injury, head injury, cerebral injury, neurological injury and neurodegenerative diseases. In another embodiment, an apparatus incorporates miniaturized circuitry and light weight coil applicators or electrodes thus allowing the apparatus to be low cost, portable and, if desired, disposable. A further need exists for an apparatus and method that incorporates the asymmetrical kinetics of ion binding to intracellular buffers to configure electromagnetic waveforms to increase the rate of ion binding and enhance the biochemical signaling pathways living systems employ in response to brain tissue ischemia from stroke, traumatic brain injury, head injury, cerebral injury, neurological injury and neurodegenerative diseases, and incorporates miniaturized circuitry and light weight applicators that can be constructed to be implantable.

SUMMARY OF THE DISCLOSURE

Described herein are devices, systems and methods for delivering electromagnetic signals and fields configured specifically to accelerate the asymmetrical kinetics of the binding of intracellular ions to their respective intracellular buffers, to enhance the biochemical signaling pathways animals and humans employ to respond to brain tissue ischemia from stroke, traumatic brain injury, head injury, cerebral injury, neurological injury and neurodegenerative diseases.

One variation according to the present invention utilizes a repetitive burst of arbitrary non-thermal EMF waveforms configured to maximize the bound concentration of intracellular ions at their associated molecular buffers to enhance the biochemical signaling pathways living systems employ in response to brain tissue ischemia from stroke, traumatic brain injury, head injury, cerebral injury, neurological injury and neurodegenerative diseases. Non-thermal electromagnetic waveforms are selected first by choosing the ion and the intracellular binding protein, for example $Ca^{2+}$ and CaM, among the many ion-buffer combinations within the living cell, which determines the frequency range within which the signal must have non-thermal frequency components of sufficient, but non-destructive, amplitude to accelerate the kinetics of ion binding. Signals comprise a pulse duration, random signal duration or carrier period which is less than half of the ion bound time to increase the voltage in the target pathway so as to maximally accelerate ion binding to maximally modulate biochemical signaling pathways to enhance specific cellular and tissue responses to brain tissue ischemia from stroke, traumatic brain injury, head injury, cerebral injury, neurological injury and neurodegenerative diseases.

In some variations, signals comprise bursts of at least one of sinusoidal, rectangular, chaotic or random EMF wave shapes; have burst duration less than about 100 msec, with frequency content less than about 100 MHz, repeating at less than about 1000 bursts per second. Peak signal amplitude in the ion-buffer binding pathway is less than about 1000 V/m. Another embodiment comprises about a 1 to about a 50 millisecond burst of radio frequency sinusoidal waves in the range of about 1 to about 100 MHz, incorporating radio frequencies in the industrial, scientific and medical (hereinafter known as ISM) band, for example 27.12 MHz, but it may be 6.78 MHz, 13.56 MHz or 40.68 MHz in the short wave frequency band, repeating between about 0.1 and about 10 bursts/sec. Such waveforms can be delivered via inductive coupling with a coil applicator or via capacitive coupling with electrodes in electrochemical contact with the conductive outer surface of the target.

Some embodiments described provide for a waveform configuration that accelerates the kinetics of $Ca^{2+}$ binding to CaM, consisting of about a 1 to about a 10 msec burst of between about 5 MHz to about 50 MHz in the ISM band, repeating between about 1 and about 5 bursts/sec and inducing a peak electric field between about 1 and about 100 V/m, then coupling the configured waveform using a generating device such as ultra lightweight wire or printed circuit coils that are powered by a waveform configuration device such as miniaturized electronic circuitry.

Other embodiments described provide for a waveform configuration that accelerates the kinetics of $Ca^{2+}$ binding to CaM, consisting of about a 1 to about a 10 msec burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire, printed circuit coils or conductive garments that are powered by a waveform configuration device such as miniaturized electronic circuitry which is programmed to apply the aforementioned waveform at fixed or variable intervals, for example for 1 minute every 10 minutes, or for 10 minutes every hour, or for any other regimen found to be beneficial for a prescribed treatment. Further embodiments provide for methods and devices for applying electromagnetic waveforms to animals and humans that accelerate the asymmetrical kinetics of the binding of intracellular ions to their associated intracellular buffers, by configuring the waveforms to contain repetitive frequency components of sufficient amplitude to maximize the bound concentration of the intracellular ion to its associated intracellular buffer, thereby to enhance the biochemical signaling pathways living tissue employ in response to brain tissue ischemia from stroke, traumatic brain injury, head injury, cerebral injury, neurological injury and neurodegenerative diseases.

Additional embodiments provide for methods and devices for applying electromagnetic waveforms to animals and humans which match the asymmetrical kinetics of the binding of $Ca^{2+}$ to CaM by configuring the waveforms to contain repetitive frequency components of sufficient amplitude to accelerate and increase the binding of $Ca^{2+}$ to CaM, thereby enhancing the CaM-dependent nitric oxide (NO)/cyclic guanosine monophosphate (cGMP) signaling pathway.

Further embodiments provide for electromagnetic waveform configurations to contain repetitive frequency components of sufficient amplitude to accelerate and increase the binding of $Ca^{2+}$ to CaM, thereby enhancing the CaM-dependent NO/cGMP signaling pathway to accelerate blood and lymph vessel dilation for relief of post-operative and post traumatic pain and edema.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to enhance angiogenesis and microvascularization for hard and soft tissue repair.

A further aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to accelerate deoxyribonucleic acid (hereinafter known as DNA) synthesis by living cells.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway to modulate growth factor release, such as basic fibroblast growth factor (bFGF), vascular endothelial growth factor (VGEF), bone morphogenic protein (BMP), or any other growth factor production by living cells.

It is yet another aspect of the present invention to configure electromagnetic waveforms to contain repetitive frequency components of sufficient amplitude to accelerate and increase the binding of $Ca^{2+}$ to CaM, thereby enhancing the CaM-dependent NO/cGMP signaling pathway to modulate growth factor release, such as basic fibroblast growth factor (bFGF), vascular endothelial growth factor (VGEF), bone morphogenic protein (BMP), or any other growth factor production by living cells employ in response to brain tissue ischemia from stroke, traumatic brain injury, head injury, cerebral injury, neurological injury and neurodegenerative diseases Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells in response to brain tissue ischemia from stroke, traumatic brain injury, head injury, cerebral injury, neurological injury and neurodegenerative diseases.

Another aspect of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to accelerate the production of extracellular proteins for tissue repair and maintenance.

It is another aspect of the present invention to configure electromagnetic waveforms to contain repetitive frequency components of sufficient amplitude to accelerate and increase the binding of $Ca^{2+}$ to CaM, thereby enhancing the CaM-dependent NO/cyclic adenosine monophosphate (cAMP) signaling pathway, or any other signaling pathway, to modulate cell and tissue differentiation.

It is yet another aspect of the present invention to configure electromagnetic waveforms to contain repetitive frequency components of sufficient amplitude to accelerate and increase the binding of $Ca^{2+}$ to CaM, thereby enhancing the CaM-dependent NO/cAMP signaling pathway, or any other signaling pathway, to prevent or reverse neurodegeneration.

Another aspect of the present invention is to configure electromagnetic waveforms to contain frequency components of sufficient amplitude to accelerate the binding of $Ca^{2+}$ to CaM, thereby enhancing the CaM-dependent NO/cGMP signaling pathway to modulate heat shock protein release from living cells.

Yet another aspect of the invention provides for a method for treating a neurological injury or condition in a patient in need thereof including the steps of generating a pulsed electromagnetic field from a pulsed electromagnetic field source and applying the pulsed electromagnetic field in proximity to a target region affected by the neurological injury or condition to reduce a physiological response to the neurological injury or condition. Optionally, in any of the preceding embodiments, the physiological response can be inflammation and/or increased intracranial pressure.

Optionally, in any of the preceding embodiments, the method may also include monitoring the physiological response and continuing to apply the pulsed electromagenetic field until an acceptable level of the physiological response is reached. Optionally, in any of the preceding embodiments, the physiological response can be increased intracranial pressure and the acceptable level is below about 20 mmHg.

In further variations, the method may include a pulsed electromagnetic field comprising a 2 msec burst of 27.12 MHz sinusoidal waves repeating at 2 Hz. In other variations, the method may include a pulsed electromagnetic field comprising a 3 msec burst of 27.12 MHz sinusoidal waves repeating at 2 Hz. In further embodiments, the pulsed electromagnetic field may comprise a 4 msec burst of 27.12 MHz sinusoidal waves repeating at 2 Hz.

A further aspect of the invention provides for a method for treating a neurological injury or condition in a patient in need thereof where the method includes generating a first pulsed electromagnetic field from a pulsed electromagnetic field source; applying the first pulsed electromagnetic field in proximity to a target region affected by the neurological injury or condition to reduce a physiological response to the neurological injury or condition for a first treatment interval; discontinuing the application of the first pulsed electromagnetic field for an inter-treatment period greater than zero; and applying a second pulsed electromagnetic field in proximity to the target region. Optionally, in any of the preceding embodiments, the first and second pulsed electromagnetic fields are substantially the same.

Optionally, in any of the preceding embodiments, the method may include monitoring the physiological response; and modifying the first pulsed electromagnetic field to the second pulsed electromagnetic field in response to the monitoring step.

Moreover, optionally, in any of the preceding embodiments, the method may also include monitoring the physiological response; and discontinuing treatment once an acceptable level of the physiological response is reached.

Optionally, in any of the preceding embodiments, the method may also include attenuating inflammatory cytokines and growth factors at the target region by applying the first pulsed electromagnetic field or the second pulsed electromagnetic field to the target region.

Optionally, in any of the preceding embodiments, the method may also include accelerating the healing of the target region by applying the first pulsed electromagnetic field or the second pulsed electromagnetic field to the target region.

Furthermore, in other embodiments, applying the first pulsed electromagnetic field in proximity to a target region affected by the neurological injury or condition to reduce a physiological response may comprise reducing a concentration of IL-1β. In further embodiments, the neurological injury or condition may be a neurodegenerative disease.

In further embodiments, the neurological injury or condition is TBI.

Another aspect of the invention provides for a method for treating a neurological injury or condition in a patient in need thereof, the method including generating a pulsed electromagnetic field from a pulsed electromagnetic field source; and applying the pulsed electromagnetic field in proximity to a target brain region affected by the neurological injury or condition to reduce a physiological response to the neurological injury or condition by modulating microglia activation in the target brain region. In some embodiments, modulating microglia activation includes reducing microglia activation in the target brain region.

Another aspect of the invention provides for a method of promoting neurological repair or growth following a neurological injury or condition including placing a treatment coil of a self-contained, lightweight, and portable treatment apparatus externally to a target treatment site in need of repair or development, wherein the treatment apparatus comprises a conformable coil having one or more turns of wire and a control circuit; generating an electromagnetic field using the treatment coil; delivering the electromagnetic field to the target treatment site using the treatment coil; and reducing a physiological response to the neurological injury or condition.

Optionally, in any of the preceding embodiments, generating an electromagnetic field comprises generating at least one burst of sinusoidal, rectangular, chaotic, or random waveforms, having a frequency content in a range of about 0.01 Hz to about 10,000 MHz at about 1 to about 100,000 bursts per second, having a burst duration from about 0.01 to about 1000 bursts per second, and having a burst repetition rate from about 0.01 to about 1000 bursts/second.

Generating an electromagnetic field may comprise generating at least one burst of sinusoidal, rectangular, chaotic, or random waveforms, having a frequency content in a range of about 0.01 Hz to about 10,000 MHz, having a burst duration from about 0.1 to about 100 msec, at a peak amplitude of 0.001 G to about 0.1 G, and having a burst repetition rate from about 0.01 to about 100 bursts/second.

Optionally, in any of the preceding embodiments, the method may also include delivering the electromagnetic field for a period of about 1 minute to about 240 minutes.

Optionally, in any of the preceding embodiments, the physiological response can be a cognitive deficiency.

Optionally, in any of the preceding embodiments, the pulsed electromagnetic field comprises about a 1 msec to about a 10 msec burst of 27.12 MHz sinusoidal waves repeating at about 1 Hz to about 10 Hz.

Optionally, in any of the preceding embodiments, the pulsed electromagnetic field comprises an ISM carrier frequency modulated at about a 1 msec to about a 10 msec burst repeating at about 1 Hz to about 10 Hz.

Optionally, in any of the preceding embodiments, the pulsed electromagnetic field comprises an ISM carrier or any other radio frequency up to 10,000 GHz, configured to modulate a rhythm of a physiological system.

Optionally, in any of the preceding embodiments, the physiological system is the central nervous system. Moreover, optionally, in any of the preceding embodiments, the physiological system is the peripheral nervous system. Additionally, optionally, in any of the preceding embodiments, the physiological system is the cardiac system.

Optionally, in any of the preceding embodiments, the physiological system is the pulmonary system.

Optionally, in any of the preceding embodiments, the pulsed electromagnetic field comprises an ISM carrier or any other radio frequency up to 10,000 GHz, configured to modulate a rhythm of a physiological process Optionally, in any of the preceding embodiments, the pulsed electromagnetic field comprises an ISM carrier or any other radio frequency up to 10,000 GHz, configured to modulate a rhythm of a brain.

Optionally, in any of the preceding embodiments, the pulsed electromagnetic field comprises an ISM carrier or any other radio frequency up to 10,000 GHz, configured to modulate a circadian rhythm.

Optionally, in any of the preceding embodiments, the pulsed electromagnetic field comprises an ISM carrier frequency configured to modulate quality of sleep.

Optionally, in any of the preceding embodiments, the pulsed electromagnetic field is configured to modulate calmodulin-dependent signaling in a biological system.

Optionally, in any of the preceding embodiments, the electromagnetic field comprises a waveform that produces an effect upon calmodulin-dependent signaling in a biological system.

Optionally, in any of the preceding embodiments, the electromagnetic field comprises a waveform that modulates at least one biological signaling pathway.

Optionally, in any of the preceding embodiments, the method may also include increasing a growth factor in the target region.

Optionally, in any of the preceding embodiments, increasing a growth factor in the target region enhances angiogenesis.

Optionally, in any of the preceding embodiments, increasing a growth factor in the target region enhances nervous tissue regeneration.

Optionally, in any of the preceding embodiments, the growth factor is selected from the group consisting of FGF-2, VEGF, and BMP.

Optionally, in any of the preceding embodiments, the pulsed electromagnetic field comprises an ISM carrier or any other radio frequency up to 10,000 GHz, configured to modulate a sleep pattern.

Optionally, in any of the preceding embodiments, the pulsed electromagnetic field comprises an ISM carrier or any other radio frequency up to 10,000 GHz, configured to modulate slow-wave sleep in a sleep cycle to effect the production of human growth hormone. The above and yet other embodiments and advantages of the present invention will become apparent from the hereinafter set forth Brief Description of the Drawings and Detailed Description of the Invention.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
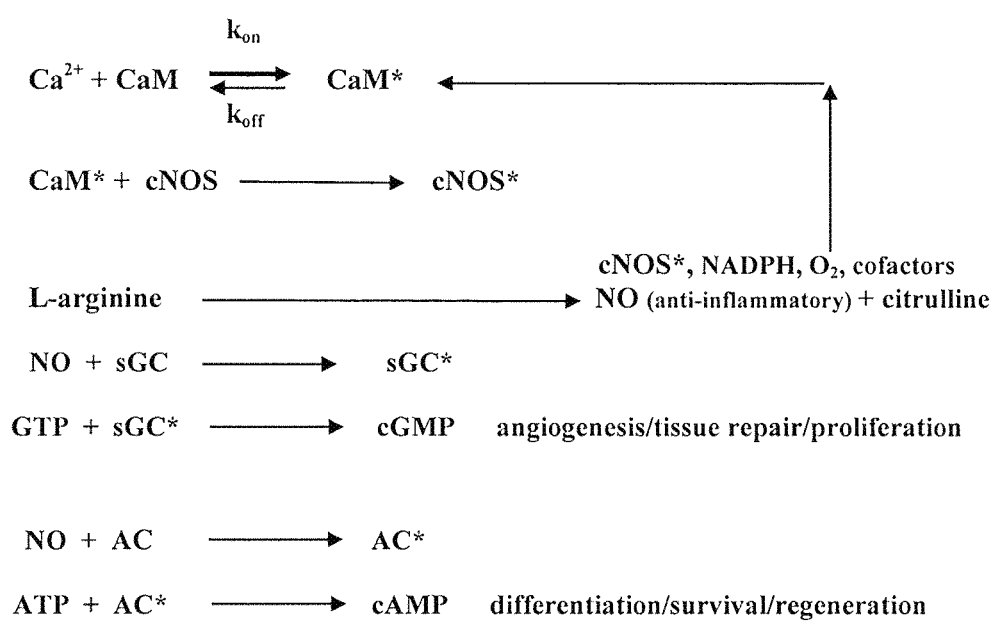
FIG. 1A is a schematic representation of the biological EMF transduction pathway which is a representative target pathway of EMF signals configured according to embodiments described.

Basal levels of intracellular $Ca^{2+}$ are typically 50-100 nM, tightly maintained by a number of physiological calcium buffers. It is generally accepted that transient elevations in cytosolic $Ca^{2+}$ from external stimuli as simple as changes in temperature and mechanical forces, or as complex as mechanical disruption of tissue, rapidly activate CaM, which equally rapidly activates the cNOS enzymes, i.e., endothelial and neuronal NOS, or eNOS and nNOS, respectively. Studies have shown that both isoforms are inactive at basal intracellular levels of $Ca^{2+}$, however, their activity increases with elevated $Ca^{2+}$, reaching half-maximal activity at about 300 nM. Thus, nNOS and eNOS are regulated by changes in intracellular $Ca^{2+}$ concentrations within the physiological range. In contrast, a third, inducible isoform of NOS (iNOS), which is upregulated during inflammation by macrophages and/or neutrophils, contains CaM that is tightly bound, even at low resting levels of cytosolic $Ca^{2+}$, and is not sensitive to intracellular $Ca^{2+}$.

Once cNOS is activated by CaM it converts its substrate, L-arginine, to citrulline, releasing one molecule of NO. As a gaseous free radical with a half-life of about 5 sec, NO diffuses locally through membranes and organelles and acts on molecular targets at a distance up to about 200 μm. The low transient concentrations of NO from cNOS can activate soluble guanylyl cyclase (sGC), which catalyzes the synthesis of cyclic guanosine monophosphate (cGMP). The CaM/NO/cGMP signaling pathway is a rapid response cascade which can modulate peripheral and cardiac blood flow in response to normal physiologic demands, as well as to inflammation. This same pathway also modulates the release of cytokines, such as interleukin-1beta (IL-1β) and growth factors such as basic fibroblast growth factor (FGF-2) and vascular endothelial growth factor (VEGF) which have pleiotropic effects on cells involved in tissue repair and maintenance.

Following an injury, e.g., a bone fracture, torn rotator cuff, sprain, strain or surgical incision, repair commences with an inflammatory stage during which the pro-inflammatory cytokine IL-1β is rapidly released. This, in turn, up-regulates iNOS, resulting in the production of large amounts of NO in the wound bed. Continued exposure to NO leads to the induction of cyclooxygenase-2 and increased synthesis of prostaglandins which also play a role in the inflammatory phase. While this process is a natural component of healing, when protracted, it can lead to increased pain and delayed or abnormal healing. In contrast, CaM/eNOS/NO signaling has been shown to attenuate levels of IL-1β and down-regulate iNOS. As tissue further responds to injury, the CaM/NO/cGMP cascade is activated in endothelial cells to stimulate angiogenesis, without which new tissue growth cannot be sustained. Evidence that non-thermal EMF can modulate this cascade is provided by several studies. An early study showed that the original BGS signal promoted the creation of tubular, vessel-like, structures from endothelial cells in culture in the presence of growth factors. Another study using the same BGS signal confirmed a seven-fold increase in endothelial cell tubularization in vitro. Quantification of angiogenic proteins demonstrated a five-fold increase in FGF-2, suggesting that the same BGS signal stimulates angiogenesis by increasing FGF-2 production. This same study also reported increased vascular in-growth more than two-fold when applied to an implanted Matrigel plug in mice, with a concomitant increase in FGF-2, similar to that observed in vitro. The BGS signal significantly increased neovascularization and wound repair in normal mice, and particularly in diabetic mice, through an endogenous increase in FGF-2, which could be eliminated by using a FGF-2 inhibitor.

Similarly, a pulse modulated radio frequency (PRF) signal of the type used clinically for wound repair was reported to significantly accelerate vascular sprouting from an arterial loop transferred from the hind limb to the groin in a rat model. This study was extended to examine free flap survival on the newly produced vascular bed. Results showed 95% survival of PRF-treated flaps compared to 11% survival in the sham-treated flaps, suggesting a significant clinical application for PRF signals in reconstructive surgery.

In some embodiments, the proposed EMF transduction pathway relevant to tissue maintenance, repair and regeneration, begins with voltage-dependent $Ca^{2+}$ binding to CaM, which is favored when cytosolic $Ca^{2+}$ homeostasis is disrupted by chemical and/or physical insults at the cellular level. Ca/CaM binding produces activated CaM that binds to, and activates, cNOS, which catalyzes the synthesis of the signaling molecule NO from L-arginine. This pathway is shown in its simplest schematic form in FIG. 1A.

As shown in FIG. 1A, cNOS* represents activated constitutive nitric oxide synthase (cNOS), which catalyzes the production of NO from L-arginine. The term "sGC*" refers to activated guanylyl cyclase which catalyzes cyclic guanosine monophosphate (cGMP) formation when NO signaling modulates the tissue repair pathway. "AC*" refers to activated adenylyl cyclase, which catalyzes cyclic adenosine monophosphate (cAMP) when NO signaling modulates differentiation and survival.

According to some embodiments, an EMF signal can be configured to accelerate cytosolic ion binding to a cytosolic buffer, such as $Ca^{2+}$ binding to CaM, because the rate constant for binding, $k_{on}$ is voltage-dependent and $k_{on}$ is much greater than the rate constant for unbinding, $k_{off}$, imparting rectifier-like properties to ion-buffer binding, such as $Ca^{2+}$ binding to CaM.

For example, EMF can accelerate the kinetics of $Ca^{2+}$ binding to CaM, the first step of a well characterized cascade that responds to chemical or physical insults. Ca/CaM binding is kinetically asymmetrical, i.e., the rate of binding exceeds the rate of dissociation by several orders of magnitude ($k_{on} \gg k_{off}$), driving the reaction in the forward direction. Ca/CaM binding has been well characterized, with the binding time constant reported to be in the range of $10^{-2}$-$10^{-3}$ sec. In contrast, release of $Ca^{2+}$ from CaM cannot occur until cNOS* has converted L-arginine to citrulline and NO, which takes the better part of a second. Subsequent reactions involving NO depend upon the cell/tissue state. For example, tissue repair requires a temporal sequence of inflammatory, anti-inflammatory, angiogenic and proliferative components. Endothelial cells orchestrate the production of FGF-2 and VEGF for angiogenesis. For each of these phases, early NO production by endothelial cells, leading to increased cGMP by these, as well as other NO targets, such as vascular smooth muscle, would be expected to be modulated by an EMF effect on sGC via Ca/CaM binding. In contrast, nerve or bone regeneration may require other pathways leading to differentiation during development and growth, and prevention of apoptosis, as in response to injury or neurodegenerative diseases. For these cases, early cyclic adenosine monophosphate (cAMP) formation would be modulated by an EMF effect on sAC via Ca/CaM binding.

The substantial asymmetry of Ca/CaM binding kinetics provides a unique opportunity to configure EMF signals that selectively modulate $k_{on}$. In general, if $k_{on} \gg k_{off}$ and $k_{on}$ is voltage-dependent, according to the present invention, ion binding could be increased with an exogenous electric field signal having a carrier period or pulse duration that is significantly shorter than the mean lifetime of the bound ion. This applies to the CaM signaling pathway, causing it to exhibit rectifier-like properties, i.e., to yield a net increase in the population of bound $Ca^{2+}$ because the forward (binding) reaction is favored. The change in surface concentration, $\Delta\Gamma$, of $Ca^{2+}$ at CaM is equal to the net increase in the number of ions that exit the outer Helmholtz plane, penetrate the water dipole layer at the aqueous interface of the binding site, and become bound in the inner Helmoltz plane. For the general case of ion binding, evaluation of Ca/CaM binding impedance, ZA(s), allows calculation of the efficacy of any given waveform in that pathway by evaluating the frequency range over which the forward binding reaction can be accelerated. Thus, binding current, IA(t), is proportional to the change in surface charge (bound ion concentration) via dq(t)/dt, or, in the frequency domain, via $sq_A(s)$. IA(s) is, thus, given by:

$$I_A(s) = sq_A(s) = s\Gamma_o f(\Delta\Gamma(s)) \quad (1)$$

where s is the real-valued frequency variable of the Laplace transform. Taking the first term of the Taylor expansion of equation 1 gives:

$$I_A(s) = q_\Gamma s \Gamma_o \Delta\Gamma(s) \quad (2)$$

where $q\Gamma = \partial q/\partial\Gamma$, a coefficient representing the dependence of surface charge on bound ion concentration. $\Delta\Gamma(s)$ is a function of the applied voltage waveform, E(s), and, referring to the reaction scheme in FIG. 1, of the change in concentration of eNOS*, defined as $\Delta\Phi(s)$:

$$\Delta\Gamma(s) = k_{on}/\Gamma_o s[-\Delta\Gamma(s) + aE(s) + \Delta\Phi(s)] \quad (3)$$

where $\Gamma_o$ is the initial surface concentration of $Ca^{2+}$ (homeostasis), and $a = \partial\Gamma/\partial E$, representing the voltage dependence of $Ca^{2+}$ binding. Referring to the reaction scheme in FIG. 1, it may also be seen that eNOS* depends only upon $Ca^{2+}$ binding, i.e., $\Delta\Gamma(s)$. Thus:

$$\Delta\Phi(s) = \upsilon_\Phi/\Phi_o s[-\Delta\Phi(s) - \Delta\Gamma(s)] \quad (4)$$

where $\upsilon\Phi$ is the rate constant for Ca/CaM binding to eNOS and $\Phi_o$ is the initial concentration of eNOS* (homeostasis).

Using equations 2, 3 and 4, and for $k_{on} \gg \upsilon_\Phi$, ZA(s) may be written:

$$Z_A(s) = \frac{E(s)}{I_A(s)} = \frac{1}{q_\Gamma a}\left[\frac{1 + \Gamma_o s/k_{on}}{\Gamma_o s}\right] \quad (5)$$

Equation 5 describes the overall frequency response of the first binding step in a multistep ion binding process at an electrified interface, wherein the second step requires that the bound ion remain bound for a period of time significantly longer than the initial binding step. For this case, the first ion binding step is represented by an equivalent electrical impedance which is functionally equivalent to that of a series $R_A$-$C_A$ electric circuit, embedded in the overall dielectric properties of the target. $R_A$ is inversely proportional to the binding rate constant ($k_{on}$), and $C_A$ is directly proportional to bound ion concentration.

Some embodiments provide that a electromagnetic field, for which pulse duration or carrier period is less than about half of the bound ion lifetime can be configured to maximize current flow into the capacitance CA, which will increase the voltage, $E_b(s)$, where s is the LaPlace frequency, across CA. $E_b(s)$ is a measure of the increase in the surface concentration of the binding ion in the binding sites of the buffer, above that which occurs naturally in response to a given physiological state. The result is an increase in the rate of biochemical signaling in plant, animal and human repair, growth and maintenance pathways which results in the acceleration of the normal physiological response to chemical or physical stimuli. The following equation demonstrates the relation between the configured electromagnetic waveform, E(s) and $E_b(s)$.

$$E_b(s) = \frac{(1/sC_A)E(s)}{(R_A^2 + (1/sC_A)^2)^{1/2}} \quad (6)$$

Some embodiments also provide that a time-varying electromagnetic field for which pulse duration or carrier period is less than about half of the bound ion lifetime of $Ca^{2+}$ binding to CaM will maximize the current flow into the Ca/CaM binding pathway to accelerate the CaM-dependent signaling which plants, animals and humans utilize for tissue growth, repair and maintenance. In particular, a time-varying electromagnetic field may be configured to modulate CaM-dependent NO/cGMP signaling which accelerates; pain and edema relief, angiogenesis, hard and soft tissue repair, repair of ischemic tissue, prevention and repair of neurodegenerative diseases, nerve repair and regeneration, skeletal and cardiac muscle repair and regeneration, relief of muscle pain, relief of nerve pain, relief of angina, relief of degenerative joint disease pain, healing of degenerative joint disease, immunological response to disease, including cancer.

Another embodiment according to the present invention is an electromagnetic signal which accelerates the kinetics of $Ca^{2+}$ binding by maximizing non-thermal $E_b(s)$ at its CaM binding sites, consisting of a 1-10 msec pulse burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire coils that are powered by a waveform configuration device such as miniaturized electronic circuitry which is programmed to apply the waveform at fixed or variable intervals, for example 1 minute every 10 minutes, 10 minutes every hour, or any other regimen found to be beneficial for a prescribed treatment.

Figure 10A:
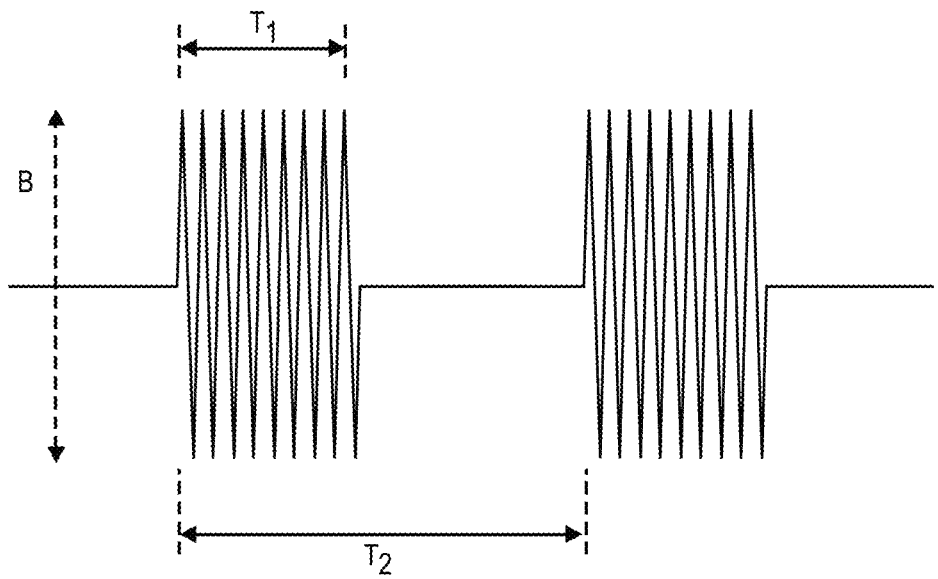
FIGS. 10A and 10B illustrate PEMF signal configurations according to some embodiments described.
Figure 10B:
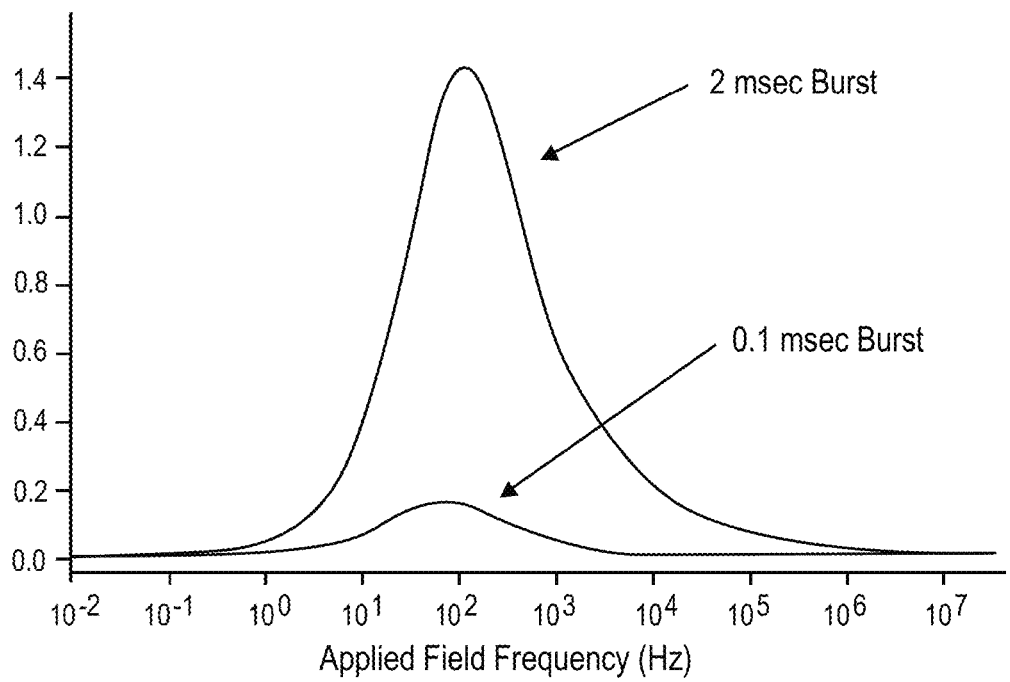

In some embodiments, the PEMF signal configuration used may be a sinusoidal wave at 27.12 MHz with peak magnetic field B=0.05 G (Earth=0.5 G), burst width, T1=5 msec, and repetition rate T2=2/sec as shown in FIG. 10A. The PEMF signal configuration may also induce a 1-5 V/m peak electric field in situ with a duty cycle=2%, without heat or excitable membrane activity produced. The field may be applied through an electrical pulse generator to a coil tuned to 27.12 MHz. The burst width and repetition rate may be chosen by comparing the voltage induced across the $Ca^{2+}$ binding site over a broad frequency range to noise fluctuations over the same range. Effects of burst widths of two 27.12 MHz sinusoidal signals at 1 Hz are illustrated in FIG. 10B. As shown in FIG. 10B, high signal-to-noise ratios (SNRs) can be achieved in the relatively low frequency range and at peak magnetic field 0.05 G.

Figure 2A:
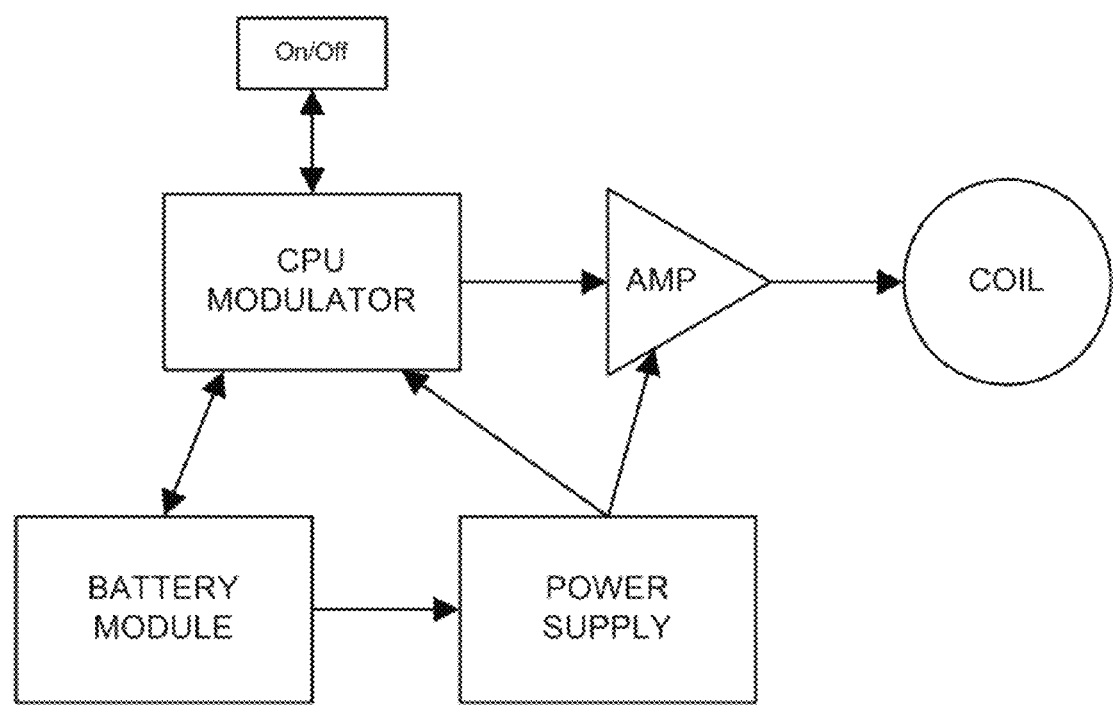
FIG. 2A is a block diagram of miniaturized circuitry for use with a coil applicator according to some embodiments described.

FIG. 2A illustrates a block diagram of an EMF delivery apparatus as described according to some embodiments. As shown in FIG. 2A, the apparatus may have miniaturized circuitry for use with a coil applicator. In some embodiments, the apparatus may include a CPU MODULATOR, a BATTERY MODULE, a POWER SUPPLY, On/Off switch, and an output amplifier, AMP, as illustrated. In further variations, the CPU MODULATOR may be an 8 bit 4 MHz micro-controller; however, other suitable bit-MHz combination micro-controllers may be used as well. For example, in some embodiments, the CPU MODULATOR may be programmed for a given carrier frequency or pulse duration, such as about 27.12 MHz sinusoidal wave. Moreover, the CPU MODULATOR may be programmed for a given burst duration, for example about 3 msec. In further variations, the CPU MODULATOR may be programmed to provide a given in situ peak electric field, for example 20 V/m; or a given treatment time, for example about 15 minutes; and/or a given treatment regimen, for example about 10 minutes about every hour. The CPU MODULATOR may also be programmed to deliver an EMF waveform to the target ion binding pathway.

In further embodiments, the BATTERY MODULE may be rechargeable. In other embodiments, the BATTERY MODULE has an output voltage of 3.3 V; however, other voltages can be used as is understood in the art. In further variations, the BATTERY MODULE supplies DC voltage and current to a POWER SUPPLY which provides operating power to the CPU MODULATOR and the output amplifier AMP.

In some variations, the electromagnetic signal (or a field generated from a electromagnetic signal) is applied inductively to the plant animal or human target with a COIL applicator, or capacitively with electrodes in electrochemical contact with the out conductive surface of the target structure (not shown). In some variations, the COIL applicator is flexible and circular, but may also be anatomically conformable, such as oval or saddle shaped, with a diameter of between about 2 cm to about 50 cm. An electromagnetic treatment, or, if desired, an electromagnetic treatment regimen, can be initiated with the ON/OFF switch, which may be mechanical or electronic.

Figure 2B:
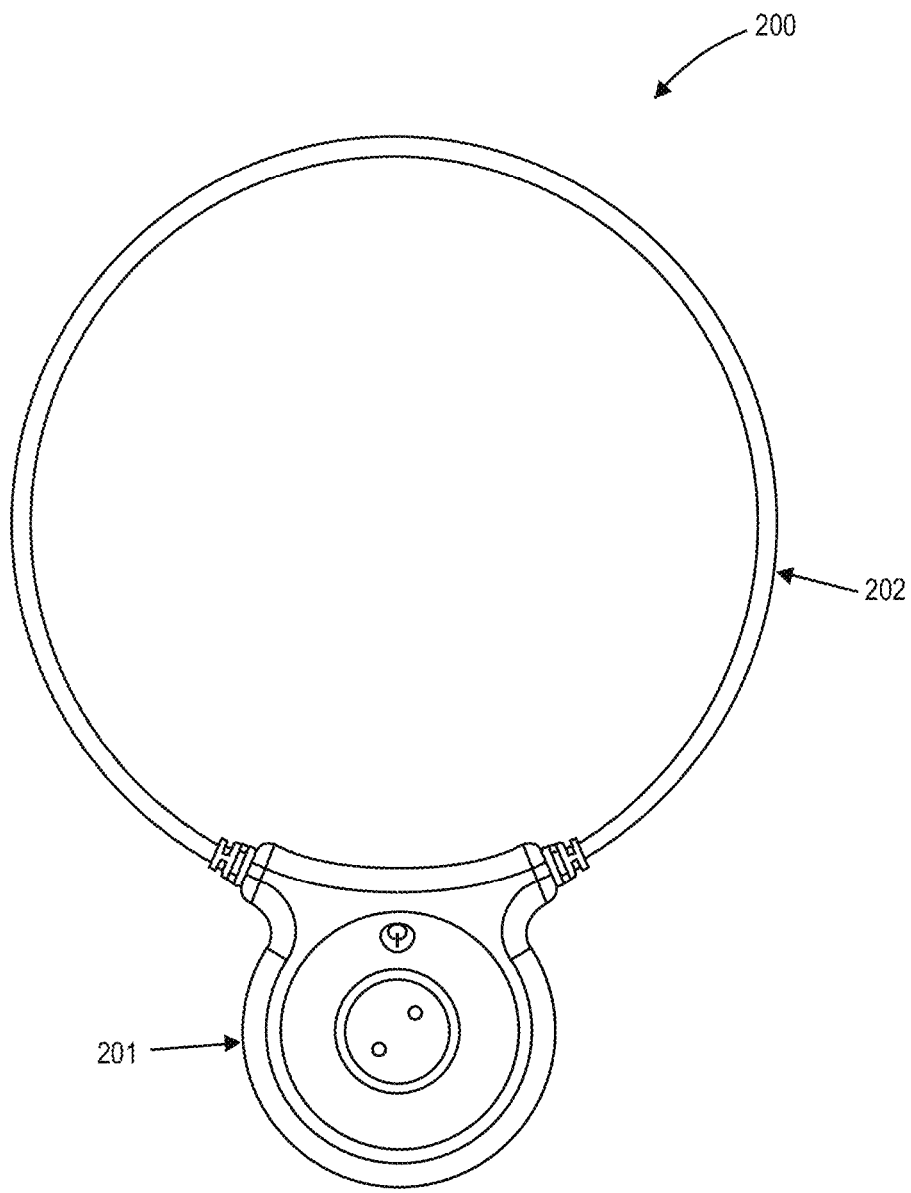
FIG. 2B illustrates a device for application of electromagnetic signals according to an embodiment of the devices and methods described herein.

Some embodiments combine the signal generation and coil or electrode applicator into one portable or disposable unit, such as illustrated in FIG. 2B (which will be described in greater detail below) for the case of an inductively coupled signal. In some variations, when electrical coils are used as the applicator, the electrical coils can be powered with a time varying magnetic field that induces a time varying electric field in a target pathway structure according to Faraday's law. An electromagnetic field generated by a circuit such as shown in FIG. 2A can also be applied using electrochemical coupling, wherein electrodes are in direct contact with skin or another outer electrochemically conductive boundary of a target pathway structure.

In yet another embodiment, the electromagnetic field generated by the generating circuit of FIG. 2A (or FIG. 2B) can also be applied using electrostatic coupling wherein an air gap exists between a generating device such as an electrode and a target pathway structure such as a molecule, cell, tissue, and organ of a plant animal or human. Advantageously, the ultra lightweight coils and miniaturized circuitry, according to some embodiments, allow for use with common physical therapy treatment modalities and at any location on a plant, animal or human for which any therapeutic or prophylactic effect is desired. An advantageous result of application of some embodiments described is that a living organism's wellbeing can be maintained and enhanced.

Figure 2C:
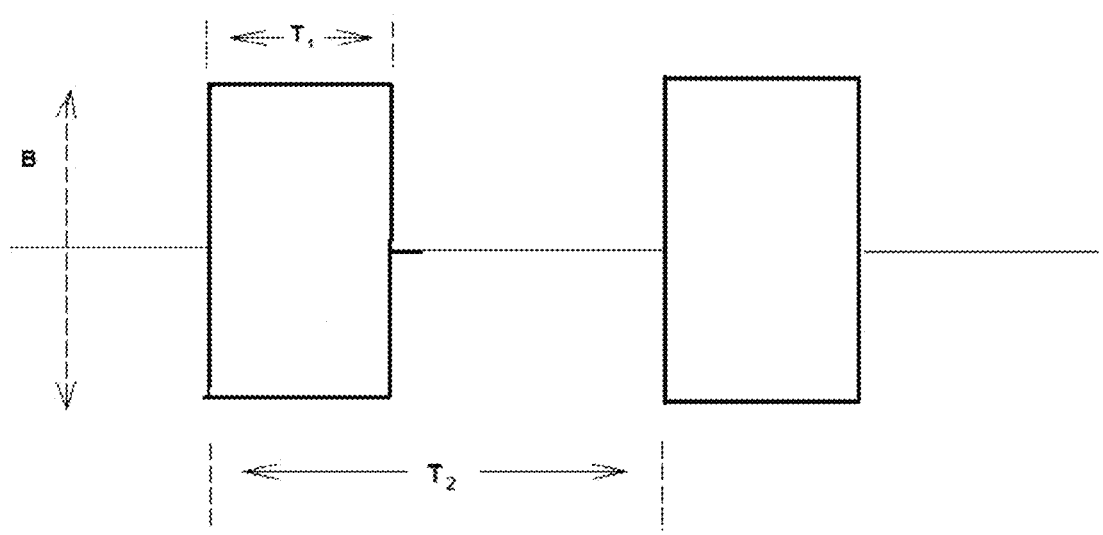
FIG. 2C illustrates a waveform delivered to a target pathway structure of a plant, animal or human, such as a molecule cell, tissue, organ, or partial or entire organism, according to some embodiments described.

Referring to FIG. 2C, an embodiment according to the present invention of an induced electric field waveform delivered to a target pathway structure is illustrated. As shown in FIG. 2C, burst duration and period are represented by $T_1$ and $T_2$, respectively. In some embodiments, the signal within the rectangular box designated at $T_1$ can be, rectangular, sinusoidal, chaotic or random, provided that the waveform duration or carrier period is less than one-half of the target ion bound time. The peak induced electric field is related to the peak induced magnetic field, shown as B in FIG. 2C, via Faraday's Law of Induction.

In further variations, the induced electric field waveform provides a burst of duration between about 1 msec and about 30 msec, containing a repetitive rectangular pulse, a sinusoidal wave or a chaotic or random waveform, having, respectively, a period or frequency less than half of the bound time of the target ion binding pathway, repeats between about 1 and about 10 bursts/sec, and induces a peak electric field of 20 V/m which is proportional to a peak applied time varying magnetic field of 50 mG according to Faraday's Law of Induction. The induced electric field illustrated in FIG. 2C can be configured according to embodiments described to modulate biochemical signaling pathways in plant, animal and human targets, such as those illustrated in FIG. 1A.

In addition to the above, induced time-varying electric fields (e.g PEMF) may be configured to affect neurological tissue including specific cellular/molecular pathways in the CNS tissues allowing these tissues to react in a physiologically meaningful manner. For example, a waveform may be configured within a prescribed set of parameters so that a particular pathway, such as CaM-dependent NO synthesis within the neurological tissue target, is modulated specifically. Both the applied waveform and the dosing or treatment regime applied may be configured so that at least this pathway is targeted specifically and effectively. Furthermore, the stimulation protocol and dosing regimen may be configured so that an electromagnetic field applicator device may be portable/wearable, lightweight, require low power, and does not interfere with medical or body support such as wound dressings, orthopedic and other surgical fixation devices, and surgical interventions.

In some embodiments, a method of treating a subject for a neurological condition, injury, or disease includes applying the one or more (or a range of) waveforms that are needed to target the appropriate pathways in the target neuronal tissue. This determination may be made through calculation of mathematical models such as those described in U.S. Patent Publication No. 2011-0112352 filed Jun. 21, 2010 as U.S. patent application Ser. No. 12/819,956 (herein incorporated by reference) to determine the dosing regimen appropriate for modulating a molecular pathway (e.g. Ca/CaM pathway).

For example, as discussed above, it is believed that pathways involved in the maintenance and repair of cerebral tissue include the Ca/CaM pathway. To modulate this pathway, in some variations, the electromagnetic/fields applied are configured to comprise bursts of at least one of sinusoidal, rectangular, chaotic or random wave shapes; burst duration less than about 100 msec, with frequency content less than about 100 MHz at 1 to 100 bursts per second. In other variations, the electromagnetic fields have a 1 to about a 50 msec burst of radio frequency sinusoidal waves in the range of about 1 to about 100 MHz, incorporating radio frequencies in the industrial, scientific, and medical band, for example 27.12 MHz, 6.78 MHz, or 40.68 MHz, repeating between about 0.1 to about 10 bursts/sec. In further variations, a PEMF signal can be applied that consists of a 2 msec burst of 27.12 MHz sinusoidal waves repeating at 2 Hz. In additional embodiments, an applied PEMF signal can consist of a sinusoidal waveform of 27.12 MHz pulse-modulated with 4 msec bursts having an amplitude of 0.001 G to 0.1 G, and repeating at 2 Hz. In additional embodiments, electromagnetic fields applied are configured to have a frequency content in a range of about 0.01 Hz to about 10,000 MHz having a burst duration from about 0.01 to about 100 msec, and having a burst repetition rate from about 0.01 to about 1000 bursts/second.

Alternatively, the carrier signal frequency may be below 1 MHz, such as 100,000 Hz, 10,000 Hz, 100 Hz or 1 Hz. In such variations, the lower carrier signal frequency requires a longer burst duration, e.g. 500 msec for 100 Hz carrier frequency, and a lower amplitude of between about 0.001 G and 0.01 G.

Electromagnetic signals can be applied manually or automatically through application devices to provide a range of electromagnetic fields, treatment ranges and doses. For example, PEMF signals can be applied for 15 minutes, 30 minutes, 60 minutes, etc. as needed for treatment. Electromagnetic signals can also be applied for repeated durations such as for 15 minutes every 2 hours. Treatment duration can also span minutes, days, weeks, etc. For example, PEMF signals can be applied for 15 minutes every 2 hours for 9 days. Furthermore, PEMF treatment can be provided for a therapeutic period of time. As used herein, the term therapeutic period is not limiting to any specific treatment regimen, but rather describes at least the total treatment period and treatment period per each treatment cycle. For example, a PEMF signal may be applied for 15 minutes every 2 hours continuously until levels of intracranial pressure decrease to acceptable levels. The therapeutic period would include at least the treatment interval, any inter-treatment interval, and the total treatment duration.

The electromagnetic applicator devices can also provide a time varying magnetic field (for example, peak=0.001 G to 0.1 G, Average=$10^{-6}$ G to $10^{-3}$ G) to induce a time varying electric field (for example average=0.1 V/m to 100 V/m) in the tissue target. Moreover, each signal burst envelope may be a random function providing a means to accommodate different electromagnetic characteristics of target tissue. Similarly, the number of treatments and the dose regime may vary depending on the progress of the target location.

In some embodiments, modifying neuronal pathways can result in increased or decreased cerebral blood flow to a target location. For example, modulating the Ca/CaM pathway can cause vasodilation in the target cerebral tissue. Vasodilation of cerebral tissue can result in increased cerebral blood flow which can mitigate inflammation, neuronal degeneration, and tissue death and promote tissue regrowth, repair, and maintenance.

In further embodiments, PEMF can be configured to treat a subject having a metal implant or other foreign object affixed to or penetrating the skull such that the treatment is not affected by the foreign object. Dose regimens such as those described above may still be applied in the presence of foreign metal objects that may have penetrated the skull (e.g. shrapnel) or been implanted (e.g. skull plate) by careful positioning of the applicator coil with respect to the position of the metal in the target, which advantageously allows for treatment of subjects with these conditions.

As is understood by one of ordinary skill in the art, the terms neurological condition, disease, injury etc. as used herein are not intended to be limited to any particular condition or injury described. A neurological injury can mean at least an injury that results from mechanical damage arising from an initial insult or trauma event and/or any secondary injury from secondary physiological responses. In some embodiments, the methods and devices contemplated may be configured to treat patients for whom the trauma event is initiated by medical personnel as part of another treatment. For example, in the case of a craniotomy to remove brain tumors or lesions, the neurological injury would include the surgical incision(s) into brain tissue and subsequent secondary injury from resulting inflammation or swelling that develops after the initial insult. Similarly, neurological conditions or diseases can mean at least, and non-exhaustively, degenerative disorders such as Alzheimer's or neurological, functional, or behavioral impairment(s) resulting from injury. For example, secondary physiological responses such as inflammation can damage healthy brain tissue which can result in impairment of a cognitive or behavioral function associated with that part of the brain.

Figure 1B:
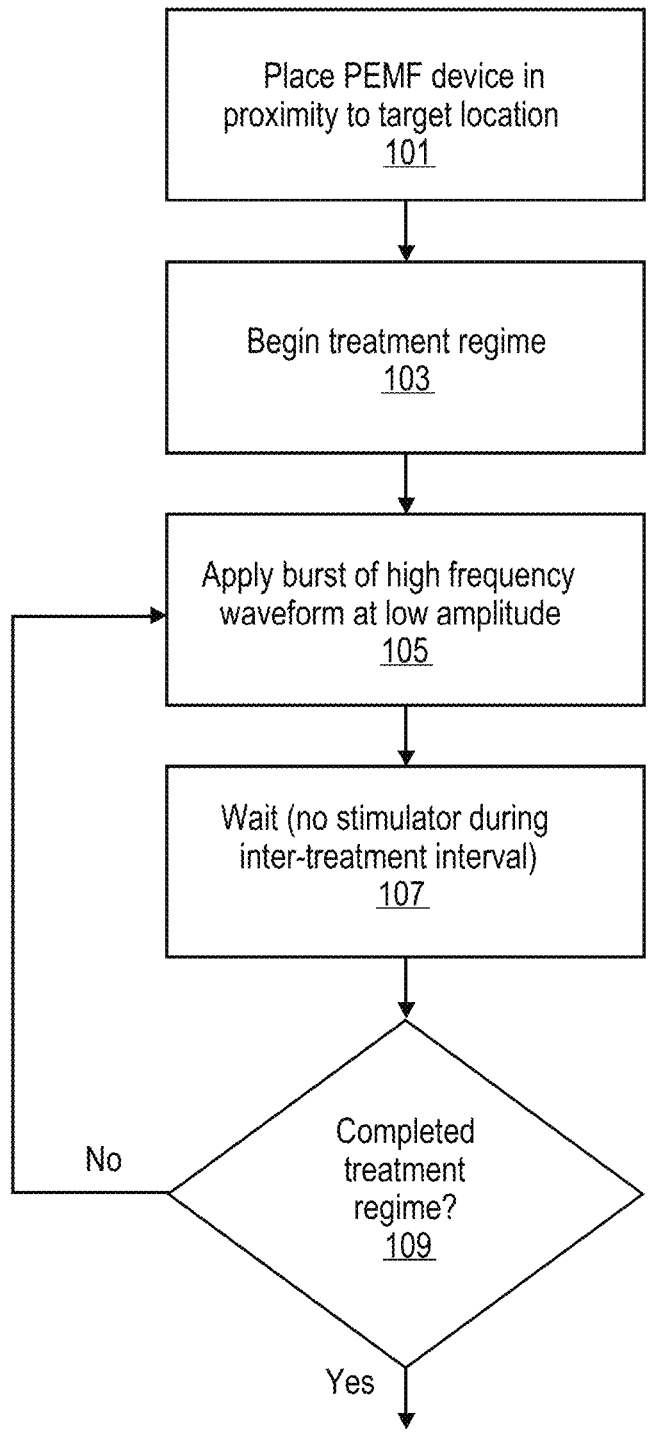
FIG. 1B is a flow diagram of a method for treating a neurological condition/injury according to an embodiment of the devices and methods described herein.

FIG. 1B is a flow diagram of a method for treating a subject with a neurological condition, disease, or injury. In some variations, before beginning the treatment, one or more (or a range of) waveforms may be determined that target the appropriate pathway for the target tissue. In such embodiments, once this determination is made, electromagnetic fields are applied to the target location.

In further embodiments, the treatment waveform or PEMF signal may be determined by configuring the PEMF waveform to target a rhythm pattern of a physiological system or process. For example, a PEMF signal may be configured to modulate brain rhythms to effect relaxation or alertness depending on the needed physiological response. As is understood in the art, physiological systems like the CNS and the peripheral nervous system (PNS), in particular, the brain or heart emit electrical activity that can be measured and recorded by, for example, electroencephalography (EEG) or electrocardiography (EKG). During particular activities, such as sleep/rest or problem solving, the brain emits electrical/rhythmic activity (e.g. circadian rhythms) in certain frequency bands associated with the activity (e.g. theta, alpha, beta, etc.)

A PEMF waveform can be configured to a specific rhythm of a target location by providing a signal with the frequency, amplitude, burst duration, etc. associated with a particular activity of that target location. For example, for treatment of a neurological condition such as Alzheimer's, a PEMF waveform can be brought in close proximity to a region of the brain associated with problem solving. In such cases, the PEMF waveform provided to the patient can be configured to the rhythm frequency/band that is generally measured when normal problem solving skills are employed. The PEMF waveform may then be used to stimulate the target region while the patient is engaged in a problem solving activity. This treatment may help the patient regain or improve problem solving skills where the target region has exhibited diminished ability to emit normal electrical activity.

In further embodiments, the PEMF waveform may be configured to modulate rhythms associated with a physiological response that arises from a neurological injury. For example, as can be appreciated, neurological damage such as traumatic brain injury results in both secondary physiological responses in the CNS as well as responses in peripheral systems. With brain trauma, a patient's ability to regulate and maintain periphery systems such as the cardiac and pulmonary systems may be indirectly compromised. As such, some embodiments contemplated provide for PEMF configurations that treat a neurological injury by targeting non-neurological systems affected by the injury. In some embodiments, the PEMF waveforms are configured to modulate the rhythms or electrical activity of one or more non-neurological system(s).

In further embodiments, the PEMF waveform may be configured to modulate sleep patterns. In particular, PEMF configurations may increase the duration of slow-wave (Delta) sleep in each sleep cycle which may allow the injured person to maximize the production of human growth hormone, which, in turn, may increase healing for any injury, including CNS and PNS injuries, and provides a prophylactic response to protect from further injury.

As described in FIG. 1B, a method of treating a subject with a neurological injury or condition may include the step of placing the tissue to be treated (e.g. near one or more CNS regions) in contact, or in proximity to, a PEMF device 101. Any appropriate PEMF device may be used. In general, the device may include an applicator (e.g. inductor applicator) which may be placed adjacent to or in contact with the target location/tissue. The device may also contain a signal conditioner/processor for forming the appropriate waveform to selectively and specifically modulate a pathway (e.g. Ca/CaM pathway). In further embodiments, the device may include a timing element (e.g. circuit) for controlling the timing automatically after the start of the treatment.

In the example shown in FIG. 1B, once treatment begins 103, the device, in some variations, applies an envelope of high-frequency waveforms at low amplitude (e.g. less than 50 milliGauss, less than 100 milliGaus, less than 200 milliGauss, etc.) 105. This envelope of high-frequency pulses is then repeated at a particular frequency after an appropriate delay. This series of bursts can be repeated for a first treatment time (e.g. 5 minutes, 15 minutes, 20 minutes, 30 minutes, etc.) and then followed by a delay during which the treatment is "off" 107. This waiting interval (inter-treatment interval) may last for minutes or hours (15 minutes, 2 hours, 4 hours, 8 hours, 12 hours, etc.) and then the treatment interval may be repeated again until the treatment regime is complete 109.

In some variations, the treatment device is pre-programmed (or configured to receive pre-programming) to execute the entire treatment regime (including multiple on-periods and/or intra-treatment intervals) punctuated by predetermined off-periods (inter-treatment intervals) when no treatment is applied. In further variations, the device is pre-programmed to emit a PEMF signal at 27.12 MHz at 2 msec bursts repeating at 2 bursts/sec. In other embodiments, the device is pre-programmed to emit a PEMF signal at 27.12 MHz (at about amplitude 250-400 mV/cm) pulsed in 4 msec bursts at 2 Hz.

As discussed, the selection of a treatment regime may be determined by the particular neurological injury or condition etc. at issue. In the case of treating secondary physiological responses from TBI, the treatment parameters may be selected to target any number or combination of physiological responses. For example, some embodiments contemplated provide for devices and methods for reducing intracranial pressure. Oftentimes a trauma event such as brain surgery will induce cerebral edema, the extra- and intracellular accumulation of fluid resulting from changes in vascular endothelium causing vasodilation and leakage as well as surges of extracellular fluid into cells after disturbances in glutamate release and calcium and sodium ion influx. This is potentially fatal as increased intracranial pressure decreases cerebral perfusion pressure and interrupts cerebral blood flow to brain tissue, which can cause ischemia and neuronal death.

To manage intracranial pressure, some embodiments provide a method of reducing intracranial pressure by applying a PEMF signal in close proximity to a target location. Such treatment parameters may include any of those discussed, which are found suitable for the needs of the patient. Moreover, in some embodiments, the selected PEMF signal can be applied continuously to the target area until an acceptable intracranial pressure level is reached. An acceptable intracranial pressure level can be patient-specific depending on the circumstances; however, generally normal intracranial pressure ranges from about 5 mmHg to about 15 mmHg. Additionally, intracranial pressure above about 20 mmHg is generally considered harmful. As such, PEMF treatment may be initiated once intracranial pressure is above an acceptable level.

Alternatively, PEMF treatment may be discontinued once acceptable levels are attained. In some embodiments, the PEMF treatment can be applied as shown in FIG. 1B with inter-treatment intervals. For example, a PEMF signal of 27.12 MHz pulsed in 4 msec bursts at 2 Hz may be applied for 15 minutes every 2 hours for 9 days. In other embodiments, the PEMF signal may be applied continuously without an inter-treatment interval until an acceptable level of intracranial pressure is reached. In further embodiments, the PEMF therapy includes monitoring a neurological factor such as intracranial pressure of the subject such that PEMF treatment can be initiated or discontinued depending on the levels of intracranial pressure.

In some embodiments, the patient may experience intracranial pressure below about 20 mmHg; however, due to lower cerebral perfusion pressure, PEMF therapy may be initiated to mitigate conditions such as ischemia. In further embodiments, the PEMF therapy may be preventative and applied to maintain the subject's pressure levels within a selected range that may or may not be within the normal pressure ranges described above. Additionally, a PEMF device may be pre-programmed with a controller or processor that monitors and adjusts PEMF treatment based on the levels of intracranial pressure. A PEMF device may be configured to communicate with a sensor or other data gathering devices/components that provide information regarding intracranial pressure or other neurological factors.

In addition to intracranial pressure, additional embodiments provide for PEMF methods and devices for treating inflammation resulting as a secondary physiological response to neurological injury (e.g. TBI). Inflammation is a natural and protective systemic physiological response to invading pathogens to preserve tissue viability and function. However, if this process remains unchecked, it can lead to secondary tissue damage in the CNS. In the case of brain injury, inflammation can restrict cerebral blood flow and cause damage or death to healthy brain tissue. Although the complex process involved in inflammation is not completely known, it is understood that following injury, microglia and astrocytes will activate and migrate to the injury site. Once activated, these cells will secrete destructive cytokines (e.g. IL-1α, IL-1β and TNF-α) as well as other inflammatory molecules such as chemokines, which can attract additional immune-mediators. Some of these immune-mediators can penetrate the blood-brain barrier and further add to an inflammatory response. Although microglia, cytokines, chemokines, and other inflammatory promoters are required to some extent to remove invading pathogens, protracted and unremitting inflammation can cause long term damage. As such, some embodiments provide for PEMF treatments and devices to alter the levels of inflammatory factors present in a target location.

Because increased levels of cytokines such as IL-1β have been correlated with high intracranial pressure, inflammation, and breakdown of the blood-brain barrier, some embodiments provide for a PEMF treatment that can reduce or mitigate the levels of cytokines in order to prevent secondary injury to target brain tissue. In such embodiments, a PEMF applicator device such as the one described in FIG. 2B is placed in close proximity to a target tissue location (e.g. brain area). The PEMF applicator device is then activated and generates a PEMF signal configured to reduce the levels of cytokines in the target location. In some embodiments, a PEMF signal of 27.12 MHz pulsed in 4 msec bursts at 2 Hz for about 5 to about 15 minutes every 20 minutes to reduce the quantities of IL-1β present in target location. The PEMF signal may be applied for a selected amount of time before pausing for an inter-treatment interval (see FIG. 1B) and then repeated for a total treatment time. In further embodiments, the PEMF treatment may be applied continuously until acceptable levels of cytokines or inflammation are reached. The PEMF treatment may also be applied continuously or intermittently in response to direct data regarding level of cytokines or inflammation or indirect data such as levels of cerebral blood flow.

Figure 11:
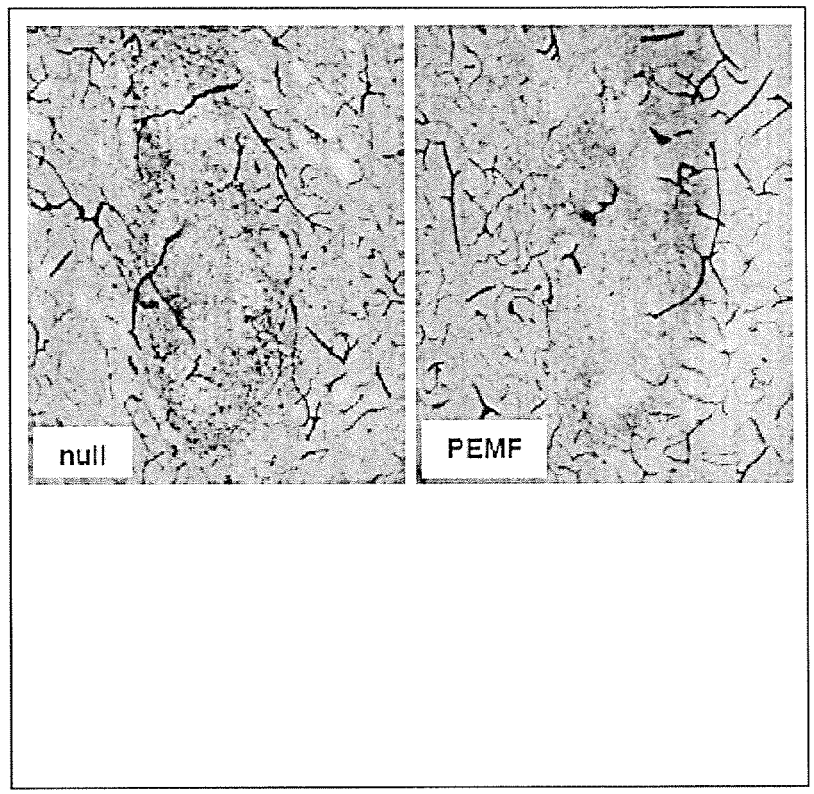
FIG. 11 illustrates the effect of a PEMF treatment according to embodiments described on inflammation in response to transplants of dissociated embryonic midbrain neurons.
Figure 12:
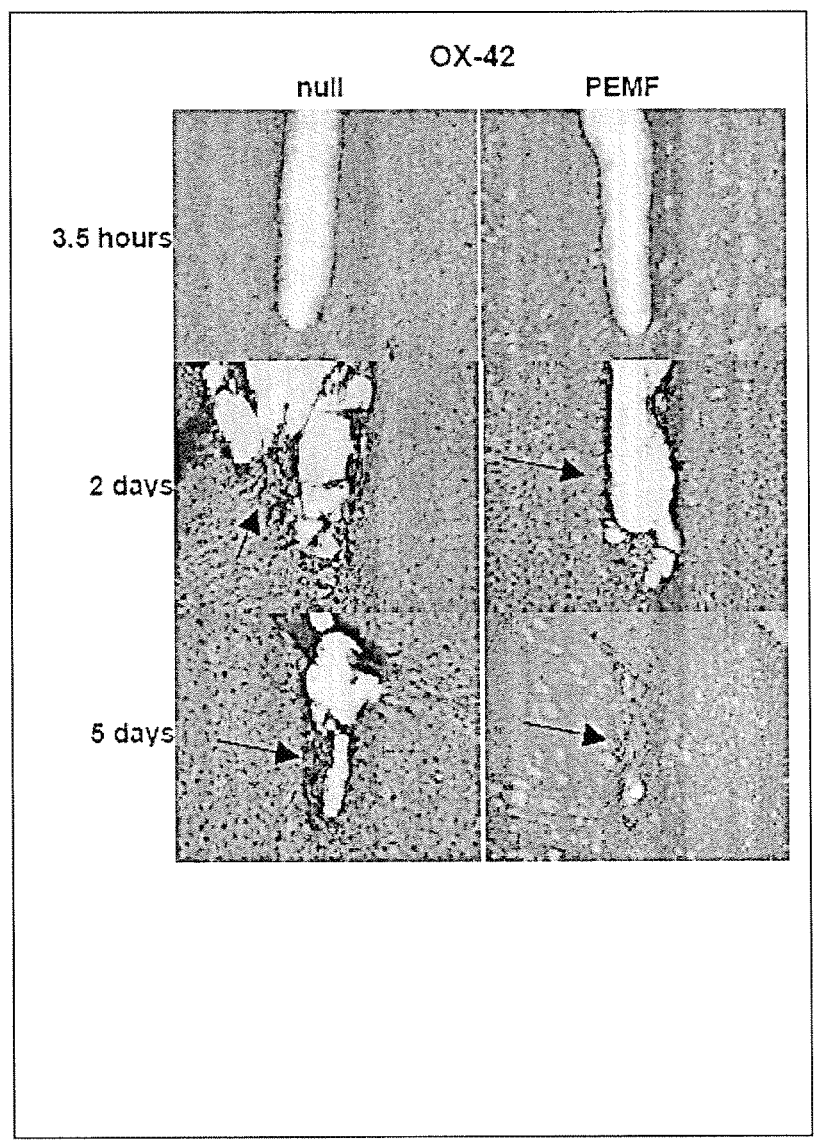
FIG. 12 illustrates the effect of a PEMF treatment according to embodiments described on microglia in rats subjected to penetrating injuries.

In other embodiments, the PEMF treatment may be directed toward altering the levels of microglia or astrocytes present in the target location. As discussed, once activated, microglia not only produce cytokines but also remove damaged or dead tissue and infectious agents. In other words, microglia are dually neuroprotective and neurotoxic. As such, reducing or increasing the levels of microglia at different stages following a neurological injury or condition may modulate the helpful and harmful effects of microglia present in the target location. For example, in the immediate period following injury, an increase in activated microglia may help to clear and collect pathogens and debris from cellular or tissue damage. By doing so, an increased level of microglia can reduce the chances of infection and prevent inflammation before it begins. Moreover, increased activity of microglia may enhance the repair of axons. Alternatively, at a later stage post-injury, reducing the number of activated microglia can reduce inflammation by preventing microglia from producing pro-inflammatory factors such as cytokines and chemokines. As the suitability of increasing or decreasing microglia levels in a target area are dependent on the type of injury/condition and the patient's needs, flexibility will be needed to modify PEMF treatment as needed. In some embodiments, the PEMF device/treatment can be pre-programmed to alter treatment as needed according to monitored conditions such as the levels of inflammation, levels of microglia, or time period after injury. In other variations, the PEMF treatment can be manually modified as needed. In further variations, the PEMF treatment may appear to first decrease microglial activity, but the apparent decrease in microglia may be transitory and microglial activity may actually be increased/accelerated over the course of treatment. As shown in FIGS. 11 and 12 (and further described in detail in Examples 7 and 8), PEMF treatment can effect an increase or decrease in microglial activity.

Further embodiments provide for treatments and devices for preventing neuronal death. Injuries caused by both contusive trauma and by invading foreign objects (e.g. penetrating injury) will kill neurons, which can be responsible for lasting behavioral deficits as well as limbic and cognitive disabilities. Some PEMF treatments contemplated provide for therapies that increase neuronal survival. For example, PEMF signals can be applied to a target location with damaged neuronal cells. The PEMF signals may increase the level of activated microglia present at the site, for example, which can help remove pathogens that could cause infection to already damaged neuronal cells. Moreover, reductions in tissue swelling and inflammation also indirectly increase neuronal survival, as these processes can both initiate and exacerbate acute and chronic neurodegeneration. Treatment parameters may be selected according any of the described regimes as needed for treatment.

In treating neurological conditions and injuries, a primary concern is retaining or recovering cognitive, motor, limbic, and behavioral functions. Tissue damage and death, especially in the brain, can irreversibly affect the ability of patients to function normally after a traumatic event. Some embodiments provide for treatments and devices to improve cognitive, motor, behavioral etc. function after a neurological injury/condition. Some variations provide for short term and long term PEMF treatment where ongoing assessment of the patient's progress is recorded to determine whether treatment should be continued or modified.

As can be appreciated, PEMF signals can be configured to treat one or more of the conditions described. For example, a PEMF treatment may be used to reduce intracranial pressure and inflammation in a patient in need thereof.

FIG. 2B illustrates an embodiment of an apparatus 200 that may be used. The apparatus is constructed to be self-contained, lightweight, and portable. A circuit control/signal generator 201 may be held within a (optionally wearable) housing and connected to a generating member such as an electrical coil 202. In some embodiments, the circuit control/signal generator 201 is constructed in a manner that given a target pathway within a target tissue, it is possible to choose waveform parameters that satisfy a frequency response of the target pathway within the target tissue. For some embodiments, circuit control/signal generator 201 applies mathematical models or results of such models that approximate the kinetics of ion binding in biochemical pathways. Waveforms configured by the circuit control/signal generator 201 are directed to a generating member 202. In some variations, the generating member 202 comprises electrical coils that are pliable and comfortable. In further embodiments, the generating member 202 is made from one or more turns of electrically conducting wire in a generally circular or oval shape, any other suitable shape. In further variations, the electrical coil is a circular wire applicator with a diameter that allows encircling of a subject's cranium. In some embodiments, the diameter is between approximately 6-8 inches. In general, the size of the coil may be fixed or adjustable and the circuit control/signal generator may be matched to the material and the size of the applicator to provide the desired treatment.

The apparatus 200 may deliver a pulsing magnetic field that can be used to provide treatment of a neurological condition or injury. In some embodiments, the device 200 may apply a pulsing magnetic field for a prescribed time and can automatically repeat applying the pulsing magnetic field for as many applications as are needed in a given time period, e.g. 6-12 times a day. The device 200 can be configured to apply pulsing magnetic fields for any time repetition sequence. Without being bound to any theory, it is believed that when electrical coils are used as a generating member 202, the electrical coils can be powered with a time varying magnetic field that induces a time varying electric field in a target tissue location.

In other embodiments, an electromagnetic field generated by the generating member 202 can be applied using electrochemical coupling, wherein electrodes are in direct contact with skin or another outer electrically conductive boundary of the target tissue (e.g. skull or scalp). In other variations, the electromagnetic field generated by the generating member 202 can also be applied using electrostatic coupling wherein an air gap exists between a generating member 202 such as an electrode and the target tissue. In further examples, a signal generator and battery is housed in the miniature circuit control/signal generator 201 and the miniature circuit control/signal generator 201 may contain an on/off switch and light indicator. In further embodiments, the activation and control of the treatment device may be done via remote control such as by way of a fob that may be programmed to interact with a specific individual device. In other variations, the treatment device further includes a history feature that records the treatment parameters carried out by the device such that the information is recorded in the device itself and/or can be transmitted to another device such as computer, smart phone, printer, or other medical equipment/device.

In other variations, the treatment device 200 has adjustable dimensions to accommodate fit to a variety of patient head sizes. For example, the generating member 202 may comprise modular components which can be added or removed by mated attaching members. Alternatively, the treatment device 200 may contain a detachable generating member (e.g. detachable circular coil or other configurations) that can be removed and replaced with configurations that are better suited for the particular patient's needs. A circular coil generating member 202 may be removed and replaced with an elongate generating member such that PEMF treatment can be applied where other medical equipment may obstruct access by a circular generating member 202. In other variations, the generating member may be made from Litz wire that allows the generating member to flex and fold to accommodate different target areas or sizes.

In other embodiments, the diameter of a circular generating member may be selected based on the desired treatment regimen. In some variations, the depth of penetration for the electromagnetic field increases with increased diameter. In such embodiments, a larger diameter will provide a field with a greater field volume allowing for greater penetration in the target location. Accordingly, by modifying the diameter or size of the generating member, the depth of the treatment field can be adjusted as needed. Greater depth of penetration may be advantageous where the injured target region is below the surface of the target location. Alternatively, where a greater depth of penetration is not needed, generating members of smaller size may be more appropriate where surface application is desired. For example, for treatment of a large surface area, an array of smaller sized generating members can be used to cover a large area without deep penetration beyond the surface.

In further embodiments, the inductive device illustrated in FIG. 2B is flexible, portable and, if desired, disposable; and can be used alone or incorporated into an anatomical positioning device such as a dressing, bandage, compression bandage, compression dressing; knee, elbow, lower back, shoulder, foot, and other body portion wrap and support; garments, footwear, gloves, and fashion accessories; mattress pads, seat cushions, furniture, beds; in seats or beds within cars, motorcycles, bicycles, buses, trains, planes, boats and ships.

In some embodiments, the devices may include a sensor configured to monitor a patient's condition for changes. For example, a device may include a sensor that collects data on the patient's intracranial pressure. Based on the amount of intracranial pressure, the device may automatically turn on for treatment once threshold pressure levels are reached. Similarly, the device may turn off automatically if pressure levels return to normal. Additionally, a device providing treatment may modify and adjust treatment parameters based on the feedback from sensors. For example, a device may change treatment parameters if the sensor registers an increase in intracranial pressure. Moreover, in some variations, medical staff may be notified of changes to treatment parameters where the delivery device can communicate with another device such as computer, smart phone, printer, or other medical equipment/device.

Figure 3A:
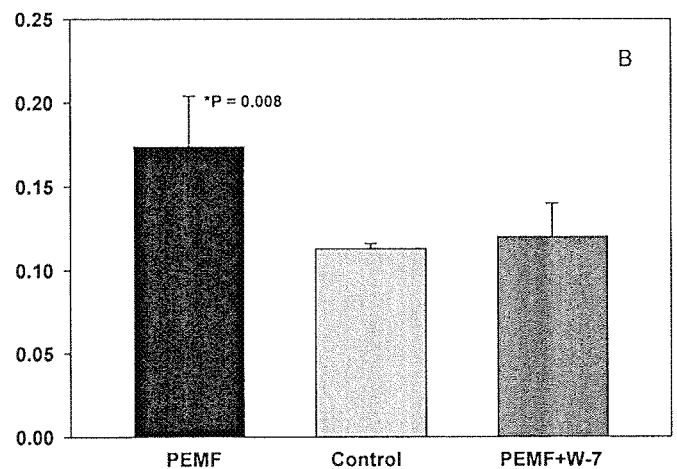
FIGS. 3A and 3B illustrates the effect of a PEMF treatment according to embodiments described on nitric oxide (NO) release from MN9D neuronal cell cultures.

Example 1 An EMF signal, configured according to an embodiment of the present invention to modulate CaM-dependent signaling, consisting of a 27.12 MHz carrier, pulse-modulated with a 3 msec burst repeating at 2 Hz and a peak amplitude of 0.05 G, was applied for 30 minutes to the MN9D dopaminergic neuronal cell line and increased NO production by several-fold in a serum depletion paradigm and produced a 45% increase in cGMP. The EMF effects on NO and cGMP were inhibited by the CaM antagonist N-(6-Aminohexyl)-5-chloro-1-naphthalenesulfonamide hydrochloride (W-7), indicating the EMF signal acted in this neuronal culture according to the transduction mechanism illustrated in FIG. 1A. These results are summarized in FIG. 3A.

Figure 3B:
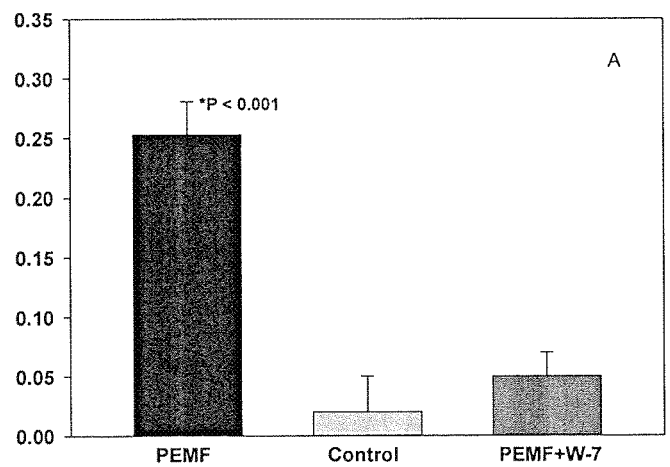

The effect of the same EMF signal on cAMP production in MN9D cells was also studied. MN9D cells in serum free medium were removed from the incubator (repeatable temperature stress injury to transiently increase intracellular $Ca^{2+}$) and exposed to EMF for 15 min. cAMP was evaluated in cell lysates by ELISA. Results demonstrate that an EMF signal, configured according to an embodiment of the present invention, increased cAMP production by several-fold. Notably, the c-NOS inhibitor L-NAME abolished the PEMF effect on cAMP. The results, summarized in FIG. 3B, indicate EMF signals, configured according to an embodiment of the present invention, affect neuronal differentiation and survival.

Example 2 In this example, a highly reproducible thermal myocardial injury was created in the region of the distal aspect of the Left Anterior Descending Artery at the base of the heart of adult male Sprague Dawley rats. The EMF waveform, configured as an embodiment of the present invention, was a 2 msec burst of 27.12 MHz sinusoidal waves repeating at 2 bursts/sec delivering 0.05 G at the tissue target. Five freely roaming animals in a standard rat plastic cage, with all metal portions removed, were placed within a single turn 14×21 inch coil. Exposure was 30 min twice daily for three weeks. Sham animals were identically exposed, but received no EMF signal.

Figure 4:
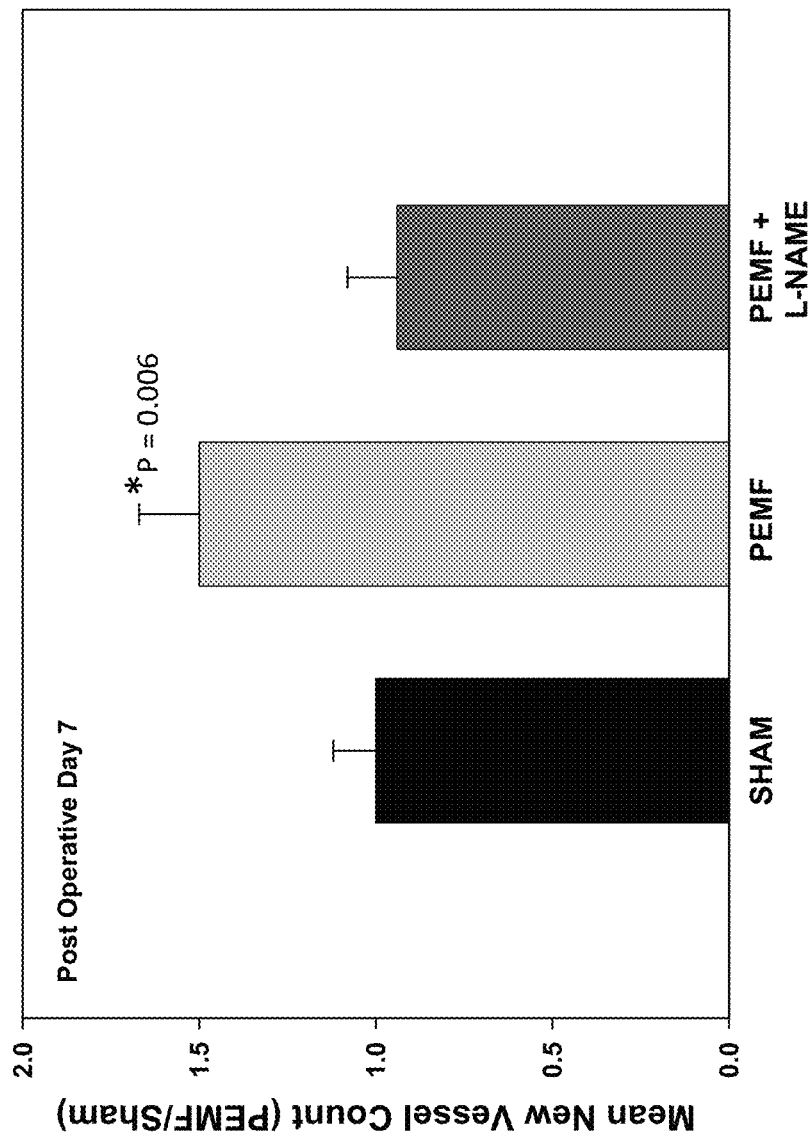
FIG. 4 illustrates the effect of a PEMF treatment according to embodiments described on angiogenesis in thermal myocardial necrosis in a rat model.

Upon sacrifice, myocardial tissue specimens were stained with CD-31 to evaluate the presence of newly forming blood vessels and capillaries in peri-ischemic tissue. Results at 21 days showed that number of vessels and capillaries in peri-ischemic myocardial tissue was increased by approximately 100% (p<0.001) in EMF vs sham exposed animals. That an EMF signal, configured as an embodiment of the present invention, modulated CaM-dependent NO release, as illustrated in FIG. 1A, was verified by feeding animals L-NAME, a cNOS inhibitor, in their drinking water for 7 days. EMF, configured as an embodiment of the present invention, accelerated angiogenesis at 7 days by 60%. The EMF effect was abolished by L-NAME, as illustrated in FIG. 4.

Example 3 In this example, inflammation was induced in the left hind paw of Harlan Sprague-Dawley rats (200-340 g) by injection of 100 μL of a 3.5 mg/mL sterile phosphate buffered saline-based carrageenan solution into the footpad using a 30 gauge tuberculin syringe. The carrageenan dose was carefully calibrated to produce a mild, controllable form of inflammation that could be evaluated for rate of onset. Edema was determined using a plethysmometer volume displacement transducer system (Stoelting Company, Wood Dale, Ill.). Edema was measured pre-carrageenan injection and at 1, 4 and 8 hours post-injection. Rats were exposed to either the PEMF signal or a control, untreated experimental coil configuration for 15 min. EMF exposures were at 0.25, 2, 4 and 8 hours post-injection. The signal consisted of a 2 msec burst of 27.12 MHz sinusoidal waves repeating at 2 bursts/sec, and inducing 20 V/m electric field at a target diameter of 2 cm. This PEMF signal was configured, according to an embodiment of the present invention to accelerate $Ca^{2+}$ binding in a CaM-dependent signaling pathway. Data were analyzed with SigmaStat 3.0 software (SPSS, Chicago, Ill.) using Student's unpaired t-test and one way ANOVA, as appropriate. Differences were also compared using the Mann-Whitney test for two independent groups. Significance was accepted at P≤0.05.

Figure 5:
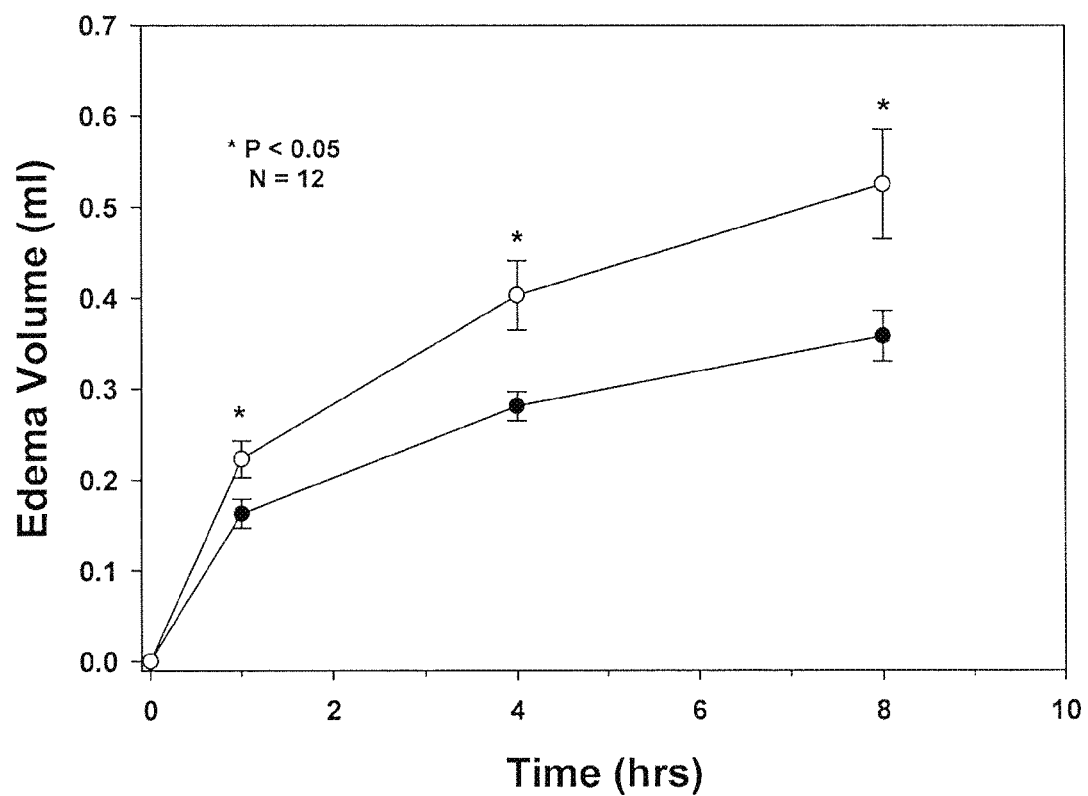
FIG. 5 illustrates the effect of a PEMF treatment according to embodiments described on edema formation in a carrageenan-induced paw edema model of inflammation in the rat.

The results showed mean edema volume in the sham treated animals was 33±7% greater at 1 hour post-injection (P=0.037), 41±8% greater at 4 hours (P=0.005), and 47±9% greater at 8 hours (P=0.009) than edema volume in the PEMF treated animals at these time points. These results, summarized in FIG. 5, demonstrate that a PEMF signal, configured as an embodiment of the present invention, accelerates $Ca^{2+}$ binding to CaM in the NO signaling cascade that regulates lymphatic evacuation of edema from inflammation.

Example 4 In this example, groups of rats were subjected to invasive and contusive traumatic brain injury and treated with an EMF signal configured as an embodiment of the present invention consisting of a 27.12 MHz carrier, pulse-modulated with a 3 msec burst repeating at 2 Hz and a peak amplitude of 0.05 G.

Adult male Sprague Dawley rats (350-400 g) were housed in a climate-controlled animal facility with two rats per cage. Food and water were provided ad libitum in a 12-hour light/dark cycle. Animals were maintained, operated on, treated, and euthanized in accordance with federal, state, and IACUC guidelines at the Montefiore Medical Center.

Closed Skull Contusion Injury: Twenty rats (10/group) were subjected to a moderate closed-head injury under anesthesia using the Marmarou impact-acceleration model, with the following modifications. Briefly, rats were anesthetized with ketamine/medetomidine (0.75 mg/0.5 mg/kg, i.p.). After depilation and disinfection, the calvarium was exposed by creating a 1 cm vertical, midline incision through the scalp and displacing the periosteum. To diffuse the impact force and reduce incidence of skull fracture, a metal washer (10 mm diameter, 2 mm thickness) was affixed directly to the skull with epoxy cement midway between the lambda and bregma. Rats were secured directly underneath the weight-drop device on foam bedding (Foam to Size; Ashland, Va.; spring constant=4.0). A diffuse closed-head injury was produced by dropping a 258.7-gram weight in a plexiglass tube from specified heights up to 2 meters, creating forces of impact from 1 to 4 Newtons (4.46N). After impact, the disk was removed from the skull and the periosteum and scalp were approximated with discontinuous nylon sutures. Anesthesia was reversed and animals were either treated with PEMF signals or placed in similar containers in the absence of signals.

Figure 8:
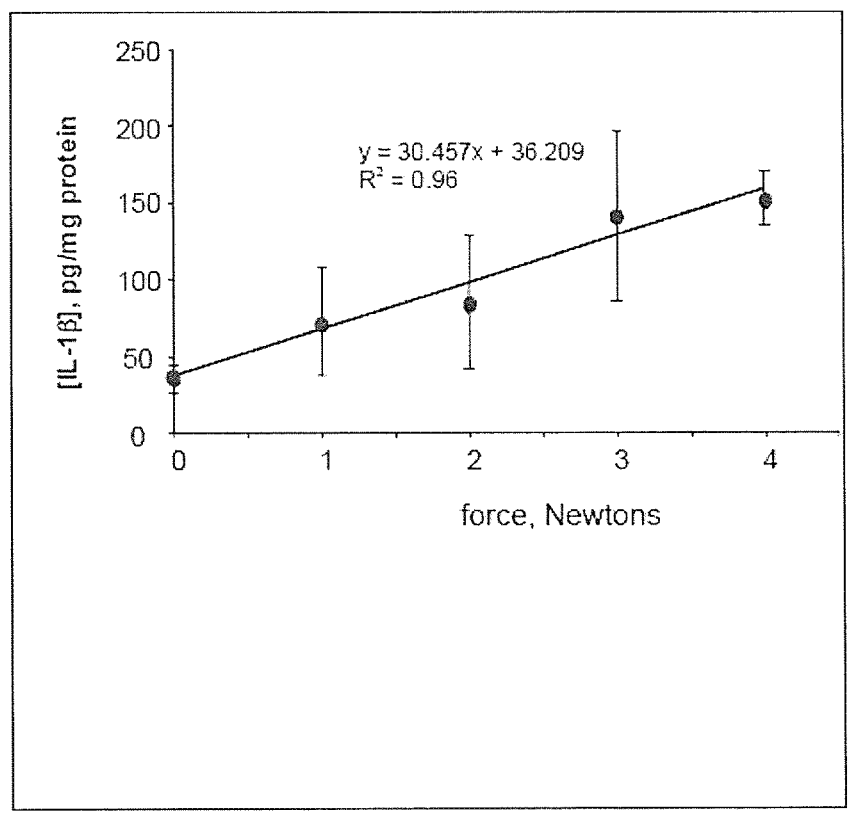
FIG. 8 illustrates the proportional relationship between levels of 1L-1β and force in the Marmarou weight-drop model.

The Marmarou weight-drop model was selected for this study partly because it has been found that the levels of 1L-1β closely correlate to the force of the injury in the Marmarou weight-drop model. For example, as shown in FIG. 8, in a previous study, rats were subjected to TBI according to the Marmarou weight-drop model by varying the height from which a 257 g weight was dropped. After six hours, levels of 1L-1β were quantified in brain tissue by ELISA. Points shown on FIG. 8 represent mean values for 3 rats+/−SEM. Data at 0 force was determined from rats receiving sham surgery.

Penetrating Brain Injury: Sixty rats were subjected to bilateral stab injuries to the striatum. Rats were anesthetized with ketamine/medetomidine (0.75 mg/0.5 mg/kg, i.p.) and secured on a stereotaxic frame (David Kopf) with the tooth bar at 3.3 mm below the interaural line. After depilation and disinfection, the calvarium was exposed, as described above, and the separated tissue was secured with hemostats. Two 1 mm burr holes were created by a trephine drill above the striatum at stereotactic coordinates 0.5 mm anterior to and 2.5 mm lateral to Bregma. A 23S gauge blunt-end needle from a Hamilton syringe was inserted 5.2 mm below the dura into each striatum and removed over two minutes. After lesioning, burr holes were sealed with bone wax and the incision site was closed with 4-0, non-absorbable nylon sutures. Rats were reversed from anesthesia with 1 mg/kg medetomidine and placed in containers for PEMF treatment.

PEMF treatment: Animals were exposed to PEMF generated by a sinusoidal 27.12 MHz radiofrequency signal pulse-modulated with 3 millisecond bursts with 0.05 G amplitude, and repeating at 2 Hz beginning immediately after surgery from a coil positioned around a plastic shoebox with a ventilated lid and connected to a PEMF signal generator which automatically provided a signal regimen consisting of signal on for 5 min in every 20 minute time segment for 6 hours. For treatments longer than 6 hours, metal cage inserts were removed, food and hydrogel packs were placed in the cages, and plastic outer cage tops with filters were placed in a larger container equipped with a metal coil around its perimeter on a plastic cart in the animal care facility to avoid signal distortion from surrounding metal.

PEMF signals were delivered externally from a signal generator attached by a wire to the coil. Treatment was administered for 5 minutes every 20 minutes and rats were allowed to move freely in their cages during this time. Identical procedures were followed for the control group, i.e. rats were placed in identical containers in the same room and were fed and handled in an identical manner to rats receiving treatment. Immediately before euthanasia, rats were re-anesthetized and CSF was collected, and after euthanasia, brains were harvested and immediately either fixed in 4% paraformaledhyde or frozen at −80° C. until analysis.

CSF Collection: CSF was obtained utilizing a modification of the Nirogi technique (REF). Briefly, a standard 23 G Vacutainer® Push Button Blood Collection Syringe with 12" (what is the diameter of the hole) tubing (BD) was connected to a 1 cc insulin syringe. Anesthetized rats were positioned on a stereotaxic frame with the tooth bar set to angle the at head 45° in a downward direction. The needle was inserted in an upright position into the medial portion of the cisterna magna until CSF was released into the tubing. Fluid was collected until blood was visible and tubing was clamped with a hemostat to separate clear and blood-tainted CSF. Samples of clear CSF were released into microfuge tubes and cellular material was pelleted by centrifugation (speed and time of centrifuge). Cleared samples were immediately frozen at −80° C.

Tissue Processing: For the weight-drop injury, whole brain hemispheres minus cerebella were frozen. For the penetrating injury, a 5-mm cylinder of brain tissue from the left hemisphere surrounding the stab injury were removed and frozen. The right hemisphere was fixed by immersion in 4% paraformaldehyde for 2 days and stored in 30% sucrose with 0.05% sodium azide.

IL-1β Analysis: Frozen specimens were processed by homogenization using a polytron (model, Manufacturer) in lysis buffer containing tris-buffered saline and centrifuged at 16,000 g for 10 minutes at 4° C. to pellet particulate matter. Supernatants were frozen at −80° C. and triton X-100 was added to a final concentration of 0.1%. IL-1β levels were quantified using a rat IL-1β ELISA duo set (R&D Systems) following manufacturer's recommendations. Results were normalized for protein content determined with the Biorad protein assay.

OX-42 immunohistochemistry: Sixty-micron tissue sections through the striatum were generated using a tissue slicer (Ted Pella) and stored until use in phosphate-buffered saline (150 mM NaCl, 10 mM sodium phosphate, pH 7.4; PBS) with 0.05% sodium azide. For immunostaining, sections belonging to a series consisting of every 2nd-3rd section were permeabilized in 0.25% Trition X-100 in PBS with 3% hydrogen peroxide to extinguish endogenous peroxidase activity. Non-specific binding was blocked with 3% horse serum in PBS with 0.25% Triton X-100 ("block"). Sections were incubated in mouse OX-42 antibody (Serotec; 1:1000) in block overnight at 37° C. After washing in PBS, sections were incubated for 2 hours at 37° C. with biotin anti-mouse in block (Amersham; 1:600). After subsequent washing and 1.5 hours incubation in peroxidase ABC (Vector Laboratories; 1:500), sections were washed and staining was visualized with DAB (Vector). After washing, sections were dehydrated, coverslipped, and photographed at 20× magnification.

Evaluation of microglial activation: OX-42 staining was quantified in a series of every 2-3 sections representing 0.7 mm through the center of the lesion for animals subjected to a penetrating lesion. Initially, the degree of microglial staining in all animals was scored by 4 individuals, where scores (0-5) represented staining intensity and the area occupied by stained cells. Tissue sections from groups that were exposed to PEMF (null) signals for 24 and 48 hours after injury were analyzed further using Image J software. Immuno-stained regions were outlined and areas were measured using a calibrated length. The intensity of immunostaining was quantified by densitometry, defined as an integrated density, calibrated against selected areas from stained tissue sections that represented the entire spectrum of staining.

Statistical Analysis: Data for each group was compared and analyzed for significant differences by Student's t-test and by analysis of variance (ANOVA) followed by Fischer's PLSD test, when more than two groups were compared. Differences between groups generating p-values equal to or less than 0.05 were considered statistically significant.

PEMF treatment reduced levels of IL-1β after contusive TBI. CSF and brain tissue were collected from injured animals in PEMF and control groups as well as from sham and intact animals after 6 hours, when peak IL-1β levels were expected using this injury model. Results demonstrate that intact animals had the lowest levels of IL-1β (29±4 pg/mg protein), which increased 34% in the sham group to 39±7 pg/mg protein. After injury, mean levels of IL-1β in the group that did not receive PEMF treatment was 55±3 pg/mg protein, which was not significantly different from levels of this inflammatory cytokine in animals that received sham surgery. Mean levels of IL-1β in animals that received PEMF treatment were 50±4 pg/mg protein, indicating that there were no significant effects on levels of this peptide in brain homogenates.

Results also demonstrated that levels of IL-1β in CSF changed dramatically in response to both injury and PEMF treatment. Mean levels of this cytokine in CSF from intact animals was 19±7 pg/mL CSF, increasing to 25±21 pg/mL in the sham group (31%). Levels in animals receiving a contusive 3N injury rose to 252±91 pg/mL, a 10-fold increase over the sham group. Moreover, animals receiving PEMF treatment demonstrated significantly lower concentrations (44±25 pg/mL), or levels that were 83% lower than those of animals receiving the injury, and less than twice the mean concentration of IL-1β in animals receiving sham surgery.

Results for PEMF reduced levels of IL-1β after penetrating brain injury: Results illustrating the time course of IL-1β expression demonstrate similarly low levels of IL-1β in brain homogenates from intact and sham animals; 24±5 and 24±6 pg/mg protein, respectively. In addition, two animals from the sham group were treated with PEMF signals for 6 hours before they were euthanized. Animals in this group demonstrated mean IL-1β levels of 15.4 and 16.6 pg/mg protein for PEMF and sham animals respectively, but the number of animals in this group was too low to compare with either intact or sham rats (n=5 and n=2, respectively). At 3.5 hours after injury, IL-1β levels increased approximately 2-fold and attained their highest levels of any time point measured at 6 hours after injury in PEMF treated and control groups at 93±15 and 99±11 pg/mg protein, approximately 4 times basal levels. Importantly, at 17 hours after injury, levels of IL-1β were significantly lower in the PEMF group (42±5 pg/mg protein) than those of the control group (61±5 pg/mg protein; p≤0.04). Control levels decreased and values at later time points were similar in both groups up to 9 days after injury.

In CSF, levels of IL-1β followed a more protracted time course. In intact naive animals, basal levels of IL-1β were 32±32 pg/mL CSF, demonstrating wide and average levels in the sham group were 56±51 and 39±10 pg/mL (control and PEMF-treated, respectively). Levels stayed fairly low at 6 hours after injury, but rose approximately 5-fold to reach a maximum of 224±23 pg/mL at 17 hours after injury, a 7 to 8-fold increase over basal levels, and to a similar degree as IL-1β levels in CSF from animals receiving the closed-skull contusion. In contrast, animals that received PEMF treatment did not exhibit significant increases in IL-1β, which was maintained at approximately basal levels (23±18 pg/mL CSF), or ten-fold lower than rats that received an injury and were not exposed to PEMF signals. Concentrations of IL-1β remained high in the injured control group at 24 hours (122±56 pg/mL), and decreased to baseline levels at 4 to 9 days after injury (31-45 pg/mL), which persisted throughout this period. IL-1β concentrations were lowest in both groups at 9 days (0-2 pg/mL). Taken together, results demonstrate that PEMF treatment suppressed IL-1β levels in CSF throughout a 9-day period after penetrating brain injury.

PEMF treatment increased OX-42 expression after penetrating injury. The CNS responds to focal penetrating injuries by mounting a local inflammatory response. Using the penetrating injury TBI model, the effects of PEMF treatment on microglial activation were examined. Animals received bilateral penetrating injuries and were assigned to PEMF or null treatment groups, where they received continuous treatment until sacrifice at 3.5 hours to 9 days after lesioning. Results demonstrate that OX-42 staining was absent in the area of the lesion at 3.5 and 6 hours. Beginning at 17 hours after injury, OX-42 immunoreactivity was detected increasing in intensity and size over 5 days. At 9 days, the last time point, staining was most intense and appeared more focal, encompassing the lesion itself a compacted surrounding area with a well-defined perimeter. Initially, the extent of staining was analyzed in a semi-quantitative by rating the intensity and area of staining on a scale of 1 to 5 in 0.25 increments by four blinded observers. The overall degree of OX-42 expression, a combination of staining intensity and the area of staining, increased over the 9 days of the experiment.

Significantly, PEMF signals increased the intensity of OX-42 staining at 24 and 48 hours after injury. This increase was transient, as values were higher, but similar to control levels at both 5 and 9 days after injury. The area occupied by OX-42+ cells at 9 days was smaller than at 5 days, indicating that microglia had arrived at their destination. Image analysis was employed to confirm our observations. Areas (mm2) and mean gray values (average value of pixels over the area in which OX-42 staining was found) were measured on Image J for groups of animals receiving PEMF (null) signals for 24 and 48 hours. Interestingly, the area of OX-42 staining at 24 hours after injury significantly decreased in the PEMF-treated animals compared to controls, but in contrast, the mean intensity of OX-42 immunoreactivity was significantly higher, suggesting that PEMF signals accelerated microglial activation and migration. The intensity of OX-42 immunoreactivity increased in both groups at 48 hours after injury, but neither differences in staining intensity nor the area encompassed by microglia were statistically significant. After 5 days, both staining intensity and areas of microglial activation were essentially the same for both groups of animals.

Figure 6A:
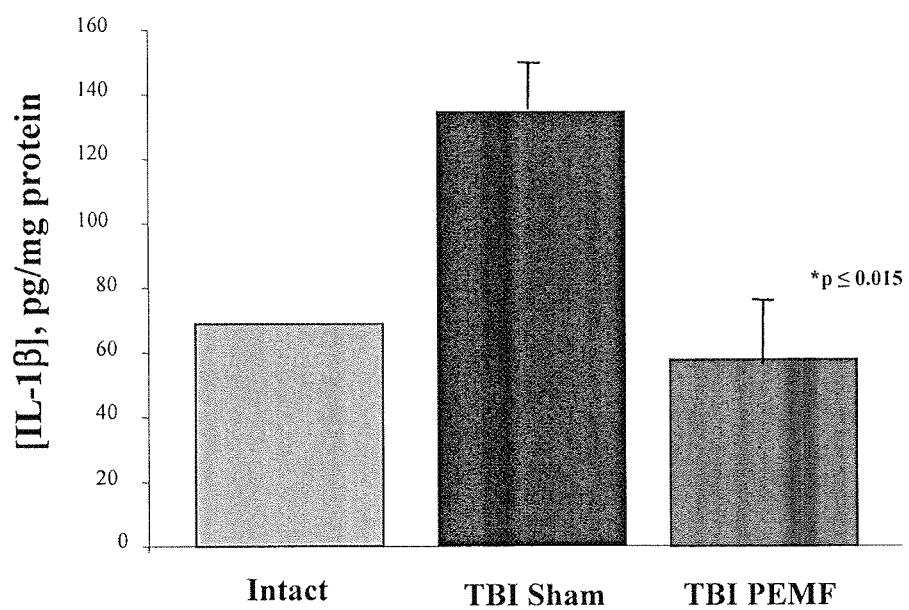
FIGS. 6A-6C illustrate the effect of a PEMF treatment according to embodiments described on rats subjected to contusive traumatic brain injury and invasive brain injury.
Figure 6B:
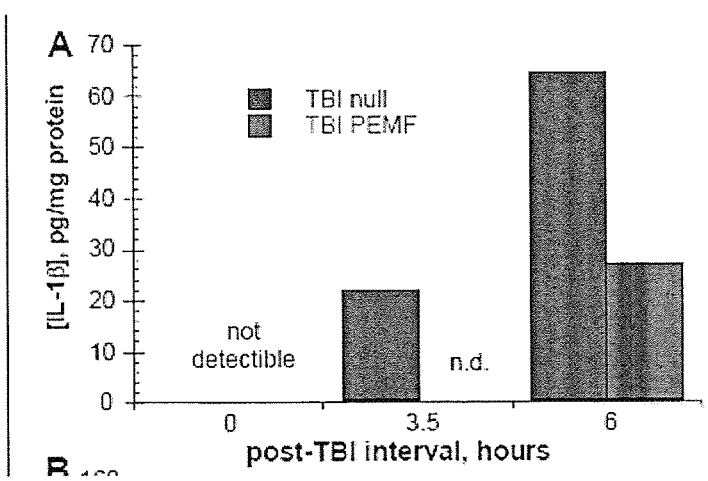
Figure 6C:
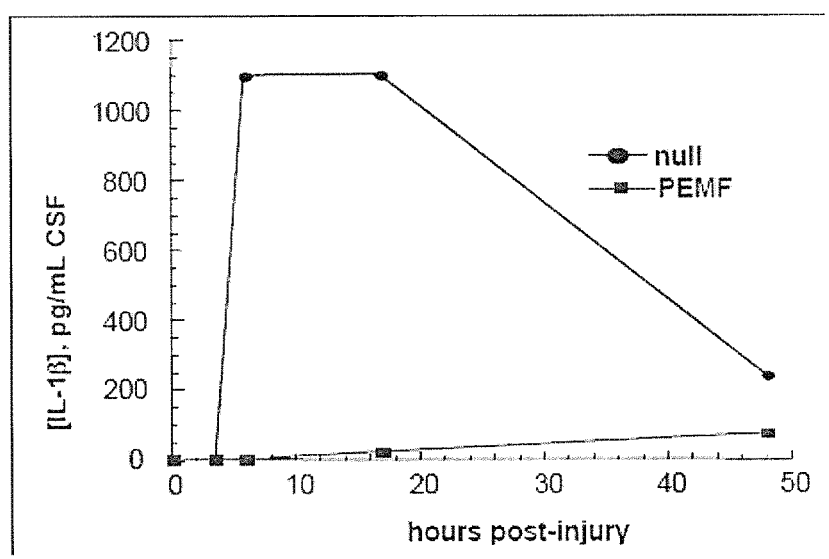

In addition, FIGS. 6A-6C illustrate some results discussed above. In the contusive study, animals were sacrificed and brains homogenized to determine the EMF effect on the master pro-inflammatory cytokine. FIG. 6A shows the results from the contusive study where EMF reduced IL-1β by approximately 10-fold in CSF in treated vs control animals.

In the invasive injury study, brains were collected in intact animals at 0, 3.5, and 6 hours and assayed for levels of 1L-1β by ELISA. Results shown in FIG. 6B demonstrate that IL-1β levels in brain tissue were lower in injured rats treated with PEMF than that of the null group for both models.

Similarly, FIG. 6C shows data from the same study where rats were subjected to bilateral invasive penetrating needle injuries into the striatum. CSF samples were collected under anesthesia from single rats at time specified by the symbols shown in FIG. 6C and analyzed by ELISA. The results suggest that IL-1β appears in CSF 6 hours after invasive trauma and, importantly, levels appear to be suppressed by PEMF treatment.

These results indicate that EMF, configured according to embodiments described, produced a very rapid drop in the inflammatory response to traumatic brain and cervical injury which no other pharmacological or physical modality has been able to achieve. An important factor is that these results were obtained with a portable disposable device which can be incorporated in kits for field response to brain trauma, stroke and other neurological injuries.

Example 5 In this example, the effect of a radio frequency EMF signal, configured according to an embodiment of the present invention consisting of a 27.12 MHz carrier, pulse-modulated with a 3 msec burst repeating at 2 Hz and a peak amplitude of 0.05 G, on post-operative pain was studied in a randomized double-blind clinical study on breast reduction patients. Patients were treated with EMF, configured according to an embodiment of the present invention, delivered to the target tissue with a disposable device, similar to that illustrated in FIG. 2B, which was incorporated in the post-surgical dressing.

Figures 7A, 7B:
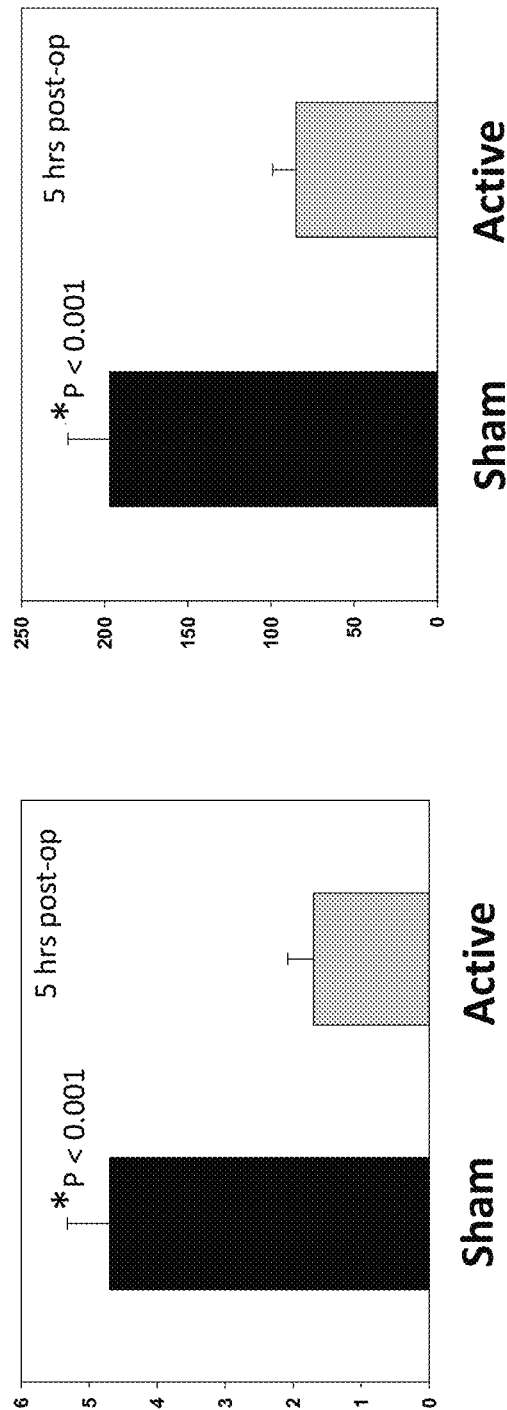
FIGS. 7A and 7B illustrate the effect of a PEMF treatment according to embodiments described on post-operative breast reduction patients.

Treatment regimen for active patients was 30 min every 4 hours for three days. Sham patients received the same EMF device which did not deliver a signal. Wound exudates were collected and pain was assessed by participants using a validated Visual Analog Scale (VAS). Concentrations of IL-1β, a major pro-inflammatory cytokine, were approximately 3-fold lower at 5 hours post-op (P<0.001) in wound exudates from EMF-treated patients compared to those of the control group. EMF also produced a concomitant 2-fold decrease in pain at 1 hour (P<0.01) and a 2.5-fold decrease at 5 hours post-op (P<0.001), persisting to 48 hours post-op. No significant changes in VAS scores were observed in the control group. Furthermore, the increased levels of analgesia were reflected in a 2.2-fold reduction in narcotic use in patients receiving active treatment over the first 24 hours post-op (P=0.002). Importantly, the time course for both pain and IL-1β reduction were concomitant, showing that EMF, configured to modulate CaM/NO signaling in an embodiment according to the present invention, produced endogenous changes in the dynamics of IL-1β availability, which impacts the many known subsequent inflammatory events that are mediated by this cytokine, including those leading to post-operative pain. These results, which are illustrated in FIGS. 7A-B, demonstrate that EMF, configured according to an embodiment of the present invention produced a rapid, non-pharmacological, non-invasive post-operative anti-inflammatory response which significantly reduced patient morbidity and the cost of health care, and enhanced healing.

Figure 9:
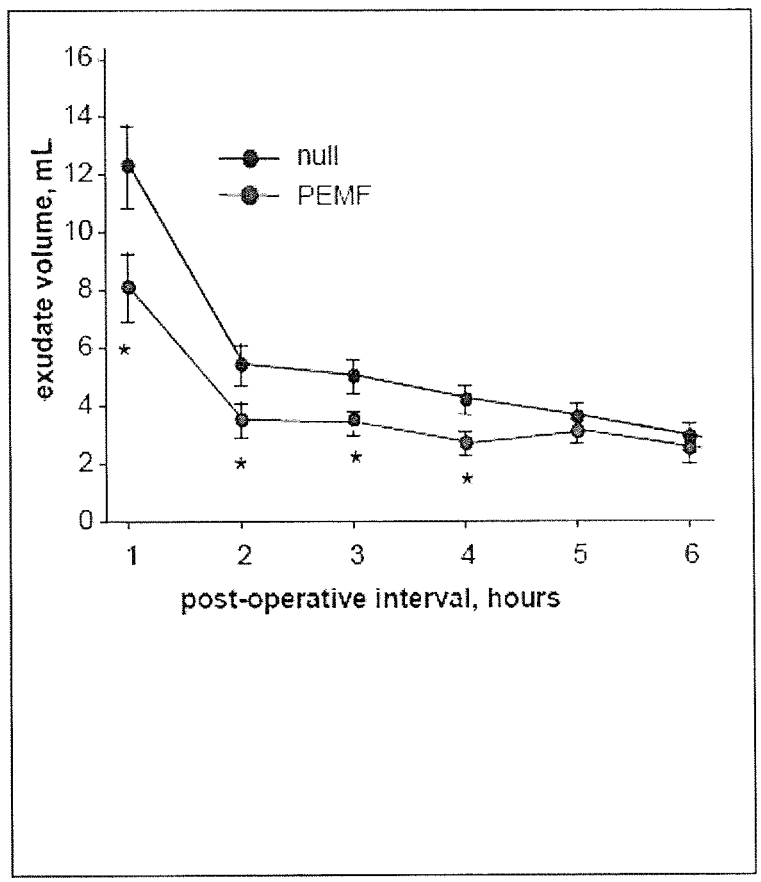
FIG. 9 illustrates the effect of a PEMF treatment according to embodiments described on wound exudate volumes in post-operative patients under breast reduction surgery.

Example 6 This example studies PEMF treatment to attenuate post-traumatic edema. PEMF signals, including a radiofrequency signals, have been shown to reduce the edema associated with various types of peripheral tissue injury. For example, in a double-blinded study of human subjects undergoing breast-reduction surgery, post-operative subjects were treated with a PEMF signal consisting of a 27.12 MHz carrier, pulse-modulated with a 3 msec burst repeating at 2 Hz and a peak amplitude of 0.05 G. As shown in FIG. 9, wound exudates were collected for analysis and volumes were measured at regular post-operative intervals. Results demonstrate a 30% reduction in volumes in the first 4 hours after surgery. Asterisks in FIG. 9 indicate lower volumes in the group of post-operative subjects receiving PEMF treatment (*p≤0.03).

With this current example, PEMF signals will be shown to attenuate increases in brain volume, intracranial pressure, and T2-weighted MRI signals. Animals will be subjected to the weight-drop injury and randomly assigned to receive PEMF (or null) signals. Thirty rats will be implanted with a Codman micro-sensor ICP probe (Codman, Raynham, Mass.) at the same time that the scalp is prepared for the weight-drop injury, as described for use in rats by Williams.

Using a stereotactic frame, a burr hole will be made at −4 mm posterior to and 5 mm lateral to Bregma and the probe will be inserted to a depth of 2 mm. Baseline ICP will be monitored 10 minutes before the injury. The protruding part of the probe will be removed during impact. After injury, 2 groups (n=15) will be treated with PEMF or null signals for 5 minutes every 20 minutes for 8 hours and the sham group will be maintained under similar conditions. The PEMF signal configuration used may be a sinusoidal wave at 27.12 MHz with peak magnetic field B=0.05 G (Earth=0.5 G), burst width, T1=5 msec, and repetition rate T2=2/sec as shown in FIG. 10A. The PEMF signal configuration may also induce a 1-5 V/m peak electric field in situ with a duty cycle=2%, without heat or excitable membrane activity produced. The field may be applied through an electrical pulse generator to a coil tuned to 27.12 MHz. The burst width (5 msec) and repetition rate (2 Hz) were chosen by comparing the voltage induced across the $Ca^{2+}$ binding site over a broad frequency range to noise fluctuations over the same range. Effects of burst widths of two 27.12 MHz sinusoidal signals at 1 Hz are illustrated in FIG. 10B. As shown in FIG. 10B, high signal-to-noise ratios (SNRs) can be achieved in the relatively low frequency range and at peak magnetic field 0.05 G.

Animals will be re-anesthetized at 30 minutes, 1 hour, 4 hours, and 8 hours and the probe will be re-inserted for ICP measurement. After the final measurement, animals will be euthanized. ICP of both injury groups will be compared over time with respect to pre- and post-injury values and effects of PEMF (vs. null) to determine the extent and kinetics of ICP for this model and to determine whether PEMF signals can attenuate the magnitude of ICP or protract the rise in ICP over time.

T2-weighted Magnetic Resonance Imaging: Thirty rats will undergo contusive injuries and will be randomly assigned to receive PEMF or null signals (n=15) using a regimen of 5 minutes of treatment every 20 minutes. T2-weighted MRI will be performed at the Gruss Magnetic Resonance Research Center (MRRC) at the Albert Einstein College of Medicine, both before injury and after injury at 3 time points that bracket peak ICP, as established in the pilot experiment (see above). Edema will be calculated using standard MRI algorithms and protocols established at the MRRC. MRI is a validated method of following edema in post injury neurotrauma models. Animals will be transported to the MRRC on a staggered basis. Under isofluorane anesthesia, each animal will be connected to a ventilator and anesthesia will be maintained at 1.5% isofluorane. Ventilation rate will be maintained at 60 breaths/minute, and volume pressure settings will be adjusted to produce stable end-tidal $CO_2$ and regular respiratory movements. Core temperature will be monitored by rectal thermometer and a feedback-controlled water pump will warm the animal while in the MRI cradle. The animal will then be placed into the magnet and imaging data are collected. The animal will then be removed from the magnet, extubated, placed on a feedback-controlled warming pad, and allowed to recover from anesthesia, when it will be returned to its home cage and transported to the Animal Care Facility.

Each T2W slice will be displayed on a workstation and edema will be quantified using the MEDx package after manually outlining areas of signal hyper-intensity that are consistent with edema. Volume will be computed as the sum of area outlined on each slice multiplied by slice thickness. Longitudinal comparison and quantification of edema will allow values for each animal to be compared and normalized to its own baseline. Information from this analysis will include the determination of areas of brain that are most affected by the injury and the ability of PEMF to suppress brain swelling over the period of edema formation. Animals from this study will also be used for $^1$H-MRS imaging.

ICP has been evaluated in response to severe injury in the weight-drop model.

Normally, ICP ranges between 5 and 15 mm Hg. A 450 g weight dropped over 2 meters will result in a rise in ICP to 28±3 mm Hg after 30 min, followed by a gradual decline, measured over 4 hours. Based on PEMF-mediated reductions of wound exudate volumes (FIG. 9), the study results are expected to show that PEMF to has immediate effects on reducing edema. Moreover, the ability to obtain whole brain images with T2-weighted MRI will allow us to identify regions of interest in our model that incur the worst injury and follow them over time.

Example 7

In one study, a group of rats received neural transplants of dissociated embryonic midbrain neurons and were treated twice a day with PEMF or null signals for 1 week. As shown in FIG. 11, OX-42 labeled activated microglia form a "cuff" surrounding the transplant. Alkaline phosphatase-labeled blood vessels were stained in purple. Results of the microglial staining, shown in FIG. 11, demonstrate that microglial activation was less intense in the PEMF group. This study showed that PEMF may attenuate inflammation in response to transplantation. However, the apparent decrease in microglia may be transitory and that microglial activity may actually be increased/accelerated.

Example 8

In this example, rats were subject to penetrating injuries and exposed to PEMF signals according to embodiments described. Brain tissue was processed for OX-42 IHC at specified times after injury to identify activated microglia. As shown in FIG. 12, results demonstrate that the pattern of OX-42 staining in rats that received penetrating injuries was localized to the site of the trauma. Most importantly, staining intensity appears higher with PEMF treatment at 2 and 5 days after injury, indicating activation of microglial cells was accelerated.

Example 9

Figure 13:
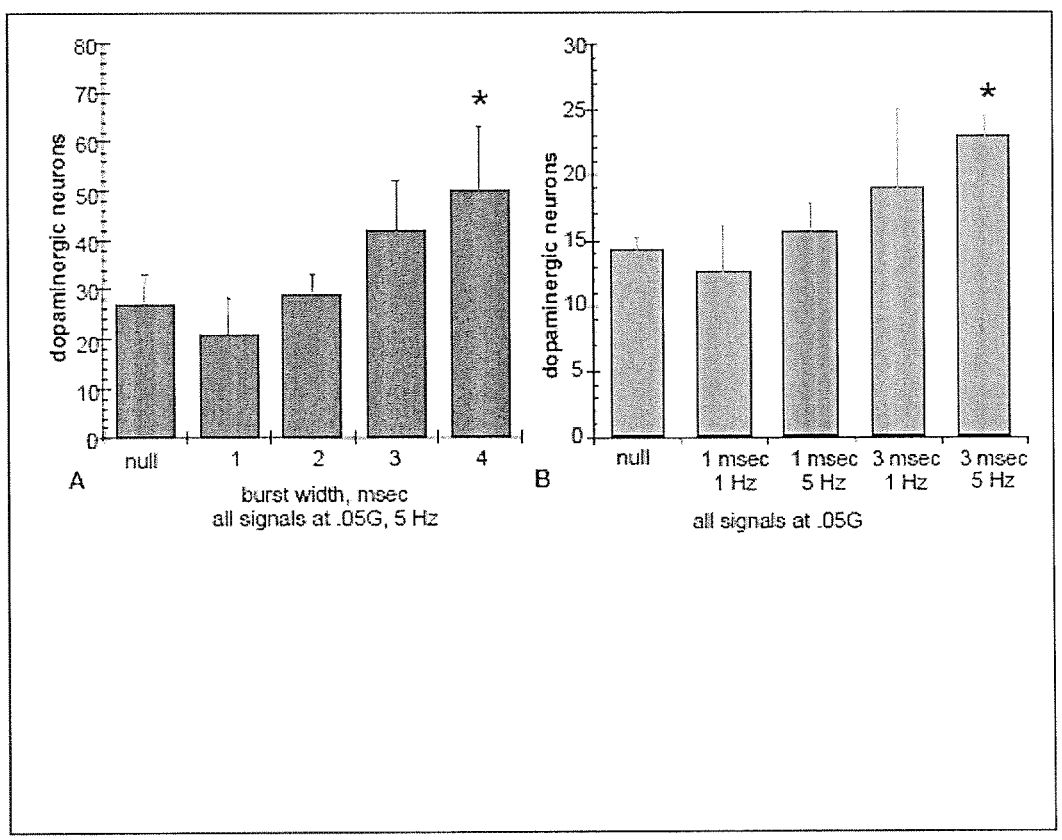
FIG. 13 illustrates the effect of a PEMF treatment according to embodiments described on dopaminergic neurons.

As shown in FIG. 13, neuronal cultures were treated with PEMF signals for 6 days before challenge by (1) reduced serum 1% or (2) 5 µM quisqualic acid, a non-NMDA glutamate receptor agonist. Dopaminergic neurons were identified by tyrosine hydroxylase immunocytochemistry and quantified at 8 days. The bars shown in FIG. 13 indicate mean neuronal numbers (+/−SEM) in triplicate cultures. Asterisk denotes groups with significant differences from the null group (P<0.05). Results indicate that PEMF signals according to embodiments describe provide neuroprotective treatment to prevent neural death.

Example 10

This example will study the ability of PEMF signals to prevent neural death. Animals will be subjected to contusive (weight-drop) TBI. Eighty rats will be randomly assigned to PEMF or null groups and treated for 5 minutes every 20 minutes. A group of rats receiving sham surgery will serve as controls. At 1, 2, 5 and 10 days and after injury, CSF will be collected from 10 animals from each treatment group immediately prior to euthanasia, at which time blood will be collected peri-mortem. Brains will be fixed, cryoprotected, 50 µm vibratome sections will be generated through the cerebrum from approximately −7 to +4 mm with respect to Bregma on the anteroposterior axis. Multiple series of every 6th section will be prepared for analyses described below.

Tissue Necrosis: The overall extent of tissue damage will be assessed on a series of sections after hematoxylin and eosin (H&E) histochemistry, first qualitatively, by observations of astrocytic, neuronal, or dendritic swelling, pyknotic nuclei, and necrosis and then quantitatively, by measuring the area abnormal histology. Regions of damaged tissue will be captured by digital photography and the volume will be assessed by outlining the perimeter using Image J software, calculating the area with calibrated markers, and multiplying by section thickness. Histological abnormalities, as described above, will be quantified within a specified volume of these regions. Data from each group will be compared to determine whether PEMF signals reduce the volume of tissue damage and numbers of cells with abnormal morphology.

Neuronal Injury: Proton Magnetic Resonance Spectroscopy: This study will be conducted on the same animals that will be used for T2-MRI studies (see Example 6), as they will provide information on regions of interest, and to avoid duplications of time and costs associated with live-animal studies. Based on information obtained from T2-weighted MRI (see Example 6), several regions of interest (ROI), defined by anatomical landmarks and changes on T2 maps, will be selected and further analyzed. Studies by other groups suggest that both cortical and hippocampal regions may be the most vulnerable to the injury made in the weight-drop model. Afterwards, computerized graphical analysis of specific, localized spectra in the ROIs will be utilized to determine resonance corresponding to NAA, Cr, Cho, lactate and taurine. Quantitative analysis of the spectroscopic metabolite ratios will be compared among the pre-injury, TBI null, and TBI PEMF groups to determine changes in concentrations of these biochemical markers.

Neuronal Death: Fluoro-Jade staining: Fluoro jade stain is a fluorochrome derived from fluorescein and is commonly used to label degenerating neurons including neurons injured from TBI as an alternative to other methods, such as silver and Nissl stains. Fluoro jade stained tissue can be visualized with epifluorescence using filters designed for fluorescein or fluorescein isothiocynate (excitation 495 nm; emission 521 nm). Multiple morphological features can be detected using fluoro-jade including; cell bodies, dendrites, axons, and axon terminals. Even though all fluoro-jade derivatives can detect these specific morphological features, fluoro-jade C has greater specificity and resolution. A series of every 6th serial section will be processed stained with fluoro-jade-C to identify dying neurons. Sections will be dehydrated in ethanol and rinsed in distilled water, followed by oxidation in 0.06% potassium permanganate for 15 minutes, followed by several water washes. Sections will then be placed in 0.1% acetic acid containing 0.001% fluoro jade C (Millipore) for 1 hour at room temperature. After washing, sections will be dehydrated, cleared and coverslipped for viewing. Areas demonstrating the greatest generalized damage by H&E will be assessed for neuronal damage. Neurons within a defined anatomical structure can be quantified on a series of sections by stereological analysis (i.e. optical dissector) using Neurolucida software (Microbrightfield).

Data from PEMF-treated and null groups will be compared. UCH-L1: Ubiquitin C-terminal hydrolase-L1 (UCH-L1), a neuron-specific protein (also called protein gene product 9.5 or Park 5) involved in protein degradation via the ATP-dependent proteosomal pathway, is abundant in neuronal cell bodies. Mice bearing a spontaneous mutation in this gene demonstrate behavioral disturbances and neuronal loss, and mutations in humans are associated with Parkinson's disease, supporting a sustaining role for this protein in neurons. Importantly, UCL-L1 was identified in a proteomic screen of CSF as a biomarker for neuronal injury. Studies have shown that UCH-L1 is released following severe cortical impact injury and ischemia. This marker has recently gained attention in the general press as a potential CSF marker for brain injury in humans. Therefore, we will evaluate the effects of PEMF on UCH-L1 in CSF, and we will also assess levels in blood, as they can easily be obtained before euthanasia. Although not commercially available, we will devise an ELISA to quantify UCH-L1 using chicken and rabbit UCH-L1 polyclonal antibodies (Cell Signaling and Thermo Scientific, respectively), as described by others. Plates will be coated with anti-UCH-L1, followed by washing and aliquots of CSF, or blood. Protein will be identified with HRP-anti UCH-L1 and a soluble substrate for peroxidase. Western blots for UCH-L1 (a 24 kD protein) will be run with selected samples to validate ELISA data. Levels of UCH-L1 should be inversely proportional to the extent of neuronal death.

Axonal Injury: A series of sections from injured animals in PEMF and null groups and sham controls will be processed for silver staining with this method. Briefly, mounted tissue sections are pre-incubated in an alcoholic solution containing silver and copper nitrates, washed in acetone, and impregnated in silver nitrate with lithium and ammonium hydroxides, followed by reduction in formalin, citric acid and ethanol. After acidification, bleaching, and fixation, slides will be coverslipped for viewing. Tissue sections will be processed commercially (Neuroscience Associates, Knoxville, Tenn.), as this technique requires a number of hazardous solutions that require special processing and disposal. Silver-impregnated, degenerating neurons and processes will stain black, progressing to a Golgi-like intensity. More lightly stained terminals and lysosomes may only be apparent at earlier time points, as these structures often degenerate prior to axonal loss. For quantification of degeneration, images will be digitized and the density of optical staining over an assigned area of cortex will be quantified by densitometry with Image J Software. This method has been validated by others.

Predicted Results: The time course of pathological events following TBI are the direct destruction of tissue (including neurons) if the injury is invasive, followed by edema, inflammation, axonal injury, and subsequently delayed neuronal death. The Marmarou weight-drop method induces all of these events in a more protracted fashion. Cell culture experiments indicate that neuronal survival is increased with PEMF directly in response to an excitotoxic insult, suggesting that neurotoxicity due to ischemia and subsequent release of glutamate may also be attenuated by PEMF signals in vivo. Because brain swelling and inflammation result in indirect neurotoxicity, increased survival by PEMF is also predicted for this pathway. Positive results will confirm that treatment with PEMF signals can be used to attenuate the damage caused by traumatic, closed head injury and may have therapeutic implications for other types of TBI as well as more acute and chronic neurodegenerative diseases, such as stroke, Alzheimer's disease, and Parkinson's disease where many of these same mechanisms are known to be involved.

Example 11

In this example, rats will be subjected to the Marmarou weight-drop TBI model to produce moderate behavioral deficits. Individual naive animals will be subjected to general assessments and sensorimotor behavioral testing. Those animals whose behavior falls in the normal range will receive moderate TBI using the weight-drop model and will be randomly assigned to receive PEMF or null signals using the regimen of 5 minutes every 20 minutes. At 1, 2, 7, 14, and 21 days after injury, animals will be re-assessed for general behaviors and neurological function to quantify the magnitude of these basic deficits. At 1 month after surgery, animals will be transported to the Bronx VA for long-term cognitive testing. After acclimation to the VA animal holding facility (2 weeks), testing will take place over 8 weeks for each animal by the same technician.

Rats will first be evaluated for general health and spontaneous and elicited behavior. These basic observations will be supplemented with an assessment of motor, sensory and general activity level using rotarod, grip strength, balance beam, and tail-flick analgesia tasks to determine whether the injury has affected the general health status and overt behavioral profile of the rat in a way that would make its general behavior incompatible with more complex behavioral assays. Moreover, if specific deficits are identified in the basic screen, we may be able to alter the choice of more complex behavioral assays to account for the deficit. We will then proceed to more detailed testing. Rats will be observed in an open field assay to assess both general motor activity and anxiety related behavior, and an elevated plus maze as an additional indicator of anxiety related behavior. In the cognitive domain we will administer at least three tests designed to measure learning and memory related functions: 1) the Morris water maze, a standard test of hippocampal dependent spatial memory 2) a test of contextual and cued fear conditioning, which is highly dependent on amygdaloid function and requires a set of motor and sensory abilities distinct from those required for spatial navigation, and 3) a Y-maze task, a test of working memory. We will also measure response to acoustic startle and pre-pulse inhibition as measures of auditory function and sensory gating, physiological functions that can be affected in TBI.

Order of testing and timetable: Carryover effects can significantly confound behavioral testing in rodents. The testing order will be as described except that the cued fear conditioning and Morris water maze tests will be performed last in the sequence, as these include the most demanding and stressful tasks. Based on our prior experience in rodent behavioral work, testing will require: Basic screen (SHIRPA) (7 days), Rotarod (2 days), Grip strength (1 day), Tail flick (1 day), open field (3 days), elevated plus maze (2 days), Morris water maze (4 weeks), contextual/cued fear conditioning (2 days), Y-maze (2 days) and acoustic startle/PPI (2 days) or approximately 8 weeks of testing.

Data analysis: Data will be analyzed using GraphPad Prism 5.0 (GraphPad Software, San Diego, Calif.) or SPSS 18.0 (SPSS, Chicago, Ill.) software as in previous studies. Depending on the behavioral test, statistics will employ univariate or repeated measures analysis of variance (ANOVA), unpaired t-tests or linear regression. Equality of variance will be assessed using the Levene test and when it is not significant ($p > 0.05$) between-group comparisons will be made with unpaired t-tests (Student's) or Tukey post-hoc tests. If the Levene statistic is significant ($p < 0.05$) unpaired t-tests will be used using the Welch correction for unequal variances. For repeated-measures ANOVA, sphericity will be assessed using Mauchly's test. If the assumption of sphericity is violated (p<0.05, Mauchly's test), significance will be determined using the Greenhouse-Geisser correction.

Predicted Results: Data from PEMF and null groups will be compared with naive animals to determine the degree of deficit and with each other to determine whether PEMF signals improve neurological function. It is expected that PEMF treatment will show a decrease in the degree of initial deficits and/or accelerate or enhance the degree of recovery.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A non-invasive method for treating a traumatic neurological injury or condition in a patient in need thereof, the method comprising:
   externally placing a pulsed electromagnetic device in proximity to a target region for treatment through a skull;
   generating a first pulsed electromagnetic field from a pulsed electromagnetic field source, having a strength of 200 milliGauss or less wherein the pulsed electromagnetic field comprises bursts of between 5-50 MHz sinusoidal waves, wherein the bursts repeat at between 0.01 and 100 Hz;
   applying the external pulsed electromagnetic field to the target region affected by the neurological injury or condition, wherein the neurological injury or condition includes traumatic brain injury (TBI); and
   reducing a physiological response to the neurological injury or condition by applying the external pulsed electromagnetic field.

2. The method of claim 1, wherein the physiological response is inflammation.

3. The method of claim 1, wherein the physiological response is increased intracranial pressure.

4. The method of claim 1, further comprising monitoring the physiological response; and
   continuing to apply the pulsed electromagnetic field until an acceptable level of the physiological response is reached.

5. The method of claim 4, wherein the physiological response is increased intracranial pressure and the acceptable level is below about 20 mmHg.

6. The method of claim 1, wherein generating the pulsed electromagnetic field comprises a 2 msec burst of 27.12 MHz sinusoidal waves repeating at 2 Hz.

7. The method of claim 1, wherein the pulsed electromagnetic field comprises a 3 msec burst of 27.12 MHz sinusoidal waves repeating at 2 Hz.

8. The method of claim 1, wherein the pulsed electromagnetic field comprises a 4 msec burst of 27.12 MHz sinusoidal waves repeating at 2 Hz.

9. The method of claim 1, wherein the pulsed electromagnetic field comprises about a 1 msec to about a 10 msec burst of 27.12 MHz sinusoidal waves repeating at about 1 Hz to about 10 Hz.

10. The method of claim 1, wherein the pulsed electromagnetic field comprises an ISM carrier frequency modulated at about a 1 msec to about a 10 msec burst repeating at about 1 Hz to about 10 Hz.

11. The method of claim 1, wherein the physiological system is the central nervous system.

12. The method of claim 1, wherein the physiological system is the cardiac system.

13. The method of claim 1, wherein the physiological system is the pulmonary system.

14. The method of claim 1, wherein the electromagnetic field comprises a waveform that modulates at least one biological signaling pathway.

15. The method of claim 1, wherein the target region is a brain of the patient.

16. The method of claim 1, further comprising prior to generating the pulsed electromagnetic field from the pulsed electromagnetic field source:
   pre-programming a pulsed electromagnetic waveform to treat the target brain region affected by the traumatic brain injury (TBI);
   placing the pulsed electromagnetic field source adjacent to the target brain region for treatment through a skull;
   wherein generating the pulsed electromagnetic field from the pulsed electromagnetic field source includes the pre-programmed pulsed electromagnetic waveform.

17. A non-invasive method for treating a traumatic neurological injury or condition in a patient in need thereof, the method comprising:
   externally placing a pulsed electromagnetic device in proximity to a target region for treatment through a skull;
   generating a first pulsed electromagnetic field from a pulsed electromagnetic field source, having a strength of 200 milliGauss or less wherein the pulsed electromagnetic field comprises bursts of between 5-50 MHz sinusoidal waves, wherein the bursts repeat at between 0.01 and 100 Hz;
   applying the first pulsed electromagnetic field in proximity to a target region affected by the neurological injury or condition, wherein the neurological injury or condition includes traumatic brain injury (TBI);
   reducing a physiological response to the neurological injury or condition for a first treatment interval by applying the first pulsed electromagnetic field;
   discontinuing the application of the first pulsed electromagnetic field for an inter-treatment period greater than zero; and
   applying a second pulsed electromagnetic field in proximity to the target region.

18. The method of claim 17, wherein the first and second pulsed electromagnetic fields are substantially the same.

19. The method of claim 17, further comprising monitoring the physiological response; and
modifying the first pulsed electromagnetic field to the second pulsed electromagnetic field in response to the monitoring step.

20. The method of claim 17, further comprising monitoring the physiological response; and
discontinuing treatment once an acceptable level of the physiological response is reached.

21. The method of claim 17, further comprising attenuating inflammatory cytokines and growth factors at the target region by applying the first pulsed electromagnetic field or the second pulsed electromagnetic field to the target region.

22. The method of claim 17, further comprising accelerating the healing of the target region by applying the first pulsed electromagnetic field or the second pulsed electromagnetic field to the target region.

23. The method of claim 17, wherein applying the first pulsed electromagnetic field in proximity to a target region affected by the neurological injury or condition to reduce a physiological response comprises reducing a concentration of IL-Iβ.

24. The method of claim 17, further comprising increasing a growth factor in the target region.

25. The method of claim 24, wherein increasing a growth factor in the target region enhances angiogenesis.

26. The method of claim 24, wherein increasing a growth factor in the target region enhances nervous tissue regeneration.

27. The method of claim 24, wherein the growth factor is selected from the group consisting of FGF-2, VEGF, and BMP.

28. The method of claim 17, wherein the target region is a brain of the patient.

29. The method of claim 17, wherein the inter-treatment period is greater than two hours.

30. A non-invasive method for treating a traumatic neurological injury or condition in a patient in need thereof, the method comprising:
externally placing a pulsed electromagnetic device in proximity to a target region for treatment through a skull;
pre-programming a pulsed electromagnetic waveform to treat a target brain region affected by a neurological injury or condition, wherein the neurological injury or condition includes traumatic brain injury (TBI);
placing the pulsed electromagnetic device adjacent to the target brain region;
generating a pulsed electromagnetic field from a pulsed electromagnetic field source, having a strength of 200 milliGauss or less wherein the pulsed electromagnetic field comprises bursts of between 5-50 MHz sinusoidal waves, wherein the bursts repeat at between 0.01 and 100 Hz, the pulsed electromagnetic field including the pulsed electromagnetic waveform;
applying the pulsed electromagnetic field to the target brain region affected by the traumatic brain injury; and
accelerating and increasing the binding of Ca2+ to Calmodulin in the target brain region and reducing a physiological response to the traumatic brain injury by applying the pulsed electromagnetic field.

31. A non-invasive method of promoting neurological repair or growth following a traumatic neurological injury or condition comprising:
placing a treatment coil of a self-contained, lightweight, and portable treatment apparatus externally to a target treatment site through the skull in need of repair or development, wherein the treatment apparatus comprises a conformable coil having one or more turns of wire and a control circuit;
generating an electromagnetic field using the treatment coil, having a strength of 200 milliGauss or less wherein the pulsed electromagnetic field comprises bursts of between 5-50 MHz sinusoidal waves, wherein the bursts repeat at between 0.01 and 100 Hz;
delivering the electromagnetic field to the target treatment site using the treatment coil; and
reducing a physiological response to the neurological injury or condition by delivering the electromagnetic field, wherein the neurological injury or condition includes traumatic brain injury (TBI).

32. The method of claim 31, further comprising delivering the electromagnetic field for a period of about 1 minute to about 240 minutes.

33. The method of claim 31, wherein the physiological response is a cognitive deficiency.

34. The method of claim 31, wherein the target treatment site is a brain.

* * * * *